United States Patent
Bader et al.

(10) Patent No.: US 10,214,530 B2
(45) Date of Patent: Feb. 26, 2019

(54) XANTHINE DERIVATIVES, THEIR USE AS A MEDICAMENT, AND PHARMACEUTICAL PREPARATIONS COMPRISING THE SAME

(71) Applicants: MAX-DELBRÜCK-CENTRUM FÜR MOLEKULARE MEDIZIN, Berlin (DE); FORSCHUNGSVERBUND BERLIN E.V., Berlin (DE)

(72) Inventors: Michael Bader, Berlin (DE); Edgar Specker, Berlin (DE); Susann Matthes, Berlin (DE); Anja Schütz, Berlin (DE); Keven Mallow, Berlin (DE); Maik Grohmann, Eltville (DE); Marc Nazaré, Berlin (DE)

(73) Assignee: MAX-DELBRÜCK-CENTRUM FÜR MOLEKULARE MEDIZIN, Berlin (DE)

( * ) Notice: Subject to any disclaimer, the term of this patent is extended or adjusted under 35 U.S.C. 154(b) by 0 days.

(21) Appl. No.: 15/552,556

(22) PCT Filed: Feb. 24, 2016

(86) PCT No.: PCT/EP2016/053872
§ 371 (c)(1),
(2) Date: Aug. 22, 2017

(87) PCT Pub. No.: WO2016/135199
PCT Pub. Date: Sep. 1, 2016

(65) Prior Publication Data
US 2018/0051025 A1    Feb. 22, 2018

(30) Foreign Application Priority Data

Feb. 24, 2015  (EP) .................................. 15156418

(51) Int. Cl.
| | | |
|---|---|---|
| C07D 473/06 | (2006.01) |
| C07D 487/04 | (2006.01) |
| C07D 519/00 | (2006.01) |
| A61K 31/522 | (2006.01) |
| A61P 3/04 | (2006.01) |
| A61P 11/06 | (2006.01) |
| A61P 19/10 | (2006.01) |
| A61P 25/18 | (2006.01) |
| A61P 25/24 | (2006.01) |
| A61P 29/00 | (2006.01) |
| A61P 35/00 | (2006.01) |

(52) U.S. Cl.
CPC ......... *C07D 473/06* (2013.01); *C07D 487/04* (2013.01); *C07D 519/00* (2013.01)

(58) Field of Classification Search
CPC ... C07D 473/06; C07D 519/00; C07D 487/04
See application file for complete search history.

(56) References Cited

U.S. PATENT DOCUMENTS
2013/0137635 A1    5/2013 Sands

FOREIGN PATENT DOCUMENTS
WO    2011100285 A1    8/2011

OTHER PUBLICATIONS

Matthes, S., "Peripheral serotonin synthesis as a new drug target." Trends in pharmacological sciences (2018).*
Rumrich, I.K.,"Environnmental Reduction Potential of Asthma Burden in Finland." (2014).*
https://www.webmd.com/lung/copd/tc/chronic-obstructive-pulmonary-disease-copd-prevention 2005.*
Database Registry Chemical Abstracts Service, Columbus, Ohio, 2018.*
McKim, A. S., "Dimethyl sulfoxide USP, PhEur in approved pharmaceutical products and medical devices." Pharmaceutical Technology 32.5 (2008): 74.*
Oxford University Press 2001, www.oed.com/view/Entry/115686?rskey=vCsqFU&result=1&print.*

(Continued)

*Primary Examiner* — John M Mauro
(74) *Attorney, Agent, or Firm* — Norris McLaughlin, PA

(57) ABSTRACT

The invention relates to a xanthine derivative defined by chemical formula I or a salt thereof, its use as a medicament, especially for use in the treatment of serotonin-related diseases or disorders, and a pharmaceutical preparation comprising the xanthine derivative.

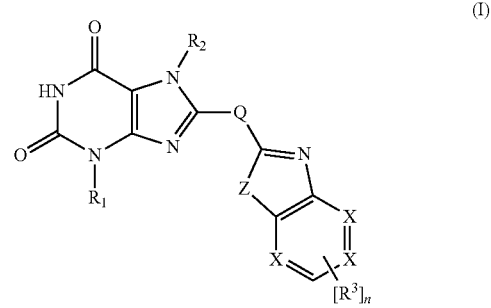

Figure 1A:

The novel xanthine compounds are capable of inhibiting tryptophan hydroxylases (TPH) involved in the biosynthesis of serotonin and are effective in influencing the serotonin level in the body.

14 Claims, 1 Drawing Sheet

(56) References Cited

OTHER PUBLICATIONS

Frandsen H. et al., "N-acetyltransferase-dependent activation of 2-hydroxyamino-1-methyl-6-phenylimidazo[4,5-b] pyridine: formation of 2-amino-1-methyl-6-(5-hydroxy)phenylumidazo[4,5-]pyridine, a possible biomaker for the reactive dose of 2-amino-1-methyl-6phenylimidazo[4,5-b]pyridine", Carcinogenesis, Oxford University Press, GB, vol. 21, No. 6. pp. 1197-1203, Jun. 2000.
Lei Zhang et al., "Discovery of Novel Vascular Endothelial Growth Factor Receptor 2 Inhibitors: A Virtual Screening Approach", Chemical Biology & Drug Design vol. 80, No. 6 pp. 893-901, Dec. 2012.
International Search Report dated Mar. 31, 2016, dated Aug. 4, 2016.
European Search Report dated Jun. 2, 2015.

\* cited by examiner

XANTHINE DERIVATIVES, THEIR USE AS A MEDICAMENT, AND PHARMACEUTICAL PREPARATIONS COMPRISING THE SAME

This application is the U.S. National Stage of International Application No. PCT/EP2016/053872, filed Feb. 24, 2016, which claims foreign priority benefit under 35 U.S.C. § 119 of European Application No. 15156418.4 filed Feb. 24, 2015.

The invention relates to novel xanthine derivatives effective in inhibiting tryptophan hydroxylases (TPH). The invention is further directed to the xanthine derivative for use as a medicament, particularly for use in the treatment of serotonin-related diseases and disorders, and pharmaceutical preparations comprising the xanthine derivative.

BACKGROUND OF THE INVENTION

Serotonin (5-hydroxytryptamine, 5-HT) is an evolutionary ancient biochemical, widespread throughout the animal and plant kingdoms. In mammals, serotonin acts as a neurotransmitter within the central and peripheral nervous systems (CNS, PNS) and as a local hormone in various other non-neuronal tissues, including the gastrointestinal tract, the cardiovascular system and immune cells. This functional duality of the serotonin system is typical for all vertebrates.

Within mammalian organisms only a few cell types synthesize serotonin, indicated by the expression of tryptophan hydroxylase (TPH) which is the initial and rate-limiting enzyme in the biosynthesis of serotonin. The multiplicity of serotonin actions is linked to many complex physiological and pathological functions. In mammals, about 70-90% of the total serotonin resides in the gastrointestinal tract, assisting digestive activities. There, it is mainly produced by enterochromaffin cells (EC) and by neurons of the enteric nervous system (ENS). Both cell types release serotonin upon mechanical or chemical stimuli, to induce contraction of smooth muscle cells and to regulate intestinal motility, secretion and intestinal blood flow. Serotonin from EC also enters the circulation and is taken up by thrombocytes and stored in specific vesicles. Platelet-derived serotonin plays a role in liver regeneration and primary haemostasis after vessel injury. Peripheral serotonin is also known to be involved in pulmonary hypertension, cardiac function, cardiac morphogenesis, ontogenesis, mammary gland plasticity, cancer, T-cell-mediated immune response and insulin secretion from pancreatic β-cells. The highest concentration of peripheral serotonin is found in the pineal gland, where it serves as precursor molecule for the biosynthesis of melatonin, a neuronal hormone involved in many physiological processes like thermoregulation and sleep.

Because of its hydrophilic properties, serotonin is not able to penetrate the blood-brain barrier (BBB). Therefore it needs to be synthesized in the brain, by serotonergic raphe neurons of the brainstem.

Central serotonin is important for the brain development. Furthermore, it is partaking in the regulation of sleep, body temperature, respiratory drive, motor control, CNS vascular tone, pain sensation and nociception. In addition, serotonin affects nearly all behavioural patterns, including memory, general mood, stress response, aggression, fear, appetite, addiction as well as maternal and sexual behaviour. An imbalance in the serotonin system has been implicated in a multitude of neuropsychiatric diseases.

The biosynthesis of serotonin is a highly regulated two-step process, starting with the essential amino acid L-tryptophan (Trp), cf. scheme below. The first and rate-limiting step comprises the hydroxylation of Trp to 5-hydroxytryptophan (5-HTP). This reaction is carried out by the enzyme tryptophan hydroxylase (TPH) and requires $Fe^{2+}$ ions as a cofactor and molecular oxygen ($O_2$) and tetrahydrobiopterin ($BH_4$) as co-substrates. Two isoforms of TPH (TPH1 and TPH2) exist, reflecting the functional duality of serotonin on the biochemical level. Secondly, 5-HTP is immediately decarboxylated to 5-hydroxytryptamine (5 HT) by the ubiquitously expressed aromatic amino acid decarboxylase (AAAD).

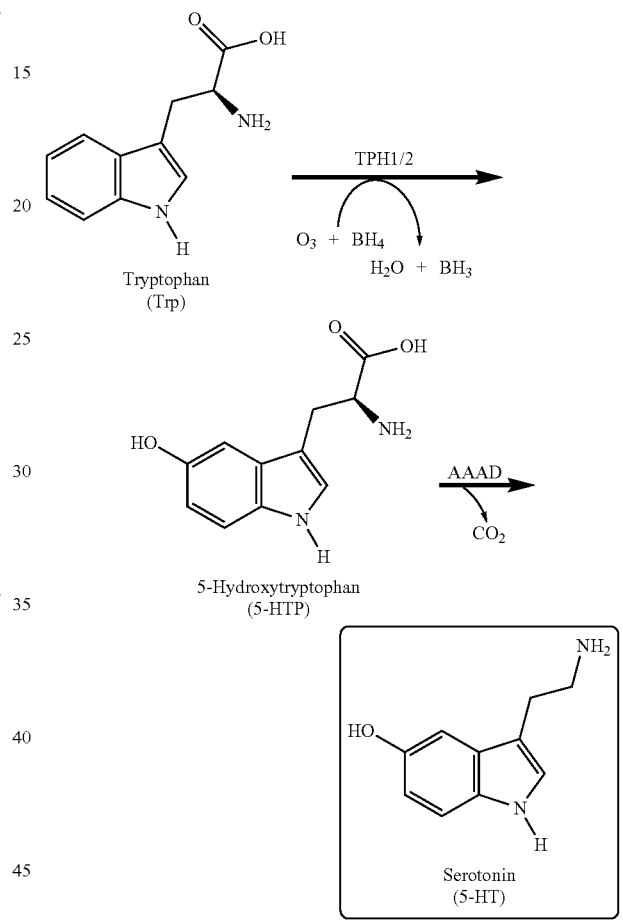

Biosynthesis of Serotonin (5-HT).
TPH1/2: Tryptophan hydroxylase 1 and 2, AAAD: Aromatic amino acid decarboxylase.

TPH1 and TPH2 proteins in vertebrates are highly homologous, sharing an overall 70% amino acid sequence identity in humans, but differ in their kinetic properties and, more remarkably, in their tissue distribution. Further studies of mRNA and protein levels in rodent and human tissues confirmed TPH2 to be the central isoform, predominantly expressed in raphe neurons of the brainstem and in peripheral myenteric neurons in the gut, while it is absent in peripheral organs, such as lung, heart, kidney or liver. On the other hand, TPH1 is mainly found in the gastrointestinal system as well as in the pineal gland, where it produces serotonin serving as a precursor molecule for melatonin biosynthesis.

The disability of serotonin to cross the BBB enforces the dualistic character of the serotonin system by creating two physiologically separated serotonin pools in the body. In fact, both serotonin systems are defined by the TPH1 and TPH2 isoforms and characterized by distinct physiological functions and independent regulatory mechanisms. Consequently, both systems can be targeted in an autonomous fashion to pharmacologically or genetically manipulate central and peripheral serotonin functions.

The catalytic domain of TPH is highly conserved and incorporates all of the residues required for enzyme activity and substrate binding. Data from X-ray structures of the catalytic domain helped to establish the structure of the active site and to reveal amino acid residues involved in substrate and cofactor binding. The carboxylate group of Trp interacts with $Arg^{257}$ and $Asp^{269}$, while the Trp side chain is held in a hydrophobic pocket formed by $Pro^{268}$, $His^{272}$, $Phe^{313}$ and $Phe^{318}$. The co-substrate $BH_4$ interacts with $Phe^{241}$ and $Glu^{273}$. Ligands to the non-heme iron ($Fe^{2+}$) are $His^{272}$, $His^{277}$ and $Glu^{317}$ are referred to as the 2-His-1-carboxylate facial triad. The general catalytic mechanism involves the iron-mediated incorporation of one atom of molecular oxygen into both the Trp substrate and the reducing co-substrate $BH_4$, yielding a hydroxylated product. This reaction is subdivided in three different steps, starting with the formation of an iron-peroxypterin and followed by its decay to a reactive intermediate and subsequent Trp hydroxylation via electrophilic aromatic substitution.

A variety of diseases are associated with a dysregulation of serotonin synthesis and metabolism. One example is carcinoid syndrome, a collection of symptoms resulting from an excessive release of hormones by carcinoid tumors. Carcinoid tumors develop from enterochromaffin cells, which produce serotonin, dopamine, tachykinins, and other substances that can have profound effects on the circulatory system, the gastrointestinal tract, and the lungs. Other serotonin-related cancer diseases comprise cholangiocarcinoma and neuroendocrine (N E) cancers, such as carcinoids and pancreatic endocrine tumors, prostate cancer.

A number of documents addresses compounds capable of influencing the serotonin level, in particular by inhibiting TPH (e.g. WO 2011/100285 A1, US 2009/0048280 A, WO 2010/003997 A1, US 2009/0088447 A1). The structures disclosed in WO 2011/100285 neither comprise a xanthine moiety nor a benzimidazolyl group.

However, because serotonin targets multiple receptors and is involved in so many biochemical processes, drugs that interfere with serotonin signalling are often attended by adverse effects. Thus, a need exists for new methods of affecting serotonin levels.

Lei Zhang et al. ("Discovery of Novel Vascular Endothelial Growth Factor Receptor 2 Inhibitors: A Virtual Screening Approach"; Chem. & Biol. Drug Des. 80 (2012), p. 893-901) disclose a benzimidazolyl xanthine derivative with potential use as inhibitor for vascular endothelial growth factor 2.

Henrik Frandsen et al. ("N-acetyltransferase-dependent activation of 2-hydroxyamino-1-methyl-6-phenylimidazo[4,5-b]pyridine: formation of 2-amino-1-methyl-6-(5-hydroxy) phenylimidazo[4,5-b]pyridine, a possible biomarker for the reactive dose of 2-amino-1-methyl-6-phenylimidazo[4,5-b] pyridine"; Carcinogenetics 21, 6 (2000), p. 1197-1203) describe a hydroxylated derivative of 2-amino-1-methyl-6-phenylimidazo[4,5-b]pyridine (PhIP) as a urinary biomarker for PhIP. PhIP is known to be a mutagenic and carcinogenic heterocyclic amine formed during frying of meat.

BRIEF DESCRIPTION OF THE INVENTION

The present invention, according to a first aspect, is directed to xanthine derivatives defined by chemical Formula I or a salt thereof:

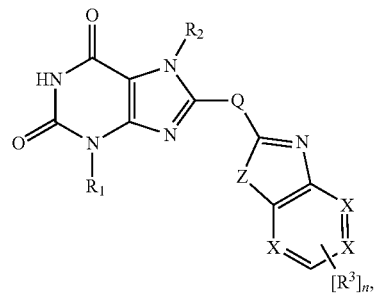

(I)

wherein $R^1$ and $R^2$ are each an optionally substituted group independently selected from hydrogen (—H), (C1-C10)-alkyl, (C2-C10)-alkenyl, (C2-C10)-alkynyl, (C5-C14)-aryl, (C5-C14)-heteroaryl, (C6-C15)-alkyl-aryl, (C6-C15)-alkyl-heteroaryl, (C6-C15)-alkenyl-aryl, (C6-C15)-alkenyl-heteroaryl, (C6-C15)-alkynyl-aryl, (C6-C15)-alkynyl-heteroaryl, (C6-C15)-aryl-alkylene, (C6-C15)-heteroaryl-alkylene, (C6-C15)-aryl-alkenylene, (C6-C15)-heteroaryl-alkenylene, (C6-C15)-aryl-alkylylene and (C6-C15)-heteroaryl-alkylylene, wherein the alkyl, alkenyl, alkynyl, alkylene, alkylene and alkenylene groups optionally comprise one or more bivalent groups substituting a carbon moiety in their hydrocarbon chain and selected from —O—, —S—, —S(O)—, —SO$_2$—, —N═, —N(R)—, —C(O)—, —C(O)O—, —OC(O)—, —C(O)N(R)—, —N(R)C(O)—, —OC(O)N(R)—, —N(R)C(O)O—, —N(R)C(O)N(R)—, (C3-C12)-heterocyclic alkylene and (C3-C12)-heterocyclic alkenylene;

$R^3$ means a number of n groups independently selected from hydrogen (—H), fluoro (—F), bromo (—Br), chloro (—Cl), hydroxyl (—OH), carbonyl (—C(O)R), carboxyl (—C(O)OH), carboxy ester (—CO$_2$R), alkoxy (—OR), aldehyde (—C(O)H), trihalide methyl ester (—OCX$_3$), primary, secondary and tertiary amine (—NR(R')), amide (—N(R)—C(O)—R), imide (—C(O)—N(R)—C(O)—R'), carbamate (—N(R)—C(O)—OR'), carboxamide (—C(O)N(R)R'), carbimide (—N(R)—C(O)—N(R')R''), primary and secondary ketimine (—(R)═NR'), secondary ketimine (—(R)═NH), nitrile (—CN), isonitrile (—NC), nitroxy (—ONO), nitro (—NO$_2$), nitrate (—ONO$_2$), nitroso (—NO), cyanate (—OCN), isocyanate (—NCO), sulfhydryl (—SH), sulfide (—SR), sulfurtrihalide (—SX$_3$), sulfurpentahalide (—SX$_5$), sulfinyl (—S(O)R), sulfonyl (—SO$_2$R), sulfino (—SO$_2$H), and sulfo (—SO$_3$H), and an optionally substituted and optionally linked group selected from (C1-C10)-alkyl, (C2-C10)-alkenyl, (C2-C10)-alkynyl, (C5-C14)-aryl, (C5-C14)-heteroaryl, (C6-C15)-alkyl-aryl, (C6-C15)-alkyl-heteroaryl, (C6-C15)-alkenyl-aryl, (C6-C15)-alkenyl-heteroaryl, (C6-C15)-alkynyl-aryl, (C6-C15)-alkynyl-heteroaryl, (C6-C15)-aryl-alkylene, (C6-C15)-heteroaryl-alkylene, (C6-C15)-aryl-alkenylene, (C6-C15)-heteroaryl-alkenylene, (C6-C15)-aryl-alkylylene and (C6-C15)-heteroaryl-alkylylene, wherein the alkyl, alkenyl, alkynyl, alkylene, alkylene and alkenylene groups optionally comprise one or more bivalent groups substituting a carbon moiety in their hydrocarbon chain and selected from —O—, —S—, —S(O)—, —SO$_2$—, —N═, —N(R)—, —C(O)—, —C(O)O—, —OC(O)—, —C(O)N(R)—, —N(R)C(O)—, —OC(O)N(R)—, —N(R)C(O)O—, —N(R)C(O)N(R)—, (C3-C12)-heterocyclic alkylene or alkenylene;

Q is selected from methylene (—C(R)H—), amino (—N(R)—) and sulfide (—S—);

X is selected from carbon (—C—) and nitrogen (—N—);

Z is selected from amino (—NH—), oxygen (—O—) and sulfur (—S—); and n is a number selected from 1, 2 and 3;

wherein in the aforementioned definitions R, R' and R" independently mean hydrogen, (C1-C3)-alkyl or (C2-C3)-alkenyl.

The xanthine derivatives according to the present invention show a strong inhibiting effect of tryptophan hydroxylases TPH1 and/or TPH2 involved in the biosynthesis of serotonin. Thus, the xanthine derivatives according to the present invention can be used for the treatment of diseases or disorders, that are related to the level of serotonin in the human or animal body. In other words, the xanthine derivatives of the invention can be used to modulate the serotonin level in the body or in specific organs. Particular examples of the xanthine derivatives of the invention show a selective inhibition of TPH2 only. These compounds are thus suitable for the treatment of diseases related to the serotonin synthesized by cells or organs expressing TPH2. Other examples of the xanthine derivatives of the invention exhibit molecular properties which restrict their passage through the blood brain barrier. Because TPH2 is solely expressed in the brainstem these compounds are not able to target TPH2. Instead, these compounds are thus suitable for the treatment of diseases related to the serotonin synthesized by cells or organs expressing TPH1.

Another aspect of the present invention is directed to a xanthine derivative according to chemical Formula I as defined herein for use as a medicament.

Another aspect of the present invention is directed to a xanthine derivative according to chemical Formula I as defined herein for use in the treatment of serotonin-related diseases or serotonin-related disorders.

Another aspect of the present invention is directed to the use of a xanthine derivative according to chemical Formula I as defined herein in the treatment of serotonin-related diseases or disorders.

Yet another aspect of the present invention is directed to the use of a xanthine derivative according to chemical Formula I as defined herein in the manufacture of a medicament for the treatment of serotonin-related diseases or disorders.

Yet another aspect of the present invention is directed to a method of treatment of serotonin-related diseases or disorders, wherein the subject of need thereof is administered an effective amount of a xanthine derivative according to chemical Formula I as defined herein.

Another aspect of the present invention is directed to a pharmaceutical preparation comprising the xanthine derivative according to chemical Formula I as defined herein or a pharmaceutical acceptable salt thereof.

Serotonin-related diseases and disorders that can be treated with the xanthine derivatives according to the present invention comprise, for instance, TPH1-specific diseases and disorders:

Serotonin syndrome.

Bone diseases: osteoporosis, osteoporosis-pseudoglioma syndrome (OPPG), osteopenia, osteogenesis imperfecta, osteomalacia, renal osteodystrophy, faulty bone formation or resorption, Paget's disease, fractures and broken bones, bone metastasis.

Immunological diseases: systemic sclerosis, transplant rejection.

Pulmonary diseases: chronic obstructive pulmonary disease (COPD), pulmonary hypertension, asthma.

Gastrointestinal diseases: abdominal pain, carcinoid syndrome, celiac disease, constipation, Crohn's disease, diarrhea, emesis, anorectal disorders, bloating, dyspepsia, gallbladder disorders, irritable bowel syndrome, lactose intolerance, MEN types I and II, nausea, Ogilvie's syndrome, pancreatic insufficiency, somatization disorder, sphincter of Oddi disorders, ulcerative colitis, Zollinger-Ellison Syndrome.

Cancer: carcinoid tumours, pheochromocytoma, carcinoma of prostate, lung, bladder, intestine, breast, liver and ovary.

Vascular diseases: thrombosis, atherosclerosis, aortic aneurysm, coronary artery disease, peripheral artery disease, CREST syndrome (calcinosis, Raynaud's phenomenon, esophageal dysfunction, sclerodactyly), telangiectasia), migraine.

Inflammatory diseases: pancreatitis, hepatitis, asthma.

Metabolic diseases: non-alcoholic fatty liver disease, obesity, diabetes, metabolic syndrome.

Serotonin-related diseases and disorders that can be treated with the xanthine derivatives according to the present invention comprise, for instance, TPH2-specific diseases and disorders:

Psychiatric diseases: major depression, bipolar disorder, schizophrenia, hypoactive sexual desire disorder.

Accordingly, the xanthine derivative of Formula I according to the present invention may be used in the treatment of serotonin-related diseases or disorders comprising serotonin syndrome, osteoporosis, osteoporosis-pseudoglioma syndrome (OPPG), osteopenia, osteogenesis imperfecta, osteomalacia, renal osteodystrophy, faulty bone formation or resorption, Paget's disease, fractures and broken bones, bone metastasis; systemic sclerosis, transplant rejection; chronic obstructive pulmonary disease (COPD), pulmonary hypertension, asthma; abdominal pain, carcinoid syndrome, celiac disease, constipation, Crohn's disease, diarrhea, emesis, anorectal disorders, bloating, dyspepsia, gallbladder disorders, irritable bowel syndrome, lactose intolerance, MEN types I and II, nausea, Ogilvie's syndrome, pancreatic insufficiency, somatization disorder, sphincter of Oddi disorders, ulcerative colitis, Zollinger-Ellison Syndrome; carcinoid tumours, pheochromocytoma, carcinoma of prostate, lung, bladder, intestine, breast, liver and ovary; thrombosis, atherosclerosis, aortic aneurysm, coronary artery disease, peripheral artery disease, CREST syndrome (calcinosis, Raynaud's phenomenon, esophageal dysfunction, sclerodactyly), telangiectasia), migraine; pancreatitis, hepatitis, asthma; non-alcoholic fatty liver disease, obesity, diabetes, metabolic syndrome; major depression, bipolar disorder, schizophrenia and hypoactive sexual desire disorder.

According to specific embodiments, the xanthine derivative of the invention is used in the treatment of at least one of the following diseases or disorders selected from pulmonary hypertension, carcinoid syndrome, irritable bowel syndrome, thrombosis, osteoporosis, pancreatitis, hepatitis, non-alcoholic fatty liver disease, obesity, systemic sclerosis, transplant rejection, and major depression.

Xanthine Derivatives

Xanthine derivatives defined by chemical Formula I according to the present invention comprise any of their stereoisomeric forms, if any, and mixtures of stereoisomeric forms in any ratio.

The xanthine derivative may exist as a salt, preferably, a pharmaceutically acceptable salt. Pharmaceutically acceptable salts comprise inorganic acid salts such as chlorides, hydrochlorides, sulfates, bisulfates, nitrates, hydrobromides, hydroiodides and phosphates; organic carboxylates such as acetates, lactates, citrates, oxalates, glutarates, malates, tartrates, bitartrates, fumarates, mandelates, maleates, succinates, benzoates and phthalates; organic sulfonates such as methanesulfonates, ethansulfonates, benzenesulfonates, p-toluenesulfonates and camphor-sulfonates.

In Formula I, X is preferably carbon. More preferably, each of X is carbon.

In Formula I, Z is preferably an amino group —NH—.

In particular preferred embodiments, X is carbon and Z is an amino group —NH—. When X is carbon and Z is an amino group, the aromatic moiety in Formula I is benzimidazolyl.

In Formula I, Q may be a methylene group —C(R)H—, preferably —CH$_2$—.

Alternatively, Q may be a sulphide group —S—.

In Formula I, $R^1$ bound to the nitrogen atom at position 3 of the xanthine moiety, is optionally substituted group independently selected from hydrogen (—H), (C1-C10)-alkyl, (C2-C10)-alkenyl, (C2-C10)-alkynyl, (C5-C14)-aryl, (C5-C14)-heteroaryl, (C6-C15)-alkyl-aryl, (C6-C15)-alkyl-heteroaryl, (C6-C15)-alkenyl-aryl, (C6-C15)-alkenyl-heteroaryl, (C6-C15)-alkynyl-aryl, (C6-C15)-alkynyl-heteroaryl, (C6-C15)-aryl-alkylene, (C6-C15)-heteroaryl-alkylene, (C6-C15)-aryl-alkenylene, (C6-C15)-heteroaryl-alkenylene, (C6-C15)-aryl-alkylylene and (C6-C15)-heteroaryl-alkylylene, wherein the alkyl, alkenyl, alkynyl, alkylene, alkylene and alkenylene groups optionally comprise one or more bivalent groups substituting a carbon moiety in their hydrocarbon chain and selected from —O—, —S—, —S(O)—, —SO$_2$—, —N=, —N(R)—, —C(O)—, —C(O)O—, —OC(O)—, —C(O)N(R)—, —N(R)C(O)—, —OC(O)N(R)—, —N(R)C(O)O—, —N(R)C(O)N(R)—, (C3-C12)-heterocyclic alkylene and (C3-C12)-heterocyclic alkenylene.

More specifically, $R^1$ may be an optionally substituted group independently selected from (C1-C7)-alkyl, (C2-C7)-alkenyl, (C2-C7)-alkynyl, (C5-C10)-aryl, (C5-C10)-heteroaryl, (C6-C10)-alkyl-aryl, (C6-C10)-alkyl-heteroaryl, (C6-C10)-alkenyl-aryl, (C6-C10)-alkenyl-heteroaryl, (C6-C10)-alkynyl-aryl, (C6-C10)-alkynyl-heteroaryl, (C6-C10)-aryl-alkylene, (C6-C10)-heteroaryl-alkylene, (C6-C10)-aryl-alkenylene, (C6-C10)-heteroaryl-alkenylene, (C6-C10)-aryl-alkylylene and (C6-C10)-heteroaryl-alkylylene, wherein the alkyl, alkenyl, alkynyl, alkylene, alkylene and alkenylene groups optionally comprise one or more bivalent groups as defined above.

Particularly preferred bivalent groups for $R^1$ comprise —O—, —N(R)—, —C(O)—, —C(O)O—, —OC(O)— (C3-C6)-heterocyclic alkylene and (C3-C6)-heterocyclic alkenylene.

According to particular embodiments, $R^1$ is selected from an optionally substituted linear, branched or cyclic (C1-C5)-alkyl group. According to specific examples $R^1$ is selected from the group consisting of methyl, ethyl, n-propyl, isopropyl, cyclopropyl, cyclobutyl and cyclopentyl.

In Formula I, $R^2$ bound to the nitrogen atom at position 7 of the xanthine moiety, is optionally substituted group independently selected from hydrogen (—H), (C1-C10)-alkyl, (C2-C10)-alkenyl, (C2-C10)-alkynyl, (C5-C14)-aryl, (C5-C14)-heteroaryl, (C6-C15)-alkyl-aryl, (C6-C15)-alkyl-heteroaryl, (C6-C15)-alkenyl-aryl, (C6-C15)-alkenyl-heteroaryl, (C6-C15)-alkynyl-aryl, (C6-C15)-alkynyl-heteroaryl, (C6-C15)-aryl-alkylene, (C6-C15)-heteroaryl-alkylene, (C6-C15)-aryl-alkenylene, (C6-C15)-heteroaryl-alkenylene, (C6-C15)-aryl-alkylylene and (C6-C15)-heteroaryl-alkylylene, wherein the alkyl, alkenyl, alkynyl, alkylene, alkylene and alkenylene groups optionally comprise one or more bivalent groups substituting a carbon moiety in their hydrocarbon chain and selected from —O—, —S—, —S(O)—, —SO$_2$—, —N=, —N(R)—, —C(O)—, —C(O)O—, —OC(O)—, —C(O)N(R)—, —N(R)C(O)—, —OC(O)N(R)—, —N(R)C(O)O—, —N(R)C(O)N(R)—, (C3-C12)-heterocyclic alkylene and (C3-C12)-heterocyclic alkenylene.

More specifically, $R^2$ may be an optionally substituted group independently selected from (C1-C7)-alkyl, (C2-C7)-alkenyl, (C2-C7)-alkynyl, (C5-C10)-aryl, (C5-C10)-heteroaryl, (C6-C10)-alkyl-aryl, (C6-C10)-alkyl-heteroaryl, (C6-C10)-alkenyl-aryl, (C6-C10)-alkenyl-heteroaryl, (C6-C10)-alkynyl-aryl, (C6-C10)-alkynyl-heteroaryl, (C6-C10)-aryl-alkylene, (C6-C10)-heteroaryl-alkylene, (C6-C10)-aryl-alkenylene, (C6-C10)-heteroaryl-alkenylene, (C6-C10)-aryl-alkylylene and (C6-C10)-heteroaryl-alkylylene, wherein the alkyl, alkenyl, alkynyl, alkylene, alkylene and alkenylene groups optionally comprise one or more bivalent groups as defined above.

Preferably, $R^2$ comprises an aryl or a heteroaryl group.

Even more specifically, $R^2$ may be selected from an optionally substituted group selected from (C5-C12)-aryl, (C5-C12)-heteroaryl, (C6-C12)-alkyl-aryl, (C6-C12)-alkyl-heteroaryl, (C6-C12)-alkenyl-aryl, (C6-C12)-alkenyl-heteroaryl, (C6-C12)-alkynyl-aryl, (C6-C12)-alkynyl-heteroaryl, (C6-C12)-aryl-alkylene, (C6-C12)-heteroaryl-alkylene, (C6-C12)-aryl-alkenylene, (C6-C12)-heteroaryl-alkenylene, (C6-C12)-aryl-alkylylene and (C6-C12)-heteroaryl-alkylylene. According to an even more specific embodiment $R^2$ is selected from an optionally substituted (C6-C8)-aryl-alkylene and (C6-C8)-heteroaryl-alkylene.

Particularly preferred bivalent groups for $R^2$ comprise —O—, —N=, —N(R)—, —C(O)—, —C(O)O—, —OC(O)—, —C(O)N(R)—, —N(R)C(O)—, (C3-C6)-heterocyclic alkylene and (C3-C6)-heterocyclic alkenylene.

$R^2$ may be a group defined by chemical Formula Ia:

$$—R^5—Ar \qquad (Ia),$$

wherein $R^5$ is (C0-C3)-alkylene, and Ar is an optionally substituted (C5-C12)-aryl or (C5-C12)-heteroaryl.

In Formula Ia, Ar is preferably (C5-C6)-aryl or (C5-C6)-heteroaryl. Particular preferred groups are selected from pyrrole, pyrazole, imidazole, triazole, tetrazole, pentazole, furane, such as furan-2-yl or furan-3-yl; oxazole, such as 1,3-oxazole-2-yl or 1,3-oxazole-5-yl; isoxazole (=1,2-oxazole), such as 1,2-oxazole-3-yl, 1,2-oxazole-4-yl or 1,2-oxazole-5-yl; oxadiazole, such as 1,3,4-oxadiazole-2-yl or 1,2,4-oxadiazole-3-yl; thiophene, such as thiophene-2-yl or thiophene-3-yl; thiazole, such as 1,3-thiazole-2-yl or 1,3-thiazole-5-yl; isothiazole (=1,2-thiazole), such as 1,2-thiazole-3-yl, 1,2-thiozole-4-yl or 1,2-thiazole-5-yl; thiadiazole, such as 1,2,4-thiadiazole or 1,3,4-thiadiazole, pyridine, 1,2-diazine, 1,3-diazine (pyrimidine), 1,4-diazine (pyrazine), 1,2,3-trazine, 1,2,4-trazine, 1,3,5-triazine, 1,2,3,4-tetrazine, 1,2,3,5-tetrazine, 1,2,4,5-tetrazine.

Preferred substituents of the Ar in Formula Ia moiety comprise (C1-C3)-alkyl, a primary, secondary or tertiary amino group —N(R)R' such as —NH$_2$, an amide group —NH—C(O)—R, such as acetamide —NH—C(O)CH$_3$, and a (C5-C6)-heterocyclic group, such as morpholino, in particular morpholin-4-yl.

Further in Formula Ia, $R^5$ is preferably a methylene group —CH$_2$—.

According to a specific embodiment, optionally substituted benzyl —CH$_2$—C$_6$H$_5$ is particular preferred as group R². In many cases, unsubstituted benzyl may be used as R². However, in some cases a substituted benzyl is used. This is especially useful, when selective inhibition of TPH2 is desired.

Preferred substituents of R², in particular for benzyl, comprise a (C1-C3)-alkyl group, a primary, secondary or tertiary amino group —N(R)R' such as —NH₂, an amide group —NH—C(O)—R, such as acetamide —NH—C(O) CH₃, and a (C5-C6)-heterocyclic group, such as morpholino, in particular morpholin-4-yl.

Alternatively, R² is an optionally substituted (C5-C6)-aryl-methylene or (C5-C6)-heteroaryl-methylene, where the (C5-C6)-(hetero)aryl group is selected from those mentioned above. This is especially advantageous when selective inhibition of TPH2 is desired.

According to a preferred embodiment, at least one of R¹ and R² in Formula I is not hydrogen; even more preferred both of R¹ and R² are not hydrogen.

In Formula I, R³ means a number of n groups independently selected from hydrogen (—H), fluoro (—F), bromo (—Br), chloro (—Cl), hydroxyl (—OH), carbonyl (—C(O) R), carboxyl (—C(O)OH), carboxy ester (—CO₂R), alkoxy (—OR), aldehyde (—C(O)H), trihalide methyl ester (—OCX₃), primary, secondary and tertiary amine (—NR (R')), amide (—N(R)—C(O)—R), imide (—C(O)—N(R)—C(O)—R'), carbamate (—N(R)—C(O)—OR'), carboxamide (—C(O)N(R)R'), carbimide (—N(R)—C(O)—N(R')R"), primary and secondary ketimine (—(R)=NR'), secondary ketimine (—(R)=NH), nitrile (—CN), isonitrile (—NC), nitroxy (—ONO), nitro (—NO₂), nitrate (—ONO₂), nitroso (—NO), cyanate (—OCN), isocyanate (—NCO), sulfhydryl (—SH), sulfide (—SR), sulfurtrihalide (—SX₃), sulfurpentahalide (—SX₅), sulfinyl (—S(O)R), sulfonyl (—SO₂R), sulfino (—SO₂H), and sulfo (—SO₃H), and an optionally substituted and optionally linked group selected from (C1-C10)-alkyl, (C2-C10)-alkenyl, (C2-C10)-alkynyl, (C5-C14)-aryl, (C5-C14)-heteroaryl, (C6-C15)-alkyl-aryl, (C6-C15)-alkyl-heteroaryl, (C6-C15)-alkenyl-aryl, (C6-C15)-alkenyl-heteroaryl, (C6-C15)-alkynyl-aryl, (C6-C15)-alkynyl-heteroaryl, (C6-C15)-aryl-alkylene, (C6-C15)-heteroaryl-alkylene, (C6-C15)-aryl-alkenylene, (C6-C15)-heteroaryl-alkenylene, (C6-C15)-aryl-alkylylene and (C6-C15)-heteroaryl-alkylylene, wherein the alkyl, alkenyl, alkynyl, alkylene, alkylene and alkenylene groups optionally comprise one or more bivalent groups as mentioned above.

R³ may be present is any number of 1, 2, and 3 and may be bound to any of positions 3, 4, 5, and 6 of the C6-aryl moiety (numbered with respect to the benzodiazol derivative moiety). Preferably R³ is bound to the 5 or 6 position of the ring system in formula I. According to particular embodiments, two groups of R³ are bound to the 5 and 6 positions of the benzimidazolyl ring system. In this case, the two R³ groups may be linked together as to form a cyclic group, particularly by a single C—C-bond.

In fact, the nature of R³ appears to be highly variable without adversely affecting the inhibitory effect of the xanthine derivative towards TPH. Thus, R³ may be a hydrophilic group, especially a polar group or a charged group, in order to increase the solubility of the compound in polar solvents, such as water.

In Formula I, R³ is preferably selected from hydrogen, fluorine, chlorine, bromine, amine, amide, carbonitrile, sulfonic acid, carboxylic acid, carboxy ester, optionally substituted (C1-C10)-alkyl, optionally substituted saturated or unsaturated (C5-C6)-heterocyclic, optionally substituted (C2-C10)-alkenyl, optionally substituted (C1-C5)-alkoxy, wherein the alkyl and alkenyl groups optionally comprise one or more bivalent groups as defined above.

Particularly preferred bivalent groups for R³ comprise oxygen —O—, amine —N(R)— or —NH—, amide —N(R)—C(O)— or —NH—C(O)—.

Preferred substituents of the alkyl, alkenyl and alkoxy groups of R³ comprise fluorine, chlorine, bromine, amine, sulfonic acid, carboxylic acid and carboxy ester.

Particularly preferred optionally substituted (C1-C10)-alkyl groups for R³ comprise (C1-C3)-alkyl groups, including methyl, ethyl, isopropyl, and n-propyl.

Particularly preferred optionally substituted (C5-C6)-heterocyclic groups for R³ comprise piperidine, such as piperidine-1-yl; piperazin, such as piperazin-1-yl or 4-(C1-C3)-alkyl-piperazin; morpholine, such as morpholine-4-yl.

Particularly preferred optionally substituted (C1-C5)-alkoxy groups for R³ comprise methoxy, ethoxy, n-propyloxy, isopropyloxy and 2-hydroxyethoxy.

Particularly preferred optionally substituted amide groups for R³ comprise (C1-C7)-alkyl-amides, such as acetamide, ethylamide, propylamide, butylamide, pentylamide. Substituted (C1-C7)-alkyl-amides comprise, for instance, carbamoyl propionic acid, carbamoyl butanoic acid, 2-amino-carbamoyl propionic acid and 2-amino-carbamoyl butanoic acid.

According to a specific embodiment, R³ is hydrogen.

Particular preferred xanthine derivatives according to the invention comprise the following compounds according to chemical Formulas (I-1) to (I-47), (I-201) to (I-211), and (I-301) to (I-303):

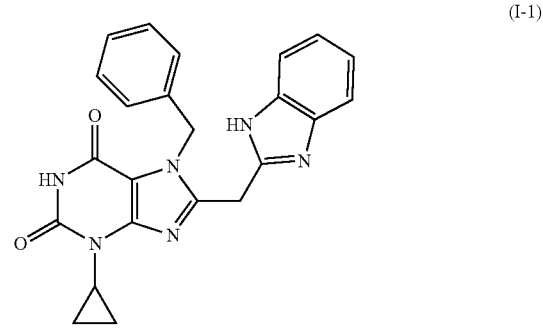

(I-1)

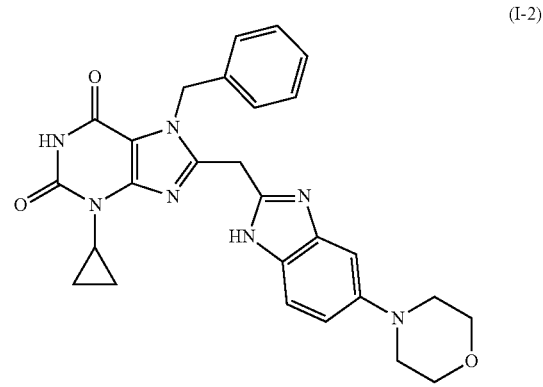

(I-2)

(I-3) 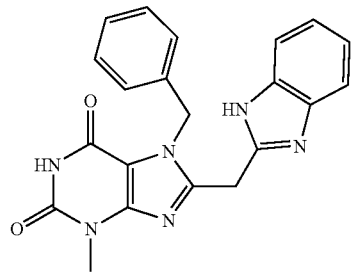
(I-4) 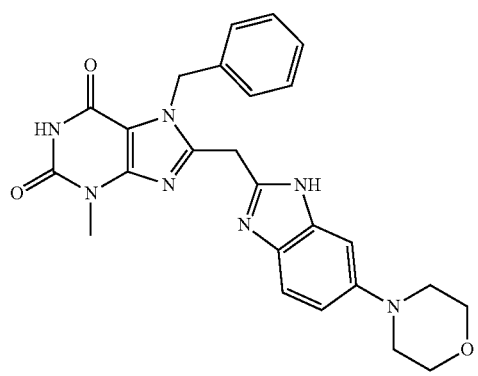
(I-5) 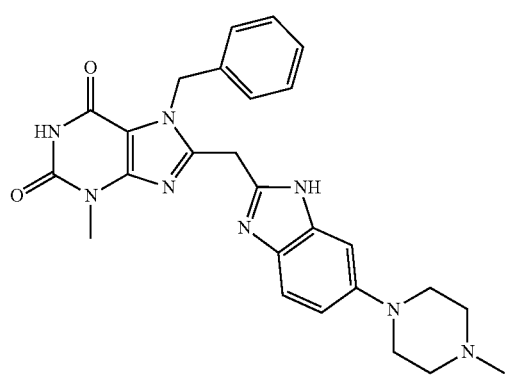
(I-6) 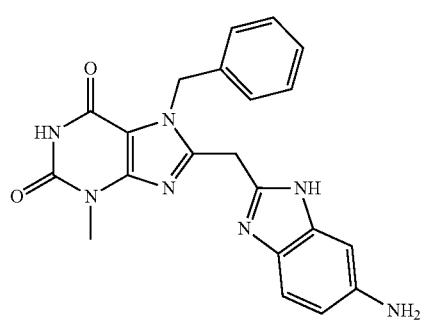
(I-7) 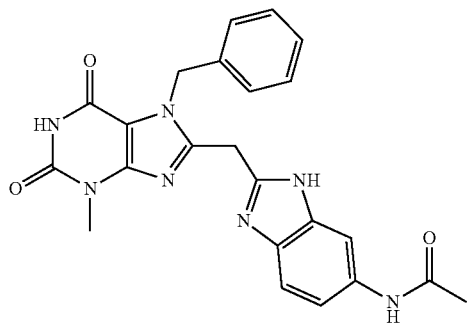
(I-8) 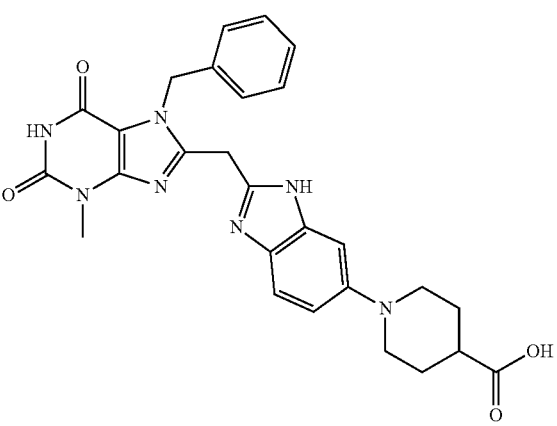
(I-9) 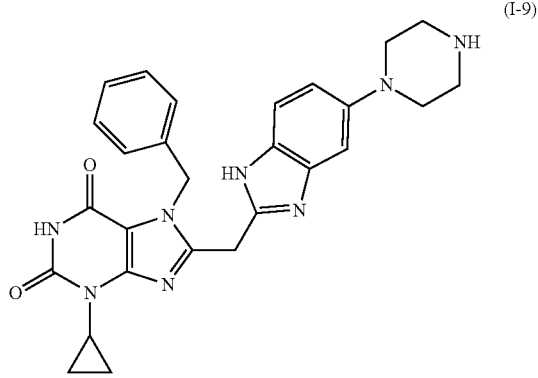
(I-10) 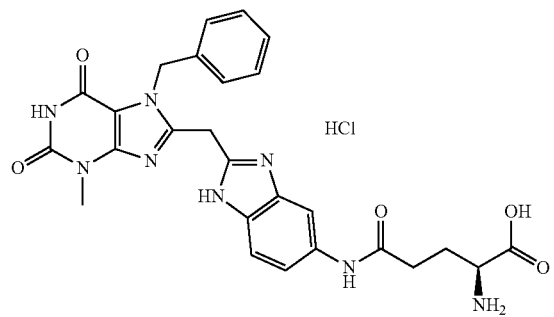

(I-11)
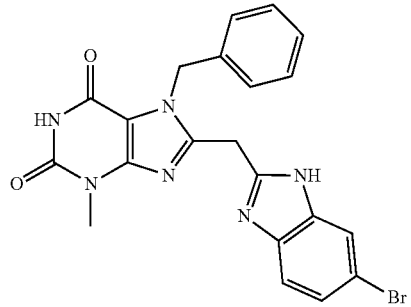
(I-12)
(I-13)
(I-14)
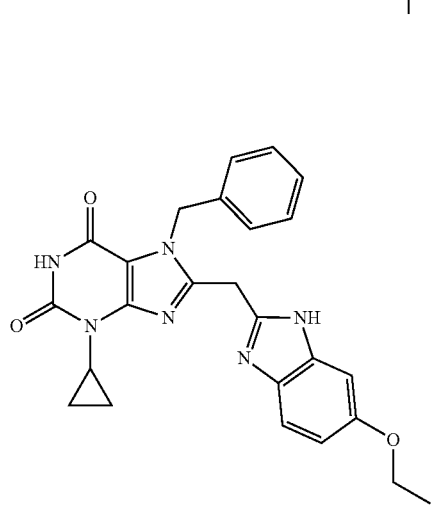
(I-15)
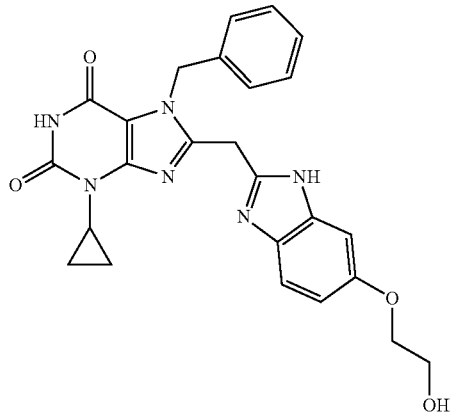
(I-16)
(I-17)
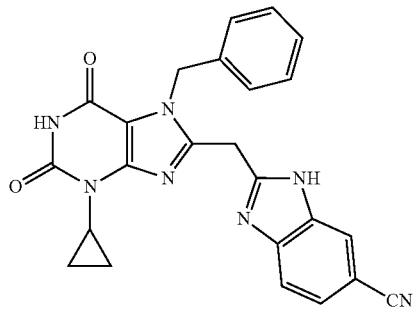
(I-18)
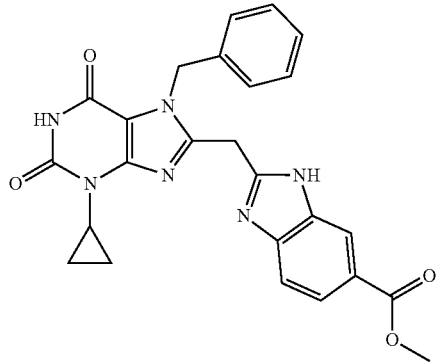

(I-19)
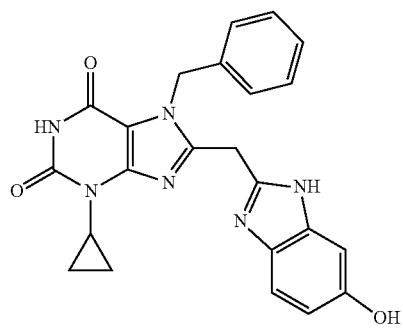
(I-20)
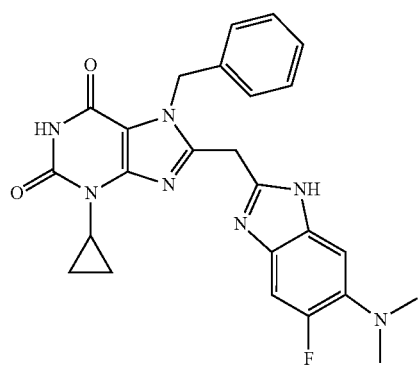
(I-21)
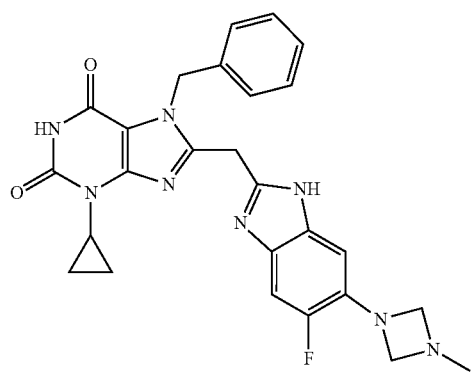
(I-22)
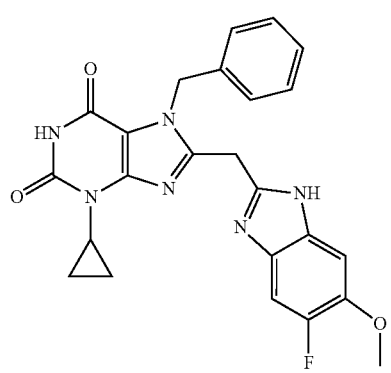
(I-23)
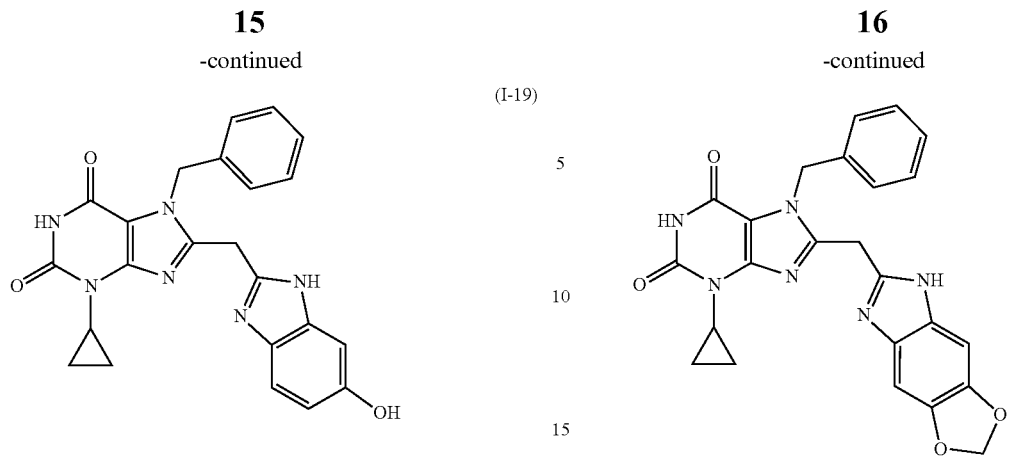
(I-201)
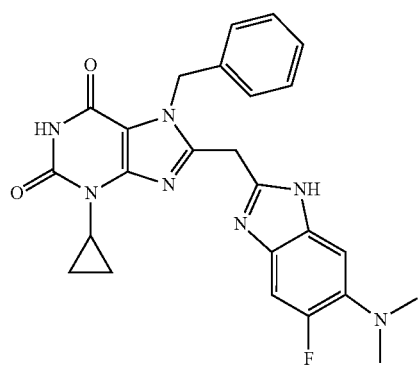
(I-202)
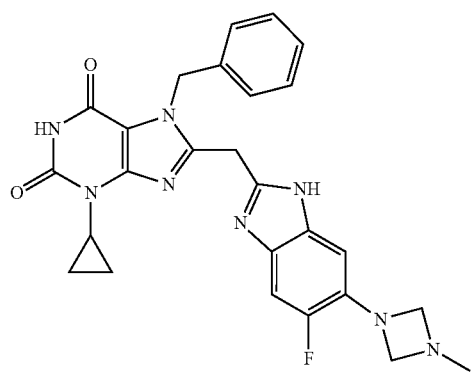
(I-203)
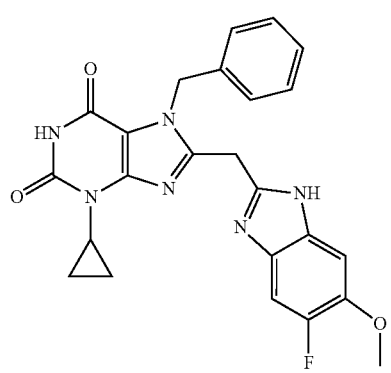

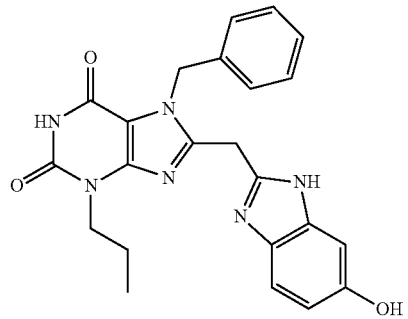
(I-204)
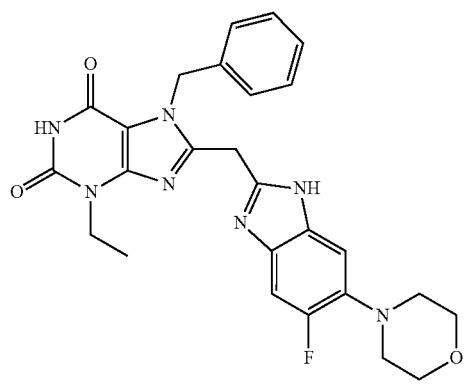
(I-205)
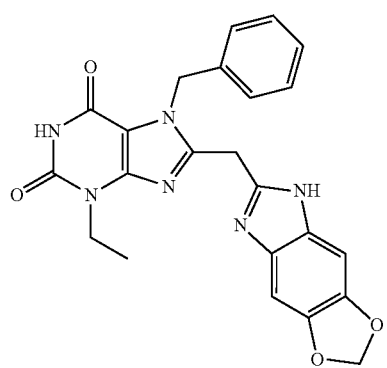
(I-206)
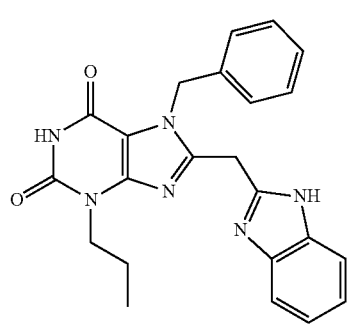
(I-207)
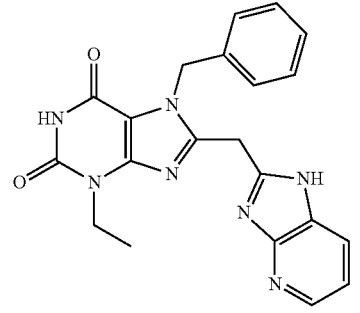
(I-208)
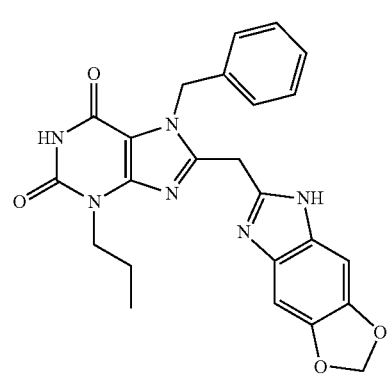
(I-209)
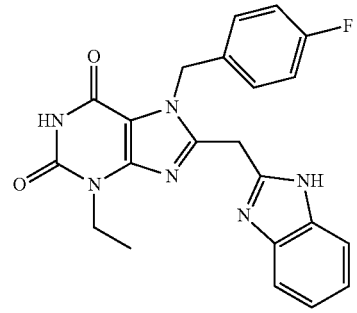
(I-210)
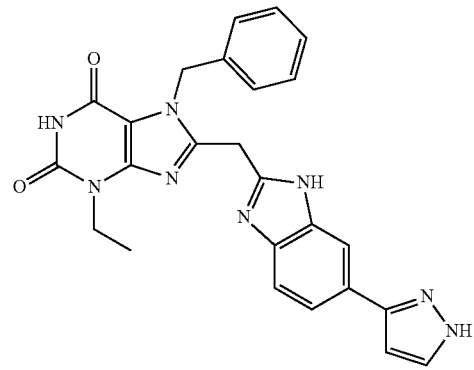
(I-211)

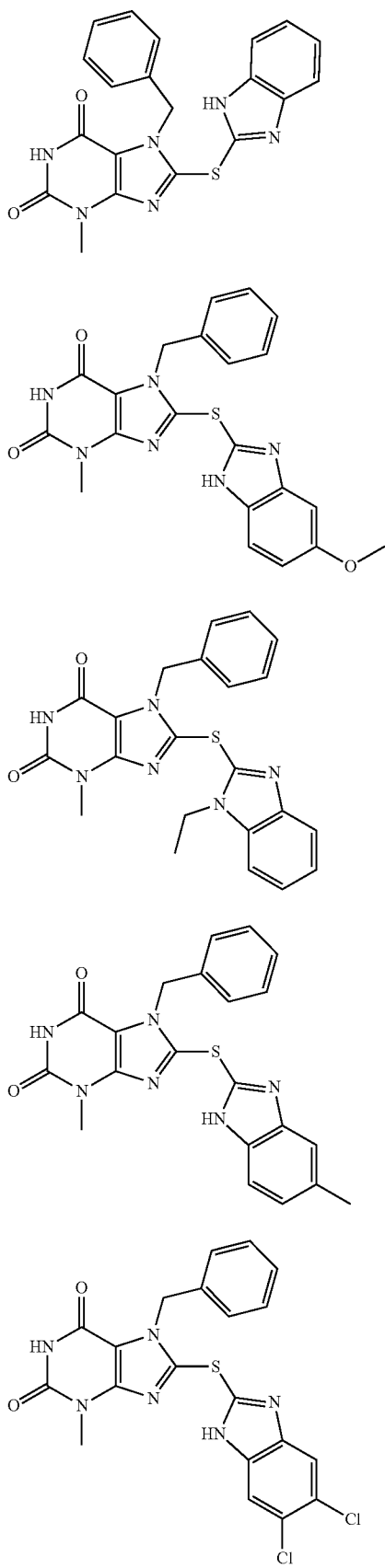
(I-24)
(I-25)
(I-26)
(I-27)
(I-28)
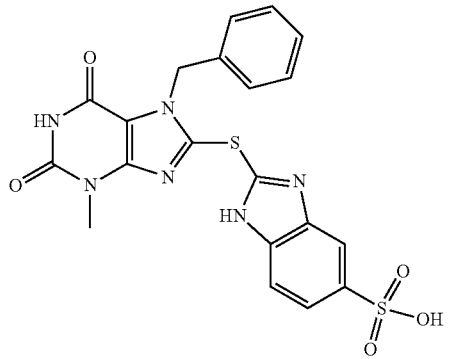
(I-29)
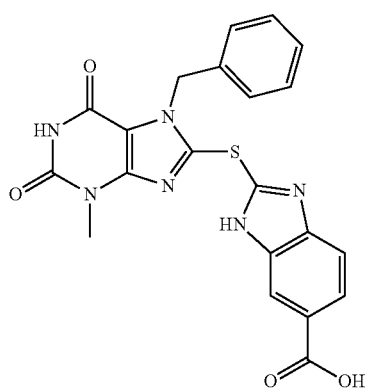
(I-30)
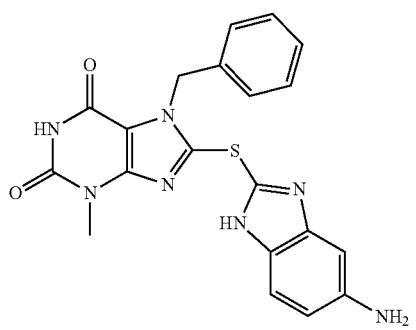
(I-31)
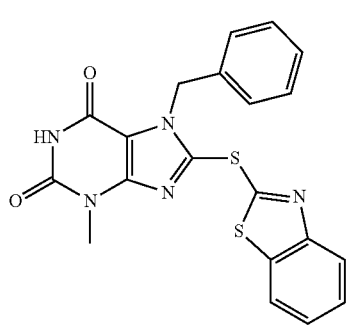
(I-32)

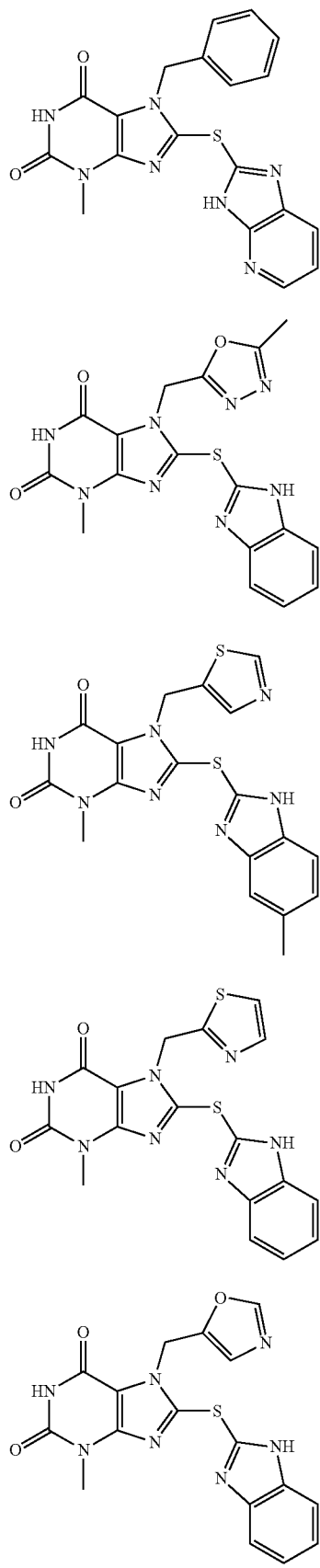
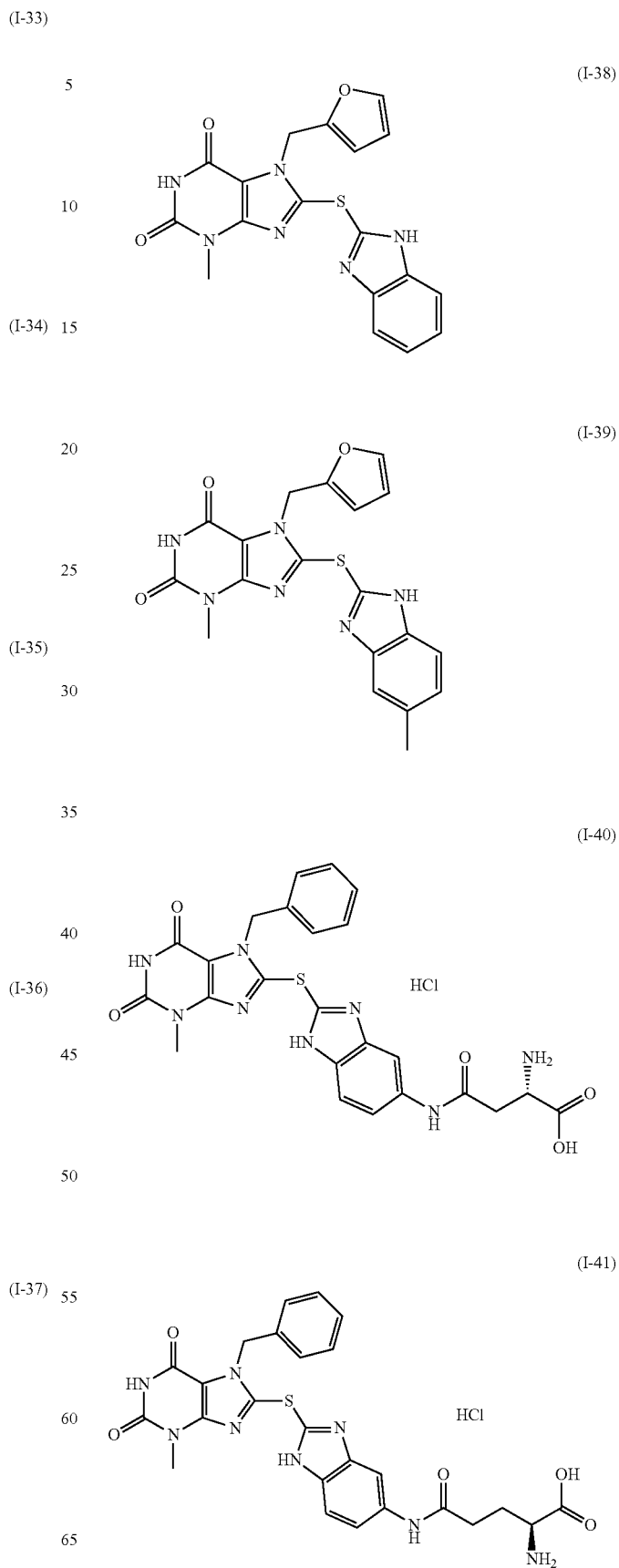

(I-42)
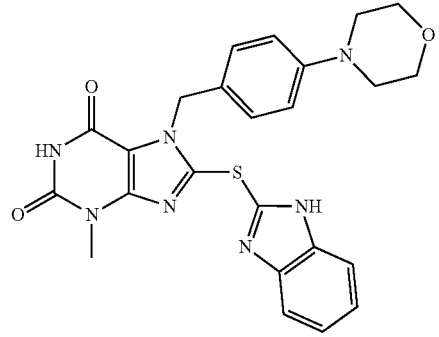
(I-43)
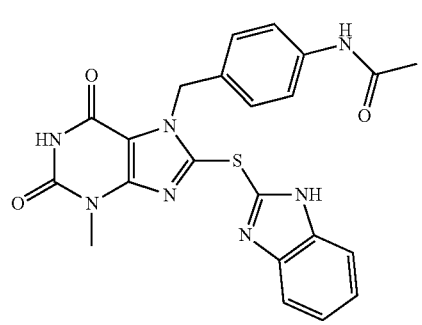
(I-44)
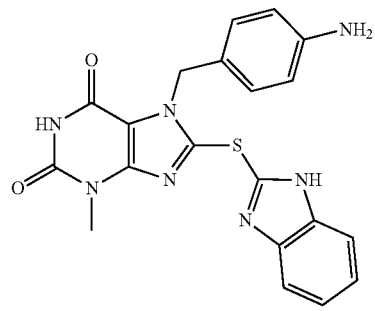
(I-45)
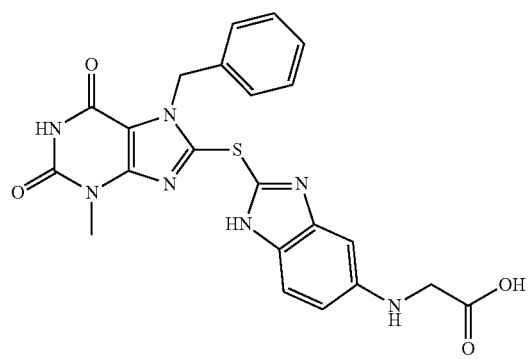
(I-46)
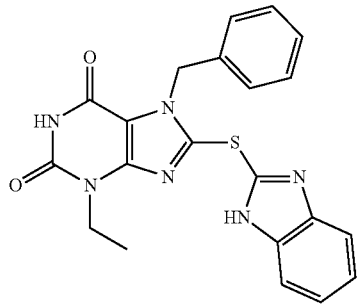
(I-47)
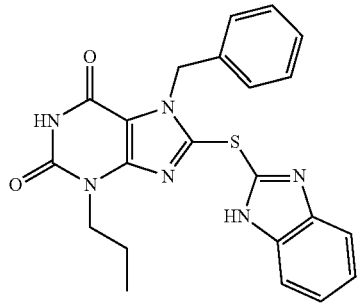
(I-301)
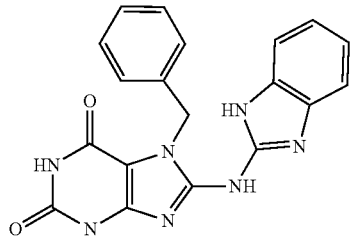
(I-302)
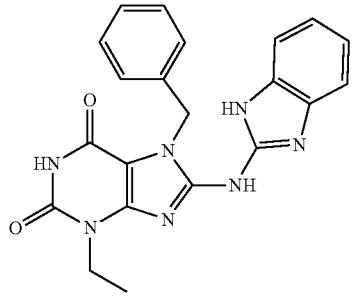
(I-303)
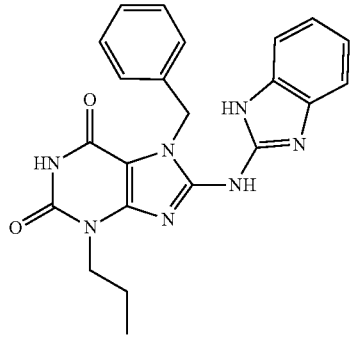
Preparation Process
Another subject of the present invention are processes for the preparation of the compounds of the formula I which are outlined below and by which the compounds of the formula I and intermediates in the course of their synthesis and salts thereof are obtainable. In general, the xanthine compounds of the formula I can be prepared, for example, in the course of a convergent synthesis, by linking two or more fragments which can be derived retrosynthetically from the formula I. More specifically, suitably substituted starting xanthines and benzimidazolyl-derivatives can be employed as building blocks in the preparation of the compounds of formula I, which can be synthesized from suitable precursor compounds, which allow the introduction of a variety of substituents into the various positions of the resulting xanthine derivatives system and which can be chemically modified further in order to finally arrive at the compound of the formula I having the desired substituent pattern. In the synthesis of the xanthine derivatives, use can also be made of procedures and transformations which are described in the literature with respect to xanthine and benzimidazole derivative preparation.

The starting materials employed in the synthesis of the compounds of the formula I are commercially available or can be prepared according to procedures, or in analogy to procedures, described in the literature or herein General Procedure A:

In one synthetic approach for the preparation of compounds of the formula I, a compound of the formula II and a compound of the formula III are reacted to give a compound of the formula IV, which can already be the final compound of the formula I, or which is converted into the desired final compound of the formula I.

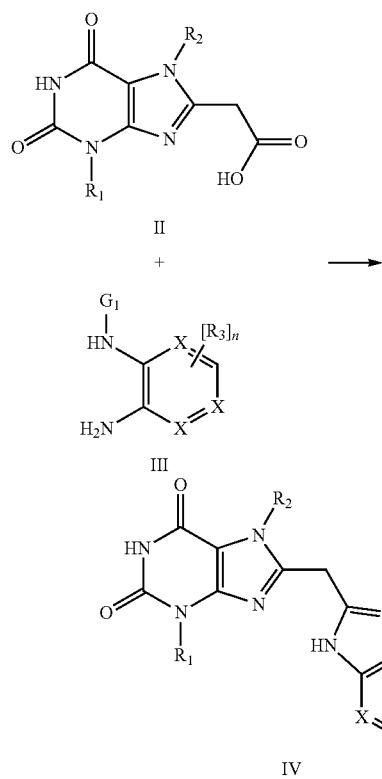

More specifically, for the preparation of the compound of formula II, a compound of the formula V is obtained by reacting a cyanate with a primary amine to give a urea which is converted to the compound of the formula V. The compound of the formula VI is obtained by reacting the compound of the formula V with cyano acetic acid. The compound of the formula II is obtained by reacting the compound of formula VI with a reagent R$_2$-G$_2$ and a base.

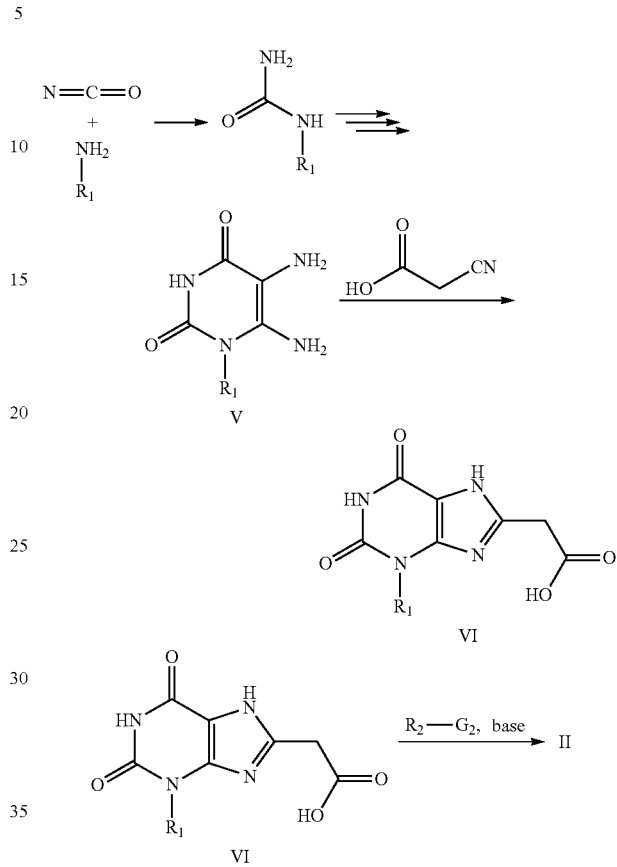

General Procedure B:

In an alternative synthetic approach for the preparation of compounds of the formula I, a compound of the formula VII and a compound of the formula VIII or X (where in VIII Q is —SH and in formula X Q is —N(R)H) are reacted to give a compound of the formula IX or XI (where in IX Q is —S— and in formula XI Q is —N(R)—), respectively, which can already be the final compound of the formula I, or which is converted into the desired final compound of the formula I.

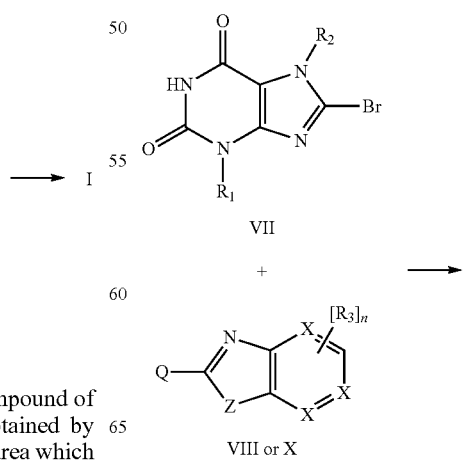

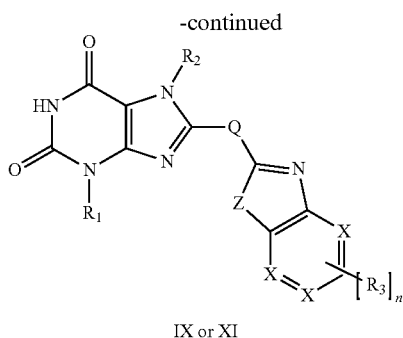

IX or XI

More specifically, in order to synthesize the compound of the formula VII, a compound of the formula V is converted with formic acid and bromine to bromo-xanthine XII. The compound of the formula VII is obtained by reacting with a reagent $R_2$-$G_2$ and a base.

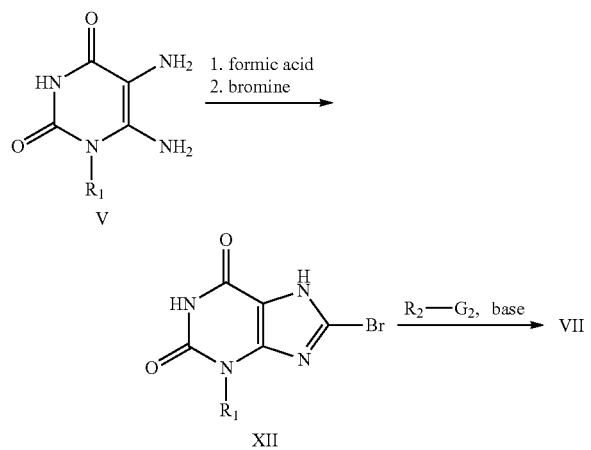

The groups $R_1$, $R_2$ and $R_3$, Z and X, and the number n in the compounds of the formulae II, III, IV, V, VII, X, XI and XII are defined as in the compounds of the formula I, and additionally can functional groups be present in protected form or in the form of a precursor group which is subsequently converted into the final group. The group $G_1$ in the compounds of the formula III is a protecting group for one of the amines. The group $G_2$ attached to residue $R_2$ is a leaving group, such as a halogen, in particular bromine or chlorine, or a sulfonyloxy group, in particular trifluoromethanesulfonyloxy, methanesulfonyloxy, benzenesulfonyloxy or tosyloxy.

The starting compounds in the synthesis of the compounds of the formula I can also be employed, and the intermediates obtained and/or employed, in the form of salts, for example acid addition salts in case of basic compounds. The intermediates can also be present in another tautomeric form.

The reaction of the compounds of the formulae II and III are, in general, extensively described in textbooks of peptide chemistry and synthesis.

The reaction of compounds of the formulae II with III and V with cyano acetic acid is generally carried out in an aprotic solvent such as a nitrile like acetonitrile, an ether like tetrahydrofuran or diglyme (di(2-methoxyethyl) ether), an amide like dimethylformamide, N-methylpyrrolidinone, dimethylacetamide, a sulfoxide like dimethylsulfoxide at temperatures from about 20° C. to about 200° C., for example at temperatures from about 30° C. to about 60° C. The reaction time generally is from about 30 minutes to about 48 hours, for example from about 5 hours to about 16 hours, depending on the particulars of the specific case and the chosen temperature range. Instead of using conventional heating, the reaction can also be carried out in a microwave oven utilizing microwave radiation at temperatures from about 60° C. to about 200° C., for example at temperatures from about 30° C. to about 60° C. In such case, the reaction time generally is from about 5 minutes to about 12 hours, for example from about 10 minutes to about 3 hours, depending on the particulars of the specific case and the chosen temperature range. A plethora of methods for the formation of the peptide bond have been reported. The most successful approaches known today involve active ester formation with uronium/guanidinium salts. The most popular members of this family are peptide synthesis reagents based on benzotriazole derivatives such as HOBt or HOAt, both of which are also commonly used as additives in carbodiimide mediated peptide coupling like (TBTU, HBTU, HATU, EDC, BtFFH, ByPOP) in situ with an organic or inorganic base such as an amine like triethylamine, ethyldiisopropylamine, N-methylmorpholine or 1,8-diazabicyclo[5.4.0]unde-7-ene is used for activation of the corresponding carboxylic acid.

The reaction of compounds of the formulae VI with $R_2$-$G_2$ or formulae XII with is $R_2$-$G_2$, a $S_N2$-type reaction, and is favourably carried out in the presence of a base, for example an alkali metal carbonate or alkali metal phosphate like cesium carbonate, sodium carbonate or tripotassium phosphate, in an inert solvent, such as a hydrocarbon like benzene, toluene or xylene, or an ether like tetrahydrofuran (THF), dioxane or 1,2-dimethoxyethane (DME), or an amide like dimethylformamide, N-methylpyrrolidinone, dimethylacetamide, a sulfoxide like dimethylsulfoxide, or a mixture of solvents, at temperatures from about 20° C. to about 200° C., for example at temperatures from about 30° C. to about 60° C. The reaction time generally is from about 30 minutes to about 48 hours, preferably from 30 minutes to about 16 hours, depending on particulars of the specific case and the chosen temperature range.

Nitro groups can be reduced to amino groups with various reducing agents, such as sulfides, dithionites, complex hydrides or by catalytic hydrogenation. A reduction of a nitro group may also be carried out at a later stage of the synthesis of a compound of the formula I, and a reduction of a nitro group to an amino group may also occur simultaneously with a reaction performed on another functional group, for example when reacting a group like a cyano group with hydrogen sulfide or when hydrogenating a group. In order to introduce these residues, amino groups can then be modified according to standard procedures for alkylation, for example by reaction with (substituted) alkyl halogenides or by reductive amination of carbonyl compounds, according to standard procedures for acylation, for example by reaction with activated carboxylic acid derivatives such as acid chlorides, anhydrides, activated esters or others or by reaction with carboxylic acids in the presence of an activating agent, or according to standard procedures for sulfonylation, for example by reaction with sulfonyl chlorides.

Ester groups can be hydrolyzed to the corresponding carboxylic acids under basic conditions in NaOH/MeOH and/or water, which after activation can then be reacted with amines or alcohols under standard conditions. Furthermore these esters can be hydrolyzed under acid conditions with HBr/AcOH.

The previously-mentioned reactions for the conversion of functional groups are furthermore, in general, extensively described in textbooks of organic chemistry in which details on the reactions and primary source literature can be found. Due to the fact that in the present case the functional groups are attached to xanthine derivatives it may in certain cases become necessary to specifically adapt reaction conditions or to choose specific reagents from a variety of reagents that can in principle be employed in a conversion reaction, or otherwise to take specific measures for achieving a desired conversion, for example to use protection group techniques. However, finding suitable reaction variants and reaction conditions in such cases does not cause any problems for one skilled in the art.

The structural elements present in the residues at the $R_1$, $R_2$ and $R_3$ position of the xanthine derivatives of the formula I can be introduced for example at the stage of a suitable precursor or the using the methods outlined above by consecutive reaction steps using parallel synthesis methodologies like those outlined below using procedures which per se are well known to one skilled in the art.

In the course of the preparation of the compounds of the formula I it can generally be advantageous or necessary to introduce functional groups which reduce or prevent undesired reactions or side reactions in the respective synthesis steps, in the form of precursor groups which are later converted into the desired functional groups, or to temporarily block functional groups by a protective group strategy suited to the synthesis problem. Such strategies are well known to those skilled in the art. Examples of precursor groups are cyano groups and nitro groups. The cyano group can, in a later step, be transformed into carboxylic acid derivatives or by reduction into aminomethyl groups. Nitro groups may be transformed by reduction like catalytic hydrogenation into amino groups. Protective groups can also have the meaning of a solid phase, and cleavage from the solid phase stands for the removal of the protective group. The use of such techniques is known to those skilled in the art. For example, a phenolic hydroxy group can be attached to a trityl-polystyrene resin, which serves as a protecting group, and the molecule is cleaved from this resin by treatment with TFA or other acids at a later stage of the synthesis.

If a residue of the xanthine derivatives of the formula I are present in protected form or in the form of a precursor group, which have not already been introduced during a preceding step, for example during a synthesis of the xanthine derivative nucleus, these residues can, for example, be introduced the by standard alkylation procedures at 7-position of the nitrogen well-known to one skilled in the art. Alkylation of the aforementioned atom can, for example, be performed under standard conditions, preferably in the presence of a base like potassium carbonate, cesium carbonate, sodium hydride or potassium tert-butoxide, using an alkylating reagent containing a leaving group, like for example halogen like chlorine, bromine or iodine, or a sulfonyloxy group like tosyloxy, mesyloxy or trifluormethylsulfonyloxy. These standard procedures are known to the skilled person.

As is usual and applies to all reactions performed in the course of the synthesis of a compound of the formula I, appropriate details of the conditions applied in a specific preparation process, including the solvent, a base or acid, the temperature, the order of addition, the molar ratios and other parameters, are routinely chosen by the skilled person in view of the characteristics of the starting compounds and the target compound and the other particularities of the specific case. As is also known by the skilled person, not all processes described herein will in the same way be suitable for the preparation of all compounds of the formula I and their intermediates, and adaptations have to be made. In all processes for the preparation of the compounds of the formula I, workup of the reaction mixture and the purification of the product is performed according to customary methods known to the skilled person which include, for example, quenching of a reaction mixture with water, adjustment of a certain pH, precipitation, extraction, drying, concentration, crystallization, distillation and chromatography. As further examples of methods applicable in the synthesis of the compounds of the formula I, microwave assistance for speeding-up, facilitating or enabling reactions, may be mentioned, and modern separation techniques like preparative high pressure liquid chromatography (HPLC), which can be used for separating mixtures of positional isomers which may occur in any reactions. Also for the characterization of the product, customary methods are used such as NMR, IR and mass spectroscopy.

Another subject of the present invention are the novel starting compounds and intermediates occurring in the synthesis of the compounds of the formula I, including the compounds of the formulae II, III, IV, V, VII, VIII, IX, X, XI and XII wherein the groups $R^1$, $R^2$, $R^3$, Q, X, Z and $G^1$, $G^2$, and the number n are defined as above, in any of their stereoisomeric forms or a mixture of stereoisomeric forms in any ratio, and their salts, and their use as synthetic intermediates or starting compounds. All general explanations, specifications of embodiments and definitions of numbers and groups given above with respect to the compounds of the formula I apply correspondingly to the said intermediates and starting compounds. Subject of the invention are in particular the novel specific starting compounds and intermediates described herein. Independently thereof whether they are described as a free compound and/or as a specific salt, they are a subject of the invention both in the form of the free compounds and in the form of their salts, and if a specific salt is described, additionally in the form of this specific salt.

Pharmaceutical Preparations and Administration

When used in human or veterinary therapy, the xanthine compounds of Formula I and their pharmaceutically acceptable salts will generally be administered as a formulation in association with one or more pharmaceutically acceptable excipients. The term "excipient" is used herein to describe any ingredient other than the compound of the invention. The choice of excipient strongly depends on the particular mode of administration.

The compounds of the invention may be administered orally. Oral administration may involve swallowing, so that the compound enters the gastrointestinal tract, or buccal or sublingual administration may be employed by which the compound enters the blood stream directly from the mouth. Formulations suitable for oral administration include: solid formulations such as tablets; capsules containing particulates, liquids, or powders; lozenges (including liquid-filled); and chews; multi- and nano-particulates; gels; solid solutions; liposomes; films, ovules, sprays and liquid formulations. Liquid formulations include suspensions, solutions, syrups and elixirs. Such formulations may be employed as fillers in soft or hard capsules and typically comprise a carrier, for example, water, ethanol, polyethylene glycol, propylene glycol, methylcellulose, or a suitable oil, and one or more emulsifying agents and/or suspending agents. Liquid formulations may also be prepared by the reconstitution of a solid, for example, from a sachet.

For tablet dosage forms, depending on dose, the drug may make up from 0.1 weight % to 80 weight % of the dosage form, more typically from 1 weight % to 60 weight % of the dosage form.

In addition to the drug, tablets may contain a disintegrant. Examples of disintegrants include sodium starch glycolate, sodium carboxymethyl cellulose, calcium carboxymethyl cellulose, croscarmellose sodium, crospovidone, polyvinylpyrrolidone, methyl cellulose, microcrystalline cellulose, lower alkyl-substituted hydroxypropyl cellulose, starch, pregelatinised starch and sodium alginate. Generally, the disintegrant will comprise from 1 weight % to 25 weight %, preferably from 5 weight % to 20 weight % of the dosage form.

Binders are generally used to impart cohesive qualities to a tablet formulation. Suitable binders include microcrystalline cellulose, gelatin, sugars, polyethylene glycol, natural and synthetic gums, polyvinylpyrrolidone, pregelatinised starch, hydroxypropyl cellulose and hydroxypropyl methylcellulose. Tablets may also contain diluents, such as lactose (monohydrate, spray-dried monohydrate, anhydrous and the like), mannitol, xylitol, dextrose, sucrose, sorbitol, microcrystalline cellulose, starch and dibasic calcium phosphate dihydrate.

Tablets may also optionally comprise surface active agents, such as sodium lauryl sulfate and polysorbate 80, and glidants such as silicon dioxide and talc. When present, surface active agents may comprise from 0.2 weight % to 5 weight % of the tablet, and glidants may comprise from 0.2 weight % to 1 weight % of the tablet.

Tablets also may contain lubricants such as magnesium stearate, calcium stearate, zinc stearate, sodium stearyl fumarate, and mixtures of magnesium stearate with sodium lauryl sulphate. Lubricants generally comprise from 0.25 weight % to 10 weight %, preferably from 0.5 weight % to 3 weight % of the tablet.

Exemplary tablets contain up to about 80% drug, from about 10 weight % to about 90 weight % binder, from about 0 weight % to about 85 weight % diluent, from about 2 weight % to about 10 weight % disintegrant, and from about 0.25 weight % to about 10 weight % lubricant.

Other possible ingredients include anti-oxidants, colourants, flavouring agents, flavour enhancers, preservatives, taste-masking agents, salivary stimulating agents, co-solvents (including oils), emollients, bulking agents and anti-foaming agents.

The compounds of the invention may also be administered directly into the blood stream, into muscle, or into an internal organ. Suitable means for parenteral administration include intravenous, intraarterial, intraperitoneal, intrathecal, intraventricular, intraurethral, intrasternal, intracranial, intramuscular and subcutaneous. Suitable devices for parenteral administration include needle (including microneedle) injectors, needle-free injectors and infusion techniques.

Parenteral formulations are typically aqueous solutions which may contain excipients such as salts, carbohydrates and buffering agents (preferably to a pH of from 3 to 9), but, for some applications, they may be more suitably formulated as a sterile non-aqueous solution or as a dried form to be used in conjunction with a suitable vehicle such as sterile, pyrogen-free water.

The compounds of the invention may also be administered topically to the skin or mucosa, that is, dermally or transdermally. Typical formulations for this purpose include gels, hydrogels, lotions, solutions, creams, ointments, dusting powders, dressings, foams, films, skin patches, wafers, implants, sponges, fibres, bandages and microemulsions. Liposomes may also be used. Typical carriers include alcohol, water, mineral oil, liquid petrolatum, white petrolatum, glycerin, polyethylene glycol and propylene glycol. Other means of topical administration include delivery by electroporation, iontophoresis, phonophoresis, sonophoresis and microneedle or needle-free injection.

The compounds of the invention can also be administered intranasally or by inhalation, typically in the form of a dry powder (either alone, as a mixture, for example, in a dry blend with lactose, or as a mixed component particle, for example, mixed with phospholipids, such as phosphatidylcholine) from a dry powder inhaler or as an aerosol spray from a pressurised container, pump, spray, atomiser, or nebuliser, with or without the use of a suitable propellant. For intranasal use, the powder may comprise a bioadhesive agent, for example, chitosan or cyclodextrin. The pressurised container, pump, spray, atomizer, or nebuliser contains a solution or suspension of the compound(s) of the invention comprising, for example, ethanol, aqueous ethanol, or a suitable alternative agent for dispersing, solubilising, or extending release of the active, a propellant(s) as solvent and an optional surfactant, such as sorbitan trioleate, oleic acid, or an oligolactic acid.

Further modes of administration include rectal or vaginal administration, ocular or aural administration.

All formulations mentioned above may be formulated to be immediate and/or modified release. Modified release formulations include delayed-, sustained-, pulsed-, controlled-, targeted and programmed release.

According to the present invention, the xanthine derivative is administered preferably at an effective dose. An "effective dose" is the dose of the xanthine derivative that upon administration to a patient yields a measurable therapeutic effect with regard to the disease of interest. In the present invention an effective dose is the dose of the xanthine derivative that upon administration to a patient yields a therapeutic effect with regard to the level of serotonin in the corresponding organ.

For administration to human patients, the total daily dose of the compounds of the invention is typically in the range 0.001 mg to 5000 mg depending, of course, on the mode of administration. The total daily dose may be administered in single or divided doses and may, at the physician's discretion, fall outside of the typical range given herein.

As used herein, the term "treating" refers to reversing, alleviating or inhibiting the progress of a disease, disorder or condition, or one or more symptoms of such disease, disorder or condition, to which such term applies. As used herein, "treating" may also refer to decreasing the probability or incidence of the occurrence of a disease, disorder or condition in a mammal as compared to an untreated control population, or as compared to the same mammal prior to treatment. For example, as used herein, "treating" may refer to preventing a disease, disorder or condition, and may include delaying or preventing the onset of a disease, disorder or condition, or delaying or preventing the symptoms associated with a disease, disorder or condition. As used herein, "treating" may also refer to reducing the severity of a disease, disorder or condition or symptoms associated with such disease, disorder or condition prior to a mammal's affliction with the disease, disorder or condition. Such prevention or reduction of the severity of a disease, disorder or condition prior to affliction relates to the administration of the composition of the present invention, as described herein, to a subject that is not at the time of administration afflicted with the disease, disorder or condition. As used herein "treating" may also refer to preventing the recurrence of a disease, disorder or condition or of one or more symptoms associated with such disease, disorder or condition. The terms "treatment" and "therapeutically," as used herein, refer to the act of treating, as "treating" is defined above.

DETAILED DESCRIPTION OF THE INVENTION

Figure 1B:
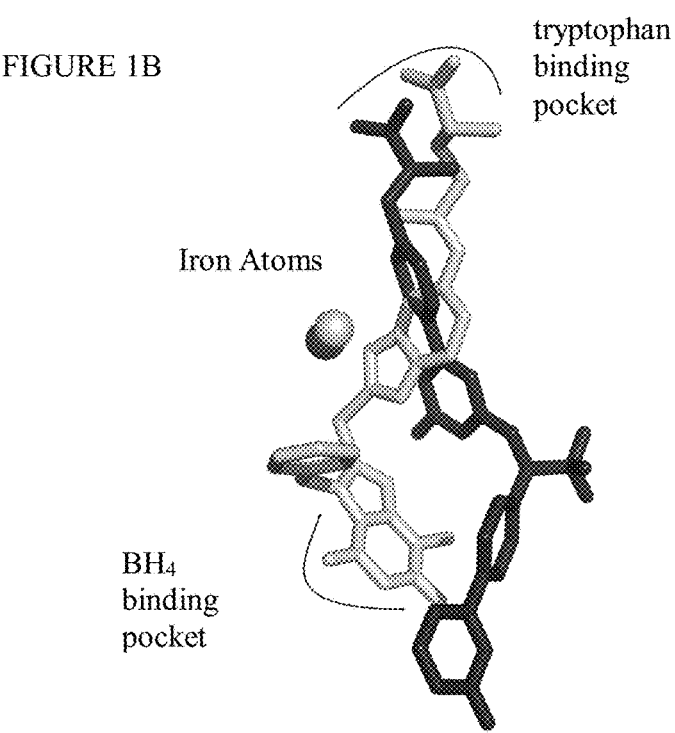

The invention will be described in more detail by way of preferred embodiments. The Figures show:

FIG. 1A Superimposition of the crystal structure of human TPH1 in complex with the inhibitor LP533401 (overall protein fold as black cartoon model, inhibitor as black stick model) and in complex with the inhibitor KM480 according to the invention (overall protein fold as gray cartoon model, inhibitor as gray stick model), FIG. 1B Superimposition of the inhibitors LP533401 (black stick model) and KM480 (gray stick model) and their binding positions within TPH1 with respect to the tryptophan substrate binding site and the original $BH_4$ cofactor binding site, respectively.

DEFINITIONS

Unless otherwise indicated, the term "alkyl" means a linear or branched and/or cyclic hydrocarbon, which is optionally substituted. Representative (C1-C10)-alkyl moieties include methyl, ethyl, n-propyl, isopropyl, n-butyl, isobutyl, t-butyl, n-pentyl, isopentyl, n-hexyl, isohexyl, n-heptyl, isoheptyl, n-octyl, isooctyl, n-nonyl, isononyl, and decyl. Cycloalkyl moieties include monocyclic alkyl groups or polycyclic alkyl groups bound or fused (annealed) together in a vicinal or geminal (spirocyclic bound) fashion. Representative cycloalkyl moieties include cyclopropyl, cyclobutyl, cyclopentyl, cyclohexyl, cycloheptyl and adamantyl.

Unless otherwise indicated, the term "alkenyl" means a linear, branched and/or cyclic hydrocarbon having at least one carbon-carbon double bond. Representative (C2-C10)-alkenyl moieties include vinyl (ethenyl), allyl (2-propenyl), 1-propenyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, 1-hexenyl, 2-hexenyl, 3-hexenyl, 1-heptenyl, 2-heptenyl, 3-heptenyl, 1-octenyl, 2-octenyl, 3-octenyl, 1-nonenyl, 2-nonenyl, 3-nonenyl, 1-decenyl, 2-decenyl and 3-decenyl. Representative (C2-C10)-cycloalkenyl moieties include 1-cyclobutenyl, 2-cyclobutenyl, 2-cyclopentenyl, 3-cyclopentenyl, 2,4-cyclopentdienyl, 1-cyclohexyl, 2-cyclohexyl, 3-cyclohexyl, 2,5-cyclohexadienyl and cyclohepten.

Unless otherwise indicated, the term "alkynyl" means a linear, branched and/or cyclic hydrocarbon having at least one carbon-carbon triple bond. Representative (C2-C10)-alkynyl moieties include acetylenyl, propynyl, 1-butynyl, 2-butynyl, 1-pentynyl, 2-pentynyl, 3-methyl-1-butynyl, 4-pentynyl, 1-hexynyl, 2-hexynyl, 5-hexynyl, 1-heptynyl, 2-heptynyl, 6-heptynyl, 1-octynyl, 2-octynyl, 7-octynyl, 1-nonynyl, 2-nonynyl, 8-nonynyl, 1-decynyl, 2-decynyl and 9-decynyl. Representative (C2-C10)-cycloalkynyl moieties include cycloheptin, cyclooctin and cyclononin with arbitrary position of the triple bond.

Unless otherwise indicated, the term "alkylene" means an bivalent alkyl moiety linking two other moieties.

Unless otherwise indicated, the term "alkenylene" means an bivalent alkenyl moiety linking two other moieties.

Unless otherwise indicated, the term "alkynylene" means an bivalent alkynyl moiety linking two other moieties.

Unless otherwise indicated, the term "aryl" means an aromatic ring or an aromatic or a partially aromatic ring system composed of carbon and hydrogen atoms. An aryl moiety may comprise multiple rings bound or fused together. Examples of aryl moieties include phenyl, biphenyl, anthracenyl, azulenyl, fluorenyl, indanyl, indenyl, naphthyl, phenanthrenyl, 1,2,3,4-tetrahydro-naphthalene and tolyl.

Unless otherwise indicated, the prefix "hetero" means that at least one carbon atom or carbon member in the hydrocarbon chain (e.g. —C— or —CH— or —$CH_2$—) is substituted by a hetero atom or hetero member, selected from oxygen (—O—), nitrogen (—N— or —N= or —NH—), sulfur (—S—), or phosphor (—P— or —PH— or). In aromatic or non-aromatic heterocycles, the prefix (Cn-Cm), with n and m being integers, defines the number of members of the heterocycle, irrespective whether the member is carbon or a hetero atom. For example, the term "(C5-C14)-heteroaryl" means a five- to fourteen-membered ring or ring system, in which at least one carbon atom or carbon member is substituted by a hetero atom or hetero member.

Unless otherwise indicated, the term "alkyl-aryl" or "alkyl-heteroaryl" means an alkyl moiety as defined above bound to an aryl moiety or to an heteroaryl moiety as defined above, respectively. Unless otherwise indicated, the term "alkenyl-aryl" or "alkenyl-heteroaryl" means an alkenyl moiety as defined above bound to an aryl moiety or to an heteroaryl moiety as defined above, respectively. Unless otherwise indicated, the term "alkynyl-aryl" or "alkynyl-heteroaryl" means an alkynyl moiety as defined above bound to an aryl moiety or to an heteroaryl moiety as defined above, respectively.

Unless otherwise indicated, the term "aryl-alkylene" or "heteroaryl-alkylene" means an aryl moiety or a heteroaryl moiety as defined above bound to an alkylene moiety as defined above, respectively. Likewise, the term "aryl-alkenylene" or "heteroaryl-alkenylene" means an aryl moiety or a heteroaryl moiety as defined above bound to an alkenylene moiety, respectively. Likewise, the term "aryl-alkynylene" or "heteroaryl-alkynylene" means an aryl moiety or a heteroaryl moiety as defined above bound to an alkynylene moiety, respectively.

Unless otherwise indicated, in composite systems such as "alkyl-aryl", "alkyl-heteroaryl", "alkenyl-aryl", "alkenyl-heteroaryl", "alkynyl-aryl", "alkynyl-heteroaryl", "aryl-alkylene", "heteroaryl-alkylene", "aryl-alkenylene", "heteroaryl-alkenylene", "aryl-alkynylene" and "heteroaryl-alkynylene" the prefix (Cn-Cm), with n and m being integers, defines the number of all members of the composite system. For instance, (C6-C15)-aryl-alkylene means that the system comprising the alkylene unit and the aryl unit is composed of six to fifteen members in total, except for further substituents if any.

Unless otherwise indicated, the phrase "bivalent group substituting a carbon moiety in the hydrocarbon chain of an alkyl, alkenyl, alkynyl, alkylene, alkylene or alkenylene group" indicates the occurrence of a functional group in any position of the hydrocarbon chain. For instance, a (C1-C10)-alkyl group comprising the bivalent oxygen group —O— means a —(C0-$C_a$)-alkylene-O—(C0-$C_b$)-alkyl group, with (a+b)≤10. In this example, when the hetero oxygen atom is present at the C1-position, the group is an alkoxy group —O—($C_1$-$C_{10}$)-alkyl. When the hetero oxygen atom is present at an intermediate position, the group is an ether group.

35

For the purpose of the present invention and unless otherwise indicated, substituents generally comprise the following groups: fluoro —F, bromo —Br, chloro —Cl, hydroxyl —OH, carbonyl —C(O)R, carboxyl —C(O)OH, carboxylate —C(O)O—, carboxy ester —CO$_2$R, alkoxy —OR, aldehyde —C(O)H, trihalide methyl ester —OCX$_3$, primary, secondary and tertiary amine —NR(R'), amide —N(R)—C(O)—R, imide —C(O)—N(R)—C(O)—R', carbamate —N(R)—C(O)—OR', carboxamide —C(O)N(R)(R'), carbimide —N(R)—C(O)—N(R')R", primary and secondary ketimine —(R)=NR', a secondary ketimine —(R)=NH, nitrile —CN, isonitrile, —NC, nitroxy —ONO, nitro —NO$_2$, nitrate —ONO$_2$, nitroso —NO, cyanate —OCN, isocyanate —NCO, sulfhydryl —SH, sulfide —SR, sulfurtrihalide —SX$_3$, sulfurpentahalide —SX$_5$, sulfinyl —S(O)R, sulfonyl —SO$_2$R, sulfino —SO$_2$H, sulfo —SO$_3$H, and salts thereof. In the aforementioned substituents R, R' and R" are hydrogen, (C1-C3)-alkyl or (C2-C3)-alkenyl, and X means a halide (F, Br, Cl). In some cases two or three identical or different substituents may be bound to one carbon atom.

EXAMPLES

When in the final step of the synthesis of a compound an acid such as trifluoroacetic acid or acetic acid was used, for example when trifluoroacetic acid was employed to an acid-labile protecting group (eg. a tert-butyl group) or when a compound was purified by chromatography using an eluent which contained such an acid, in some cases, depending on the work-up procedure, for example the details of a freeze-drying process, the compound was obtained partially or completely in the form of a salt of the acid used, for example in the form of the acetic acid salt, formic acid salt or trifluoroacetic acid salt or hydrochloric acid salt. Likewise starting materials or intermediates bearing a basic center like for example a basic nitrogen were either obtained and used as free base or in salt form like, for example, a trifluoroacetic acid salt, a hydrobromic acid salt, sulfuric acid salt, or a hydrochloric acid salt.

Abbreviations

DCM Dichloromethane
dioxane [1,4]Dioxane
DMF N,N-Dimethylformamide
DMSO Dimethylsulfoxide
EtOAc Ethyl acetate
iPrOH Isopropanol
MeCN Acetonitrile
RT Room temperature (20° C. to 25° C.)
TFA Trifluoroacetic acid
LCMS Liquid Chromatography Mass Spectrometry
DIPEA N,N-Diisopropylethylamine
KOH Potassiumhydroxide
NaOH Sodiumhydroxide
TBTU N,N,N',N'-Tetramethyl-O-(benzotriazol-1-yl)uronium tetrafluoroborate
HOBt Hydroxybenzotriazole
Hex Hexane LCMS (method 1): Instrument: Agilent Technologies 6220 Accurate Mass TOF LC/MS linked to Agilent Technologies HPLC 1200 Series; Column: Thermo Accuore RP-MS; Particle Size: 2.6 μM Dimension: 30×2.1 mm;

36

Eluent A: H$_2$O with 0.1% TFA Eluent B: MeCN with 0.1% TFA; Gradient: 0.00 min 95% A, 0.2 min 95% A, 1.1 min 1% A, 2.5 min Stoptime, 1.3 min Posttime; Flow rate: 0.8 ml/min; UV-detection: 220 nm, 254 nm, 300 nm.

LCMS (method 2): Instrument: Agilent Technologies 6120 Quadrupole LC/MS linked to Agilent Technologies HPLC 1290 Infinity; Column: Thermo Accuore RP-MS; Particle Size: 2.6 μM Dimension: 30×2.1 mm; Eluent A: H$_2$O with 0.1% TFA Eluent B: MeCN with 0.1% TFA; Gradient: 0.00 min 95% A, 0.2 min 95% A, 1.1 min 1% A, 2.5 min Stoptime, 1.3 min Posttime; Flow rate: 0.8 ml/min; UV-detection: 220 nm, 254 nm, 300 nm.

Examples 1-29

Benzimidazolyl xanthines according to general formula I with Q=CH$_2$, Z=NH, and X=C were synthesized according to general procedure A.

General Procedure A

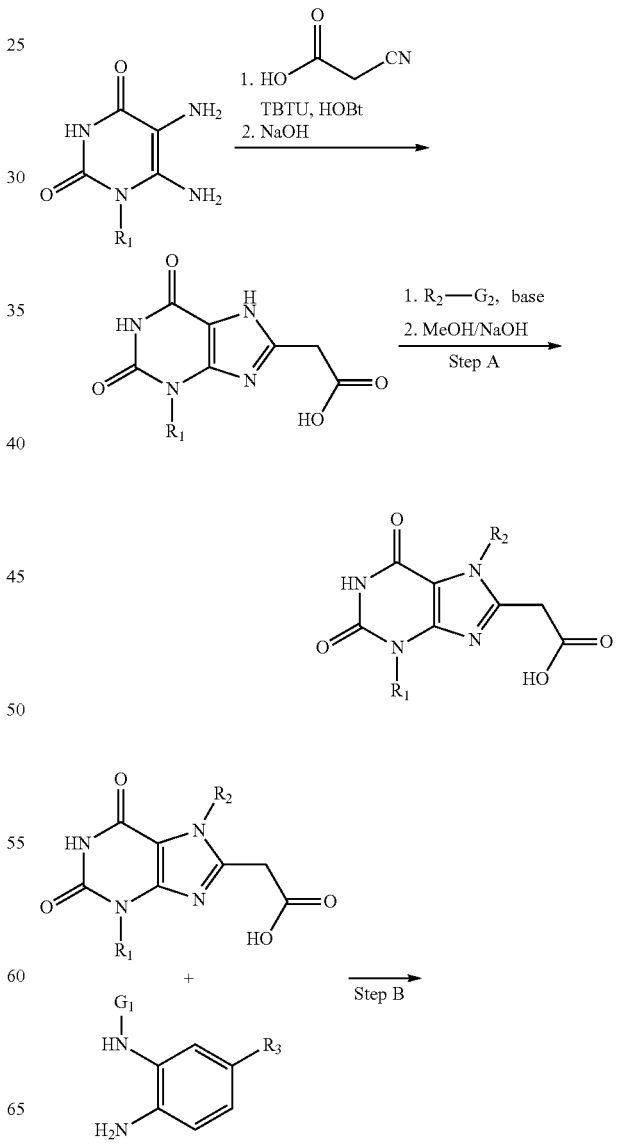

-continued

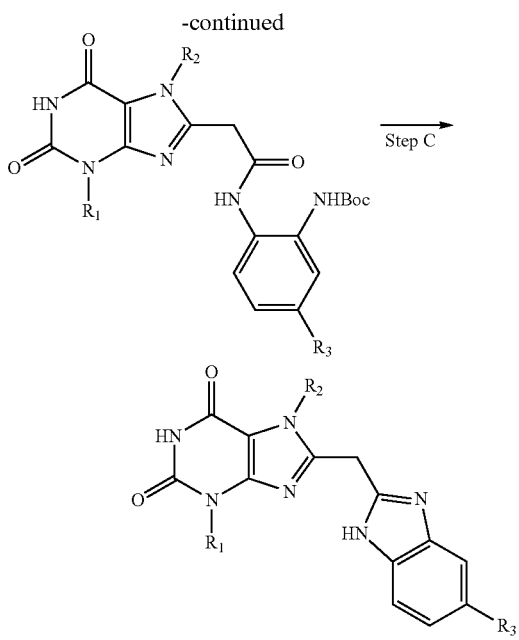

Synthesis of: 2-(3-alkyl-2,6-dioxo-2,3,6,7-tetrahydro-1H-purin-8-yl)acetic acid

The title compound was prepared by adding 5,6-diamino-1-alkyl-1,2,3,4-tetrahydropyrimidine-2,4-dione (57 mmol, alkyl=$R_1$) in 500 ml DMF, cyano acetic acid (4.84 g, 1.1 mmol), HOBt (13 g, 85 mmol) and a peptide coupling reagent like TBTU (27.3 g, 85 mmol) to a reaction vessel containing a magnetic stirring bar, followed by 59 ml DIPEA (6.6 mmol). The reaction mixture was stirred at RT for 20 h. DMF was evaporated and the organic phase was solubilized with EtOAc. The combined organic phases were washed with brine and dried over sodium sulfate and evaporated to afford the crude N-(6-amino-1-alkyl-2,4-dioxo-1,2,3,4-tetrahydropyrimidin-5-yl)-2-cyanoacetamide. The intermediate is added to a 10 M NaOH solution and refluxed for 20 h. The aqueous solution is acidified with conc. HCl solution to pH=6 at RT which resulted in precipitation of the crude product 2-(3-alkyl-2,6-dioxo-2,3,6,7-tetrahydro-1H-purin-8-yl)acetic acid. The solid was filtered off and washed and ether.

Step A:

The starting material (30 mmol) obtained in the previous step was dissolved in 150 ml DMF in a reaction vessel containing a magnetic stirring bar. 31 ml DIPEA (180 mmol) were added followed by addition of alkylation reagent $R_2$-$G_2$ (60 mmol), and the mixture heated to 55° C. under stirring. After 3 h the reaction mixture was cooled to RT and DMF was evaporated. The solid was homogenized in aqueous solution by means of sonification and was filtered off and dried under vacuum to give the crude product as intermediate. The resulting ester was solubilized in 20 ml MeOH and 10 ml of 10 M KOH solution was added. The reaction was stirred for 12 h at RT until the ester was completely saponified. MeOH was evaporated and the aqueous phase was acidified to pH=7. The aqueous phase was extracted three times with EtOAc and the aqueous phase was removed under reduced pressure.

Step B:

The product from Step A (1 mmol) was dissolved in 15 ml DMF. HOBt (1.5 mmol) and TBTU (1.5 mmol) were added and the reaction was stirred for 10 min at RT. After addition of N-Boc-1,2-phenylene-diamines (1.1 mmol) and 1 ml DIPEA (6 mmol) the suspension was heated to 50° C. for 3 h. Then the solvents were removed under reduced pressure and the crude product was purified by chromatography on silica gel eluting with a gradient of DCM/MeOH. The fractions containing the product were combined and the solvent evaporated under reduced pressure.

Step C:

The product from Step B (0.3 mmol) was dissolved in 3 ml acetic acid. After addition of 5 µl of $H_2SO_4$ the reaction mixture was heated for 20 min to 120° C. by using microwave irradiation. After cooling in ice bath the reaction was quenched with 0.5 M NaOH to pH=7. The crude product precipitated as light brownish foam and was filtered off. It was purified by chromatography on silica gel eluting with a gradient of DCM/MeOH. The fractions containing the product were combined and the solvent evaporated under reduced pressure.

Example 1: 8-(1H-1,3-benzodiazol-2-ylmethyl)-7-benzyl-3-cyclopropyl-2,3,6,7-tetrahydro-1H-purine-2,6-dione (KM-05-80)

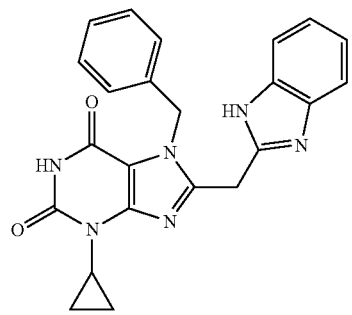

(I-1)

Synthesis of 2-(3-cyclopropyl-2,6-dioxo-2,3,6,7-tetrahydro-1H-purin-8-yl)acetic acid The title compound was prepared by adding 5,6-diamino-1-cyclopropyl-1,2,3,4-tetrahydropyrimidine-2,4-dione (14.2 g, 57 mmol) in 500 ml DMF, cyano acetic acid (4.84 g, 1.1 mmol), HOBt (13 g, 85 mmol) and a peptide coupling reagent like TBTU (27.3 g, 85 mmol) to a reaction vessel containing a magnetic stirring bar, followed by 59 ml DIPEA (6.6 mmol). The reaction mixture was stirred at RT for 20 h. DMF was evaporated and the organic phase was solubilized with EtOAc. The combined organic phases were washed with brine and dried over sodium sulfate and evaporated to afford the crude N-(6-amino-1-alkyl-2,4-dioxo-1,2,3,4-tetrahydropyrimidin-5-yl)-2-cyanoacetamide. The intermediate is added to a 10 M NaOH solution and refluxed for 20 h. The aqueous solution is acidified with conc. HCl solution to pH=6 at RT which results in precipitation of the crude product 2-(3-cyclopropyl-2,6-dioxo-2,3,6,7-tetrahydro-1H-purin-8-yl)acetic acid. The solid was filtered off and washed and ether. Yield: 15 g (76% over 2 steps).

LCMS (method 1): $R_t$=0.291 min; HRMS (ESIpos): m/z [M+H]$^+$ calcd for $C_{10}H_{10}N_4O_4$, 251.0775 found, 251.0794.

$^1$H NMR (300 MHz, DMSO-d$_6$) δ 12.80 (s, 1H), 10.96 (s, 1H), 3.73 (s, 2H), 2.89-2.85 (m, 1H), 1.04-0.85 (m, 4H).

Synthesis of 2-(7-benzyl-3-cyclopropyl-2,6-dioxo-2,3,6,7-tetrahydro-1H-purin-8-yl)acetic acid According to Step A in procedure A 2-(3-cyclopropyl-2,6-dioxo-2,3,6,7-tetrahydro-1H-purin-8-yl)acetic acid (15 g, 60.2 mmol) was dissolved in 300 ml DMF and was added to a reaction vessel containing a magnetic stirring bar together with DIPEA (46.7 g, 63 ml, 361 mmol) followed by addition of 14.3 ml benzylbromide (120.4 mmol), and the mixture heated to 55° C. under stirring. After 3 h the reaction mixture was cooled to RT and DMF was evaporated. The solid was homogenized in aqueous solution by means of sonification and it was filtered off and dried under vacuum to give 15 g of crude benzyl 2-(7-benzyl-3-cyclopropyl-2,6-dioxo-2,3,6,7-tetrahydro-1H-purin-8-yl)acetate. The crude product was purified by chromatography on silica gel eluting with a gradient of DCM/MeOH (Yield: 3.9 g 15%). The resulting ester was solubilized in 40 ml MeOH and 10 ml of 10 M KOH solution was added. The reaction was stirred for 12 h at RT until the complete saponification of the ester. MeOH was evaporated and the aqueous phase was acidified to pH=7. The aqueous phase was extracted three times with EtOAc and the aqueous phase was evaporated to give 2-(7-benzyl-3-cyclopropyl-2,6-dioxo-2,3,6,7-tetrahydro-1H-purin-8-yl)acetic acid as white solid. Yield: 3.13 g (99%).

LCMS (method 1): R$_t$=1.069 min; HRMS (ESIpos): m/z [M+H]$^+$ calcd for C$_{17}$H$_{16}$N$_4$O$_4$, 341.1244 found, 341.1254. $^1$H NMR (300 MHz, Deuterium Oxide) b=7.25-7.19 (m, 3H), 7.05 (d, J=6.5 Hz, 2H), 5.36 (s, 2H), 3.62 (s, 2H), 2.86-2.75 (m, 1H), 1.10-0.99 (m, 2H), 0.90-0.83 (m, 2H)

Synthesis of tert-butyl 2-(2-(7-benzyl-3-cyclopropyl-2,3,6,7-tetrahydro-2,6-dioxo-1H-purin-8-yl)acetamido)phenylcarbamate According to Step B, 2-(7-benzyl-3-cyclopropyl-2,6-dioxo-2,3,6,7-tetrahydro-1H-purin-8-yl)acetic acid (0.3 g, 0.88 mmol) was solubilized in 15 ml DMF. HOBt (0.2 g, 1.3 mmol) and TBTU (0.42 mg, 1.3 mmol) were added and the reaction was stirred for 10 min at RT. After addition of N-Boc-1,2-phenylene-diamine (0.2 g, 0.79 mmol) and DIPEA (5.29 mmol, 0.92 ml) the suspension was heated to 50° C. for 3 h. Then the solvents were removed under reduced pressure and the crude product was purified by chromatography on silica gel eluting with a gradient of DCM/MeOH. The fractions containing the product were combined and the solvent evaporated under reduced pressure. Yield: 175 mg (37%).

LCMS (method 2): R$_t$=1.107 min; MS (ESIpos) m/z=531.3 [M+H]$^+$.

Synthesis of 8-(1H-1,3-benzodiazol-2-ylmethyl)-7-benzyl-3-cyclopropyl-2,3,6,7-tetrahydro-1H-purine-2,6-dione According to Step C, 175 mg (0.33 mmol) tert-butyl 2-(2-(7-benzyl-3-cyclopropyl-2,3,6,7-tetrahydro-2,6-dioxo-1H-purin-8-yl)acetamido)phenylcarbamate was solubilized in 3 ml acetic acid. After addition of 5 µl of H$_2$SO$_4$ the reaction mixture was heated for 20 min to 120° C. by using microwave irradiation. After cooling in ice bath the reaction was quenched with 0.5 M NaOH to pH=7. The crude product precipitated as light brownish foam and was filtered off. It was purified by chromatography on silica gel eluting with a gradient of DCM/MeOH. The fractions containing the product were combined and the solvent evaporated under reduced pressure. Yield: 87 mg (64%).

LCMS (method 1): R$_t$=1.040 min; HRMS (ESIpos): m/z [M+H]$^+$ calcd for C$_{23}$H$_{20}$N$_6$O$_2$, 413.1721 found, 413.1717. $^1$H NMR (300 MHz, DMSO-d$_6$) δ 12.37 (s, 1H), 11.09 (s, 1H), 7.54 (d, J=7.0 Hz, 1H), 7.43 (d, J=7.0 Hz, 1H), 7.34-7.08 (m, 7H), 5.62 (s, 2H), 4.38 (s, 2H), 2.89-2.79 (m, 2H), 0.95 (m, 4H).

Example 2: 7-benzyl-3-cyclopropyl-8-{[5-(morpholin-4-yl)-1H-1,3-benzodiazol-2-yl]methyl}-2,3,6,7-tetrahydro-1H-purine-2,6-dione (KM-05-89)

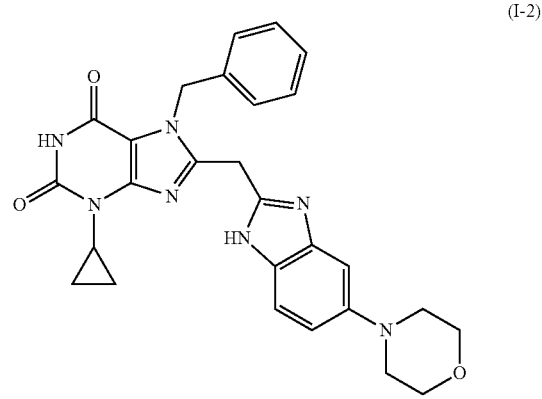 [SMILES: O=c1[nH]c(=O)n(C2CC2)c2nc(Cc3nc4cc(N5CCOCC5)ccc4[nH]3)n(Cc3ccccc3)c12]

(I-2)

Synthesis of 4-(3,4-dinitrophenyl)morpholine

In 10 ml DMF solubilized 3,4-dinitrofluorobenzene (0.4 g, 2.15 mmol) was stirred with a magnetic bar. At RT caesium carbonate (1.4 g, 4.3 mmol) and morpholine (281 µl, 3.22 mmol) were added and the suspension was stirred for 1 h. The caesium carbonate is filtered off and DMF was removed under reduced pressure. Yield: 0.51 g (94%).

LCMS (method 2): R$_t$=1.080 min; MS (ESIpos) m/z=254.1 [M+H]$^+$.

Synthesis of tert-butyl N-[2-amino-5-(morpholin-4-yl)phenyl]carbamate 0.51 g (2 mmol) 4-(3,4-dinitrophenyl)morpholine and 0.05 g Pd/C were suspended in 50 ml MeOH and the flask was purged with H$_2$. The reaction mixture was stirred for 2 h under H$_2$-atmosphere at RT. In 10 ml MeOH solubilized 0.44 g (2 mmol) Boc$_2$O and 0.28 ml (2 mmol) NEt$_3$ is added dropwise under N$_2$-atmosphere and the reaction was kept under N$_2$ stirring at RT for 2 h. Pd/C was filtered off over Celite® and the solvent was removed under reduced pressure. The crude product was purified by chromatography on silica gel eluting with a gradient of Hex/EtOAc. The fractions containing the product were combined and the solvent evaporated under reduced pressure. Yield: 335 mg (57%).

LCMS (method 1): R$_t$=1.108 min; HRMS (ESIpos): m/z [M+Na]$^+$ calcd for C$_{15}$H$_{23}$N$_3$O$_3$, 294.1812 found, 294.1814.

Synthesis of tert-butyl N-{2-[2-(7-benzyl-3-cyclopropyl-2,6-dioxo-2,3,6,7-tetrahydro-1H-purin-8-yl)acetamido]-5-(morpholin-4-yl)phenyl}carbamate 2-(7-benzyl-3-cyclopropyl-2,6-dioxo-2,3,6,7-tetrahydro-1H-purin-8-yl)acetic acid and tert-butyl N-[2-amino-5-(morpholin-4-yl)phenyl]carbamate were used as starting material and reacted according to Step B to give tert-butyl N-{2-[2-(7-benzyl-3-cyclopropyl-2,6-dioxo-2,3,6,7-tetrahydro-1H-purin-8-yl)acetamido]-5-(morpholin-4-yl)phenyl}carbamate Yield: 100 mg (53%).

LCMS (method 1): $R_t$=1.273 min; HRMS (ESIpos): m/z [M+H]$^+$ calcd for $C_{32}H_{37}N_7O_6$, 616.2878 found, 616.2895 [M+H]. $^1$H NMR (600 MHz, DMSO-d$_6$) δ=11.12 (s, 1H), 9.69 (s, 1H), 7.42-7.38 (m, 2H), 7.38-7.33 (m, 2H), 7.28 (d, J=7.6 Hz, 2H), 7.11 (s, 1H), 6.83 (dd, J=2.8, 9.0 Hz, 1H), 5.63 (s, 2H), 3.79 (d, J=4.8 Hz, 4H), 3.10-3.05 (m, 4H), 2.95 (s, 1H), 1.47 (s, 9H), 1.09-1.05 (m, 2H), 1.05-1.01 (m, 2H).

Synthesis of 7-benzyl-3-methyl-8-{[5-(morpholin-4-yl)-1H-1,3-benzodiazol-2-yl]methyl}-2,3,6,7-tetrahydro-1H-purine-2,6-dione According to Step C, tert-butyl N-{2-[2-(7-benzyl-3-cyclopropyl-2,6-dioxo-2,3,6,7-tetrahydro-1H-purin-8-yl)acetamido]-5-(morpholin-4-yl)phenyl}carbamate was cyclized to 7-benzyl-3-methyl-8-{[5-(morpholin-4-yl)-1H-1,3-benzodiazol-2-yl]methyl}-2,3,6,7-tetrahydro-1H-purine-2,6-dione: Yield: 28.5 mg (60%).

LCMS (method 1): $R_t$=1.027 min; HRMS (ESIpos): m/z [M+H]$^+$ calcd for $C_{27}H_{27}N_7O_3$, 498.2248 found, 498.2246. $^1$H NMR (600 MHz, DMSO-d$_6$) δ 12.28 (s, 1H), 11.08 (s, 1H), 7.35-7.29 (m, 2H), 7.28-7.21 (m, 3H), 6.98-6.89 (m, 2H), 5.62 (s, 2H), 4.34 (s, 2H), 3.80-3.74 (m, 4H), 3.10-3.04 (m, 4H), 2.86 (s, 1H), 0.99-0.92 (m, 4H).

Example 3: 8-(1H-1,3-benzodiazol-2-ylmethyl)-7-benzyl-3-methyl-2,3,6,7-tetrahydro-1H-purine-2,6-dione (KM-05-16)

lp;1p

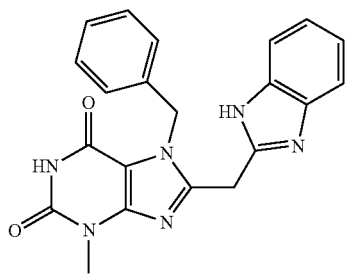

(I-3)

LCMS (method 1): $R_t$=1.165 min; HRMS (ESIpos): m/z [M+H]$^+$ calcd for $C_{21}H_{18}N_6O_2$, 387.1564 found, 387.1568. $^1$H NMR (600 MHz, DMSO-d$_6$) δ 12.39 (s, 1H), 11.18 (s, 1H), 7.55 (d, J=7.5 Hz, 1H), 7.45 (d, J=7.5 Hz, 1H), 7.34-7.28 (m, 2H), 7.27 (d, J=6.7 Hz, 1H), 7.24 (d, J=7.5 Hz, 2H), 7.19-7.13 (m, 2H), 5.65 (s, 2H), 4.40 (s, 2H), 3.34 (s, 3H).

Example 4: 7-benzyl-3-methyl-8-{[6-(morpholin-4-yl)-1H-1,3-benzodiazol-2-yl]methyl}-2,3,6,7-tetrahydro-1H-purine-2,6-dione (KM-05-50)

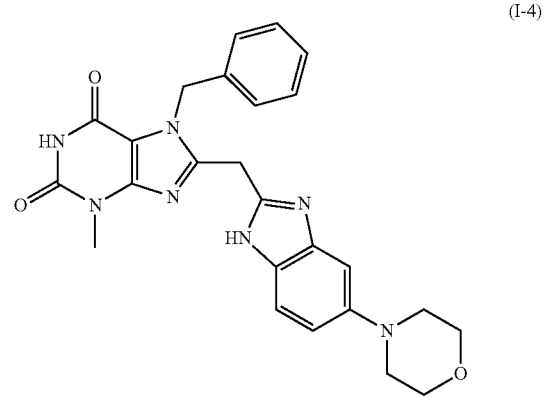 [SMILES: Cn1c(=O)[nH]c(=O)c2c1nc(Cc1nc3cc(N4CCOCC4)ccc3[nH]1)n2Cc1ccccc1]

(I-4)

LCMS (method 1): $R_t$=1.014 min; HRMS (ESIpos): m/z [M+H]$^+$ calcd for $C_{25}H_{25}N_7O_3$, 472.2092 found, 472.2094. $^1$H NMR (600 MHz, DMSO-d$_6$) δ 11.31 (s, 1H), 7.56 (d, J=9.0 Hz, 1H), 7.39-7.33 (m, 2H), 7.33-7.27 (m, 3H), 7.19 (dd, J=2.5, 8.9 Hz, 1H), 7.09 (s, 1H), 5.73 (s, 2H), 4.67 (s, 2H), 3.85-3.83 (m, 4H), 3.34 (s, 3H, overlay H$_2$O peak), 3.21-3.19 (m, 4H).

Example 5: 7-benzyl-3-methyl-8-((6-(4-methylpiperazin-1-yl)-1H-benzo[d]imidazol-2-yl)methyl)-1H-purine-2,6(3H,7H)-dione (KM-05-52)

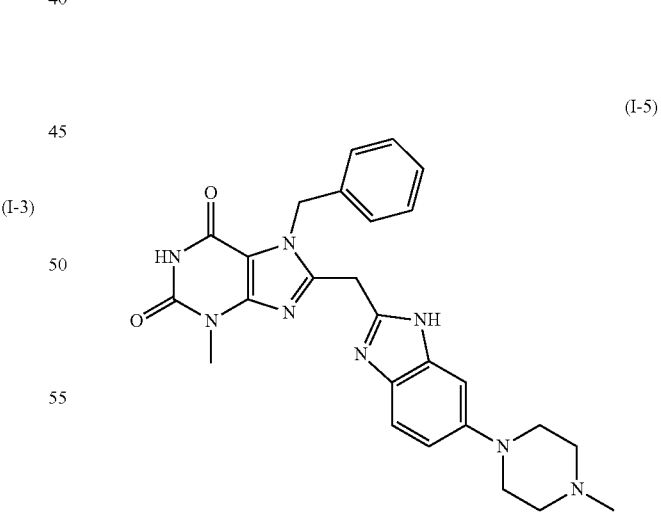

(I-5)

LCMS (method 1): $R_t$=0.428 min; HRMS (ESIpos): m/z [M+H]$^+$ calcd for $C_{26}H_{28}N_8O_2$, 485.2408 found, 485.2414. $^1$H NMR (600 MHz, DMSO-d$_6$) δ 12.13 (s, 1H), 11.18 (s, 1H), 7.41-7.20 (m, 6H), 7.06-6.85 (m, 2H), 5.63 (s, 2H), 4.33 (s, 2H), 3.34 (s, 3H, overlay H$_2$O peak), 3.13-3.01 (m, 4H), 2.53-2.45 (m, 4H, overlay DMSO peak), 2.23 (s, 3H).

Example 6: 8-((6-amino-1H-benzo[d]imidazol-2-yl)methyl)-7-benzyl-3-methyl-1H-purine-2,6(3H,7H)-dione (KM-05-55 Fr10-12)

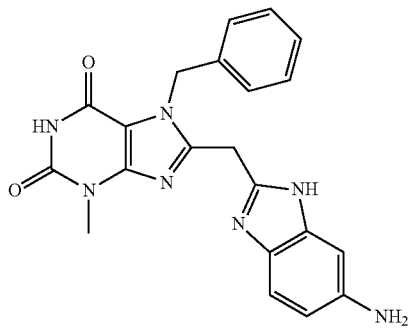

(I-6)

LCMS (method 1): R$_t$=0.697 min; HRMS (ESIpos): m/z [M+Na]$^+$ calcd for C$_{21}$H$_{19}$N$_7$O$_2$, 402.1498 found, 402.1519. $^1$H NMR (600 MHz, DMSO-d$_6$) δ 11.17 (s, 1H), 7.35-7.31 (m, 2H), 7.30-7.27 (m, 1H), 7.24 (d, J=7.3 Hz, 2H), 7.19 (d, J=8.5 Hz, 1H), 6.64 (s, 1H), 6.52 (d, J=8.4 Hz, 1H), 5.63 (s, 2H), 4.29 (s, 2H), 3.32 (s, 3H).

Example 7: N-(2-((7-benzyl-2,3,6,7-tetrahydro-3-methyl-2,6-dioxo-1H-purin-8-yl)methyl)-1H-benzo[d]imidazol-6-yl)acetamide (KM-05-55 Fr16-17)

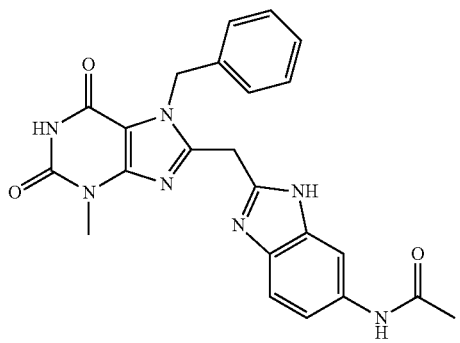

(I-7)

LCMS (method 1): R$_t$=0.966 min; HRMS (ESIpos): m/z [M+H]$^+$ calcd for C$_{23}$H$_{21}$N$_7$O$_3$, 444.1779 found, 444.1796.

Example 8: 1-(2-((7-benzyl-2,3,6,7-tetrahydro-3-methyl-2,6-dioxo-1H-purin-8-yl)methyl)-1H-benzo[d]imidazol-6-yl)piperidine-4-carboxylic acid (KM-05-68)

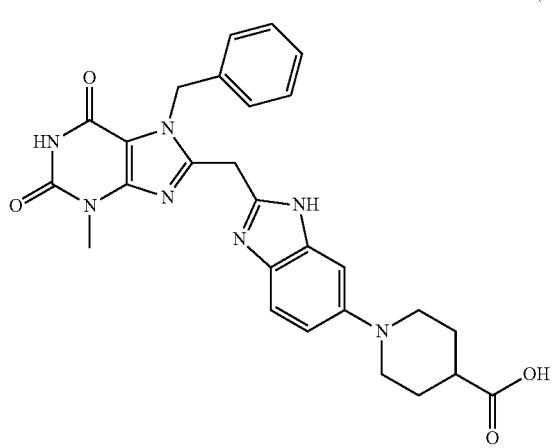

(I-8)

LCMS (method 2): R$_t$=0.788 min; MS (ESIpos) m/z=514.3 [M+H]$^+$.

Example 9: 7-benzyl-3-cyclopropyl-8-((5-(piperazin-1-yl)-1H-benzo[d]imidazol-2-yl)methyl)-1H-purine-2,6(3H,7H)-dione (KM-05-93)

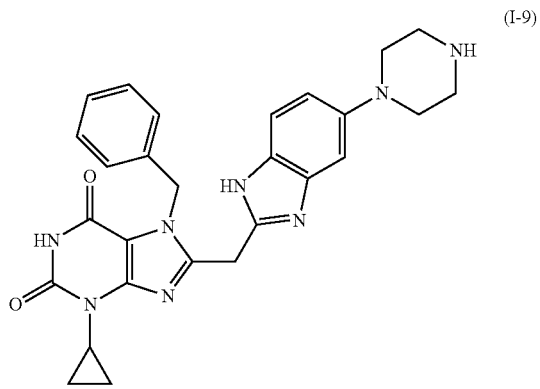 [SMILES: O=c1[nH]c(=O)n(C2CC2)c2nc(Cc3nc4cc(N5CCNCC5)ccc4[nH]3)n(Cc3ccccc3)c12]

(I-9)

LCMS (method 2): R$_t$=0.689 min; MS (ESIpos) m/z=497.3 [M+H]$^+$.

Example 10: (2S)-2-amino-4-({2-[(7-benzyl-3-methyl-2,6-dioxo-2,3,6,7-tetrahydro-1H-purin-8-yl)methyl]-1H-1,3-benzodiazol-5-yl}carbamoyl)butanoic acid hydrochloride (KM-05-60)

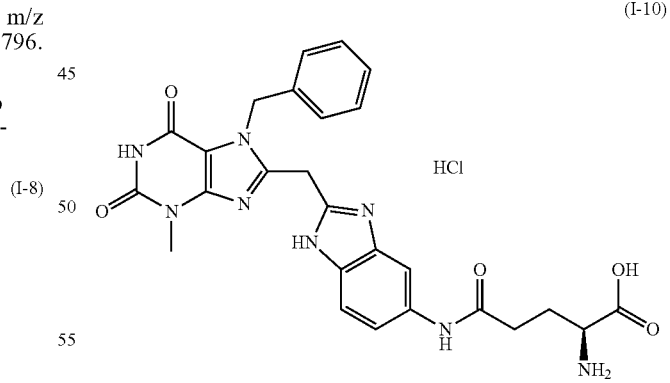

(I-10)

LCMS (method 1): R$_t$=0.663 min; HRMS (ESIpos): m/z [M+H]$^+$ calcd for C$_{26}$H$_{26}$N$_8$O$_5$, 531.2099 found, 531.2110. $^1$H NMR (600 MHz, DMSO-d$_6$) δ 11.27 (s, 1H), 10.44 (s, 1H), 8.51-8.44 (s, 3H), 8.17 (s, 1H), 7.59 (d, J=8.8 Hz, 1H), 7.50-7.46 (m, 1H), 7.31-7.27 (m, 2H), 7.26-7.20 (m, 3H), 5.69 (s, 2H), 4.72-4.65 (m, 2H), 4.00-3.95 (m, 1H), 3.34 (s, 3H, overlay H$_2$O peak), 2.70-2.64 (m, 1H), 2.50 (m, 1H, overlay DMSO peak), 2.18-2.10 (m, 2H).

Example 11: 7-benzyl-8-[(6-bromo-1,3-benzodiazol-2-yl)methyl]-3-methyl-2,3,6,7-tetrahydro-1H-purine-2,6-dione (KM-05-100)

(I-11)

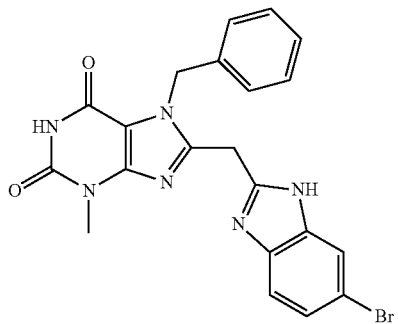

LCMS (method 2): $R_t$=0.954 min; MS (ESIpos) m/z=465.1 [M+H]$^+$.

Example 12: 7-benzyl-3-cyclopropyl-8-((6-fluoro-1H-benzo[d]imidazol-2-yl)methyl)-1H-purine-2,6(3H,7H)-dione (KM-05-126)

(I-12)

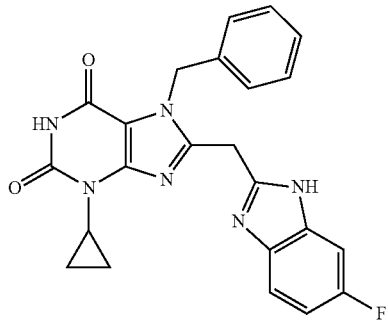

LCMS (method 1): $R_t$=1.104 min; HRMS (ESIpos): m/z [M+H]$^+$ calcd for $C_{23}H_{19}FN_6O_2$, 431.1632 found, 431.1630. $^1$H NMR (600 MHz, DMSO-d$_6$) δ 12.53 (s, 1H), 11.14 (s, 1H), 7.58-7.51 (m, 1H), 7.38-7.32 (m, 3H), 7.31-7.28 (m, 1H), 7.25 (d, J=7.3 Hz, 2H), 7.10-7.04 (m, 1H), 5.68 (s, 2H), 4.46 (s, 2H), 2.94-2.90 (m, 1H), 1.06-1.00 (m, 4H).

Example 13: 7-benzyl-3-cyclopropyl-8-((6-methoxy-1H-benzo[d]imidazol-2-yl)methyl)-1H-purine-2,6(3H,7H)-dione (KM-05-125)

(I-13)

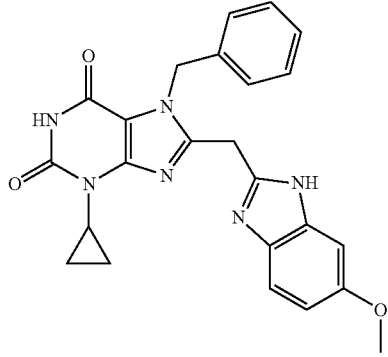

LCMS (method 1): $R_t$=1.046 min; HRMS (ESIpos): m/z [M+H]$^+$ calcd for $C_{24}H_{22}N_6O_3$, 443.1832 found, 443.1842. $^1$H NMR (600 MHz, DMSO-d$_6$) δ 12.29 (s, 1H), 11.13 (s, 1H), 7.44 (d, J=8.8 Hz, 1H), 7.39-7.35 (m, 2H), 7.34-7.30 (m, 1H), 7.28 (d, J=7.5 Hz, 2H), 7.07 (s, 1H), 6.84 (dd, J=2.6, 8.7 Hz, 1H), 5.69 (s, 2H), 4.41 (s, 2H), 2.95-2.89 (m, 1H), 1.05-0.99 (m, 4H).

Example 14: 7-benzyl-3-ethyl-8-((6-ethoxy-1H-benzo[d]imidazol-2-yl)methyl)-1H-purine-2,6(3H,7H)-dione (KM-05-179)

(I-201)

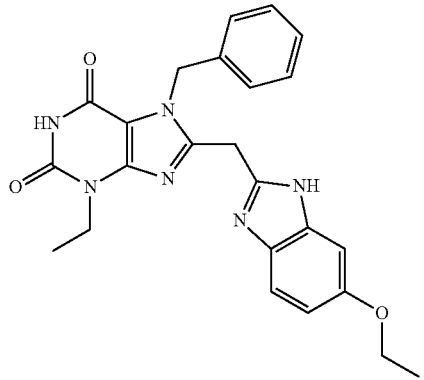

LCMS (method 1): $R_t$=1.092 min; HRMS (ESIpos): m/z [M+Na]$^+$ calcd for $C_{24}H_{26}N_6O_3$, 467.1818 found, 467.1808. $^1$H NMR (600 MHz, DMSO-d$_6$) δ 12.29 (s, 1H), 11.23 (s, 1H), 7.43 (d, J=8.6 Hz, 1H), 7.39-7.35 (m, 2H), 7.34-7.32 (m, 1H), 7.31-7.28 (m, 2H), 7.05 (s, 1H), 6.83 (dd, J=2.5, 8.7 Hz, 1H), 5.69 (s, 2H), 4.42 (s, 2H), 4.08 (q, J=7.0 Hz, 2H), 4.00 (q, J=7.2 Hz, 2H), 1.40 (t, J=7.0 Hz, 3H), 1.26 (t, J=7.1 Hz, 3H).

Example 15: 8-((6-(2-hydroxyethoxy)-1H-benzo[d]imidazol-2-yl)methyl)-7-benzyl-3-cyclopropyl-1H-purine-2,6(3H,7H)-dione (KM-05-135)

(I-15)

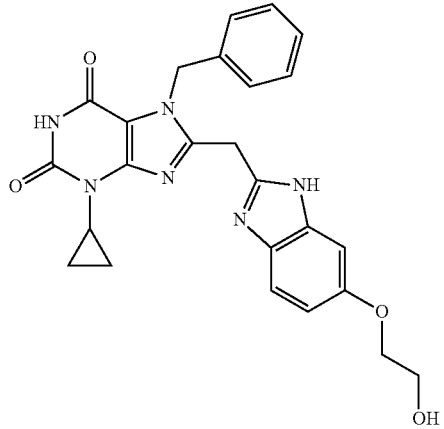

LCMS (method 1): $R_t$=0.979 min; HRMS (ESIpos): m/z [M+H]$^+$ calcd for $C_{25}H_{24}N_6O_4$, 473.1937 found, 473.1939. $^1$H NMR (300 MHz, DMSO-d$_6$) δ 12.20 (s, 1H), 11.08 (s, 1H), 7.33-7.23 (m, 3H), 7.20 (d, J=8.2 Hz, 2H), 7.07-6.84 (m, 2H), 6.78 (dd, J=2.1, 8.8 Hz, 1H), 5.61 (s, 2H), 4.86 (t, J=5.6 Hz, 1H), 4.33 (s, 2H), 3.97 (t, J=5.1 Hz, 2H), 3.76-3.68 (m, 2H), 2.88-2.81 (m, 1H), 1.00-0.91 (m, 4H).

Example 16: 2-((7-benzyl-3-cyclopropyl-2,3,6,7-tetrahydro-2,6-dioxo-1H-purin-8-yl)methyl)-3H-benzo[d]imidazole-5-carbonitrile (KM-05-127)

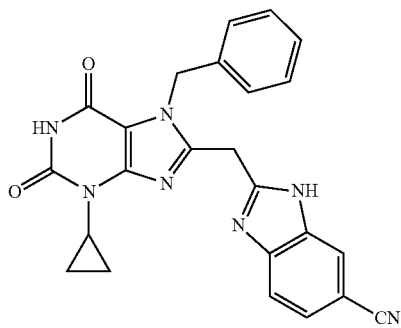

(I-16)

LCMS (method 1): R$_t$=1.147 min; HRMS (ESIpos): m/z [M+H]$^+$ calcd for C$_{24}$H$_{19}$N$_7$O$_2$, 438.1673 found, 438.1668. $^1$H NMR (300 MHz, DMSO-d$_6$) δ 12.86 (s, 1H), 11.10 (s, 1H), 8.14-7.92 (m, 1H), 7.73-7.47 (m, 2H), 7.32-7.11 (m, 5H), 5.60 (s, 2H), 4.48 (s, 2H), 2.90-2.79 (m, 1H), 1.00-0.90 (m, 4H).

Example 17: 2-((7-benzyl-3-cyclopropyl-2,3,6,7-tetrahydro-2,6-dioxo-1H-purin-8-yl)methyl)-3H-benzo[d]imidazole-5-carboxylate (KM-05-128)

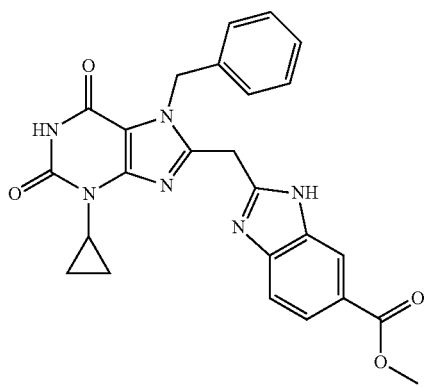

(I-17)

LCMS (method 1): R$_t$=1.136 min; HRMS (ESIpos): m/z [M+H]$^+$ calcd for C$_{25}$H$_{22}$N$_6$O$_4$, 471.1775 found, 471.1783. 1H NMR (600 MHz, DMSO-d$_6$) δ 12.75 (s, 1H), 11.15 (s, 1H), 8.20 and 8.12 (s, 1H, tautomers), 7.88 and 7.83 (d, J=8.7 Hz, 1H, tautomers), 7.69 and 7.59 (d, J=8.5, 1H, tautomers), 7.34-7.31 (m, 2H), 7.29-7.24 (m, 3H), 5.69 (s, 2H), 4.53 (s, 2H), 3.93 (s, 3H), 2.95-2.89 (m, 1H), 1.04-1.00 (m, 4H).

Example 18: 8-((1H-benzo[d]imidazol-2-yl)methyl)-7-benzyl-3-ethyl-1H-purine-2,6(3H,7H)-dione (AG-01-128)

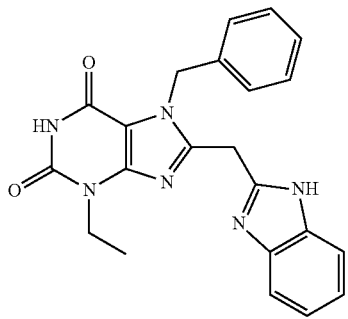

(I-202)

LCMS (method 1): R$_t$=1.039 min; HRMS (ESIpos): m/z [M+H]$^+$ calcd for C$_{22}$H$_{20}$N$_6$O$_2$, 401.1721 found, 401.1723. $^1$H NMR (300 MHz, DMSO-d$_6$) δ 12.39 (s, 1H), 11.19 (s, 1H), 7.49 (dd, J=3.7, 5.8 Hz, 2H), 7.32-7.20 (m, 5H), 7.17-7.11 (m, 2H), 5.63 (s, 2H), 4.40 (s, 2H), 3.92 (q, J=7.0 Hz, 2H), 1.17 (t, J=7.1 Hz, 3H).

Example 19: 7-benzyl-3-cyclopropyl-8-((6-hydroxy-1H-benzo[d]imidazol-2-yl)methyl)-1H-purine-2,6(3H,7H)-dione (KM-05-130)

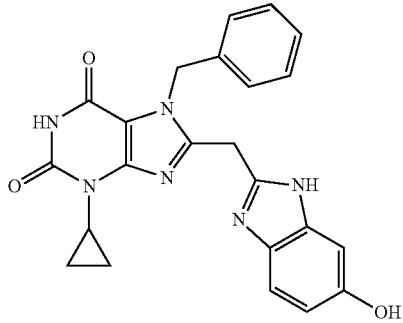

(I-19)

LCMS (method 1): R$_t$=0.968 min; HRMS (ESIpos): m/z [M+H]$^+$ calcd for C$_{23}$H$_{20}$N$_6$O$_3$, 429.1670 found, 429.1672. $^1$H NMR (300 MHz, DMSO-d$_6$) δ 11.09 (s, 1H), 9.10 (s, 1H), 7.34-7.24 (m, 4H), 7.23-7.17 (m, 2H) 6.80 (d, J=2.4 Hz, 1H), 6.64 (dd, J=2.4, 8.6 Hz, 1H), 5.61 (s, 2H), 4.31 (s, 2H), 3.35 (s, 1H), 2.89-2.79 (m, 1H), 0.99-0.89 (m, 4H).

Example 20: 7-benzyl-8-((6-(dimethylamino)-5-fluoro-1H-benzo[d]imidazol-2-yl)methyl)-3-ethyl-1H-purine-2,6(3H,7H)-dione (KM-05-173)

Example 22: 7-benzyl-3-ethyl-8-((5-fluoro-6-morpholino-1H-benzo[d]imidazol-2-yl)methyl)-1H-purine-2,6(3H,7H)-dione (KM-05-174)

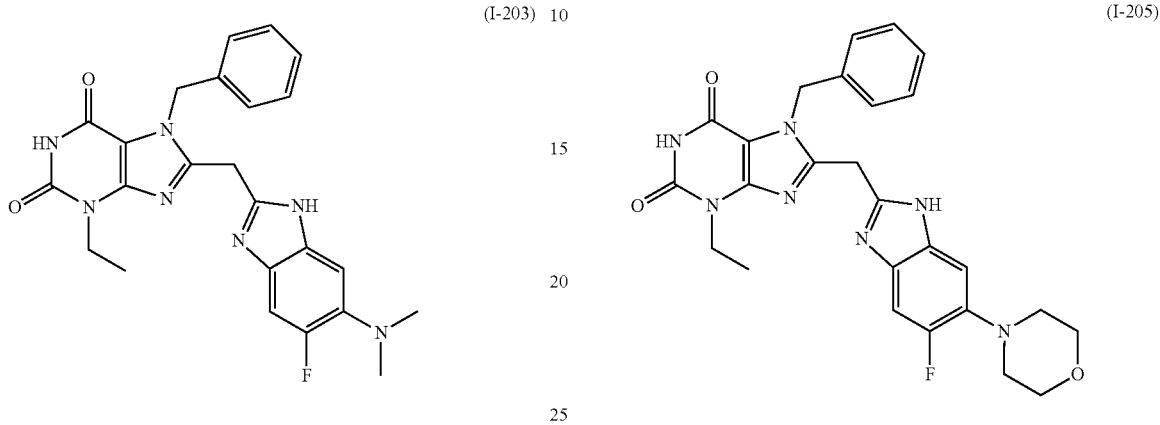

(I-203)

(I-205)

LCMS (method 1): $R_f$=1.033 min; HRMS (ESIpos): m/z [M+Na]$^+$ calcd for $C_{24}H_{24}FN_7O_2$, 484.1863 found, 484.1868. $^1$H NMR (300 MHz, DMSO-d$_6$) δ 11.18 (s, 1H), 7.31-7.18 (m, 6H), 7.04 (d, J=8.1 Hz, 1H), 5.60 (s, 2H), 4.35 (s, 2H), 3.92 (q, J=7.1 Hz, 2H), 2.72 (s, 6H), 1.18 (t, J=7.0 Hz, 3H).

LCMS (method 1): $R_f$=1.082 HRMS (ESIpos): m/z [M+H]$^+$ calcd for $C_{26}H_{26}FN_7O_3$, 504.2159 found, 504.2130. $^1$H NMR (300 MHz, DMSO-d$_6$) δ 11.18 (s, 1H), 7.33-7.24 (m, 4H), 7.22-7.17 (m, 2H), 7.09 (d, J=7.8 Hz, 1H), 5.60 (s, 2H), 4.37 (s, 2H), 3.92 (q, J=7.1 Hz, 2H), 3.78-3.71 (m, 4H), 2.98-2.91 (m, 4H), 1.18 (t, J=7.1 Hz, 3H).

Example 21: 7-benzyl-8-((6-hydroxy-1H-benzo[d]imidazol-2-yl)methyl)-3-propyl-1H-purine-2,6(3H,7H)-dione (KM-05-185)

Example 23: 7-benzyl-3-cyclopropyl-8-(5H-[1,3]dioxolo[4,5-f]benzimidazol-6-ylmethyl)purine-2,6-dione (KM-05-139)

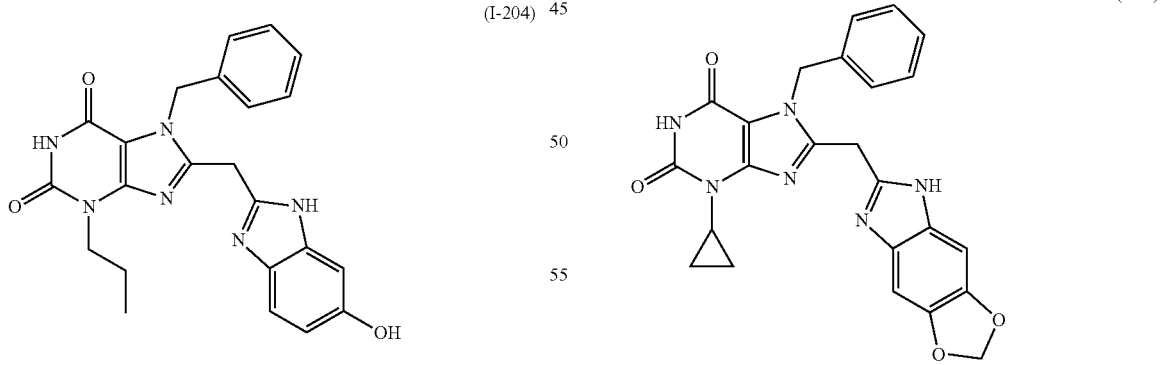

(I-204)

(I-23)

LCMS (method 1): $R_f$=1.013 min; HRMS (ESIpos): m/z [M+H]$^+$ calcd for $C_{23}H_{22}N_6O_3$, 431.1832 found, 431.1844. $^1$H NMR (300 MHz, DMSO-d$_6$) δ 11.96 (s, 1H), 11.18 (s, 1H), 9.16 (s, 1H), 7.36-7.18 (m, 6H), 6.78 (s, 1H), 6.63 (d, J=9.0 Hz, 1H), 5.61 (s, 2H), 4.31 (s, 2H), 3.85 (t, J=7.7 Hz, 2H), 1.73-1.57 (m, 2H), 0.85 (t, J=7.5 Hz, 3H).

LCMS (method 1): $R_f$=1.029 min; HRMS (ESIpos): m/z [M+H]$^+$ calcd for $C_{24}H_{20}N_6O_4$, 457.1619 found, 457.1612 $^1$H NMR (300 MHz, DMSO-d$_6$) δ 12.21 (s, 1H), 11.08 (s, 1H), 7.33-7.23 (m, 3H), 7.21-7.15 (m, 2H), 7.01 (s, 2H), 5.97 (s, 2H), 5.60 (s, 2H), 4.30 (s, 2H), 2.91-2.78 (m, 1H), 1.00-0.91 (m, 4H).

Example 24: 7-benzyl-3-ethyl-8-(5H-[1,3]dioxolo[4,5-f]benzimidazol-6-ylmethyl)purine-2,6-dione (KM-05-166)

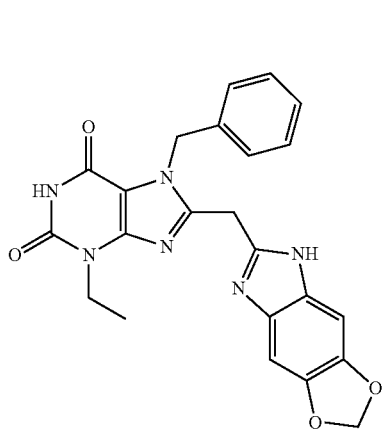

(I-206)

LCMS (method 1): R$_t$=1.032 min; HRMS (ESIpos): m/z [M+H]$^+$ calcd for C$_{23}$H$_{20}$N$_6$O$_4$, 445.1619 found, 445.1618. $^1$H NMR (300 MHz, DMSO-d$_6$) δ 12.23 (s, 1H), 11.17 (s, 1H), 7.33-7.24 (m, 3H), 7.21 (d, J=7.6 Hz, 2H), 7.06-6.95 (m, 2H), 5.96 (s, 2H), 5.60 (s, 2H), 4.31 (s, 2H), 3.92 (q, J=7.0 Hz, 2H), 1.18 (t, J=7.1 Hz, 3H).

Example 25: 8-((1H-benzo[d]imidazol-2-yl)methyl)-7-benzyl-3-propyl-1H-purine-2,6(3H,7H)-dione (MW-01-157)

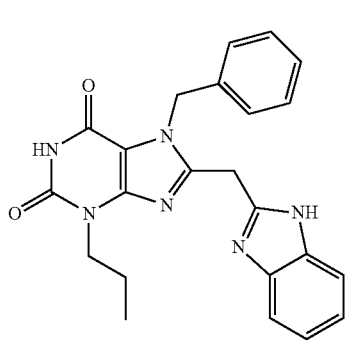

(I-207)

LCMS (method 1): R$_t$=1.077 min; HRMS (ESIpos): m/z [M+H]$^+$ calcd for C$_{23}$H$_{22}$N$_6$O$_2$, 415.1882 found, 415.1896. $^1$H NMR (300 MHz, DMSO-d$_6$) δ 12.38 (s, 1H), 11.18 (s, 1H), 7.53 (d, J=7.0 Hz, 1H), 7.44 (d, J=5.9 Hz, 1H), 7.32-7.20 (m, 5H), 7.17-7.10 (m, 2H), 5.62 (s, 2H), 4.40 (s, 2H), 3.84 (t, J=7.5 Hz, 2H), 1.74-1.55 (m, 2H), 0.85 (t, J=7.4 Hz, 3H).

Example 26: 8-((1H-imidazo[4,5-b]pyridin-2-yl)methyl)-7-benzyl-3-ethyl-1H-purine-2,6(3H,7H)-dione (KM-05-180)

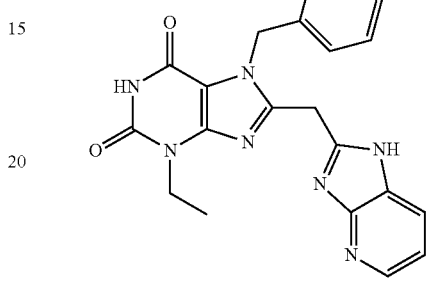

(I-208)

LCMS (method 1): R$_t$=0.999 min; HRMS (ESIpos): m/z [M+H]$^+$ calcd for C$_{21}$H$_{19}$N$_7$O$_2$, 402.1673 found, 402.1664. $^1$H NMR (300 MHz, DMSO-d$_6$) δ 11.18 (s, 1H), 8.27 (s, 1H), 7.89 (s, 1H), 7.30-7.16 (m, 6H), 5.62 (s, 2H), 4.45 (s, 2H), 3.92 (q, J=7.1 Hz, 2H), 1.18 (t, J=7.0 Hz, 3H).

Example 27: 7-benzyl-3-propyl-8-(5H-[1,3]dioxolo[4,5-f]benzimidazol-6-ylmethyl)purine-2,6-dione (KM-05-193)

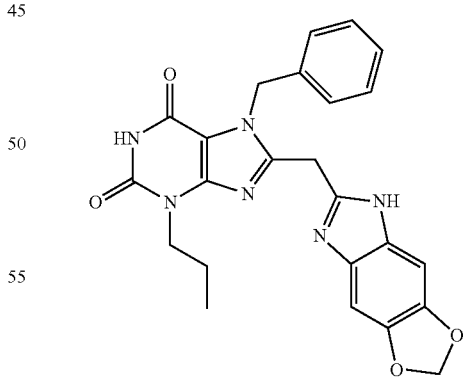

(I-209)

LCMS (method 1): R$_t$=1.066 min; HRMS (ESIpos): m/z [M+H]$^+$ calcd for C$_{24}$H$_{23}$N$_6$O$_4$, 459.1781 found, 459.1775. $^1$H NMR (300 MHz, DMSO-d$_6$) δ 12.22 (s, 1H), 11.17 (s, 1H), 7.33-7.23 (m, 3H), 7.20 (d, J=7.4 Hz, 2H), 7.00 (s, 2H), 5.96 (s, 2H), 5.60 (s, 2H), 4.31 (s, 2H), 3.84 (t, J=7.4 Hz, 2H), 1.71-1.57 (m, 2H), 0.85 (t, J=7.4 Hz, 3H).

Example 28: 8-((1H-benzo[d]imidazole-2-yl)methyl)-3-ethyl-7-(4-fluorobenzyl)-3,7-dihydro-1H-purine-2,6-dione (KM-06-011)

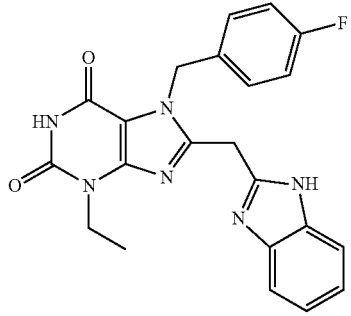

(I-210)

LCMS (method 1): $R_t$=1.047 min; HRMS (ESIpos): m/z [M+H]$^+$ calcd for $C_{22}H_{19}FN_6O_2$, 419.1626 found, 419.1625. $^1$H NMR (300 MHz, DMSO-d$_6$) δ 12.37 (s, 1H), 11.20 (s, 1H), 7.54-7.39 (m, 2H), 7.30-7.24 (m, 2H), 7.16-7.03 (m, 4H), 5.59 (s, 2H), 4.43 (s, 2H), 3.92 (q, J=7.1 Hz, 2H), 1.17 (t, J=7.1 Hz, 3H).

Example 29: 8-((6-(1H-pyrazol-3-yl)-1H-benzo[d]imidazol-2-yl)methyl)-7-benzyl-3-ethyl-1H-purine-2,6(3H,7H)-dione (KM-06-20)

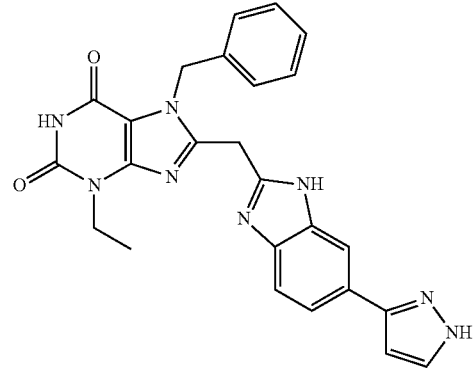

(I-211)

LCMS (method 1): $R_t$=1.038 min; HRMS (ESIpos): m/z [M+H]$^+$ calcd for $C_{25}H_{22}N_8O_2$, 467.1938 found, 467.1933. $^1$H NMR (300 MHz, DMSO-d$_6$) δ 12.79 (s, 1H), 12.44 (s, 1H), 11.19 (s, 1H), 7.97-7.51 (m, 4H), 7.39-7.22 (m, 5H), 6.70 (s, 1H), 5.65 (s, 2H), 4.42 (s, 2H), 4.04-3.84 (m, 2H), 1.19 (t, J=7.2 Hz, 3H).

Examples 30-56

Benzimidazolyl xanthines according to general formula I with Q=S or NH, Z=NH, and X=C were synthesized according to general procedure B.

General Procedure B

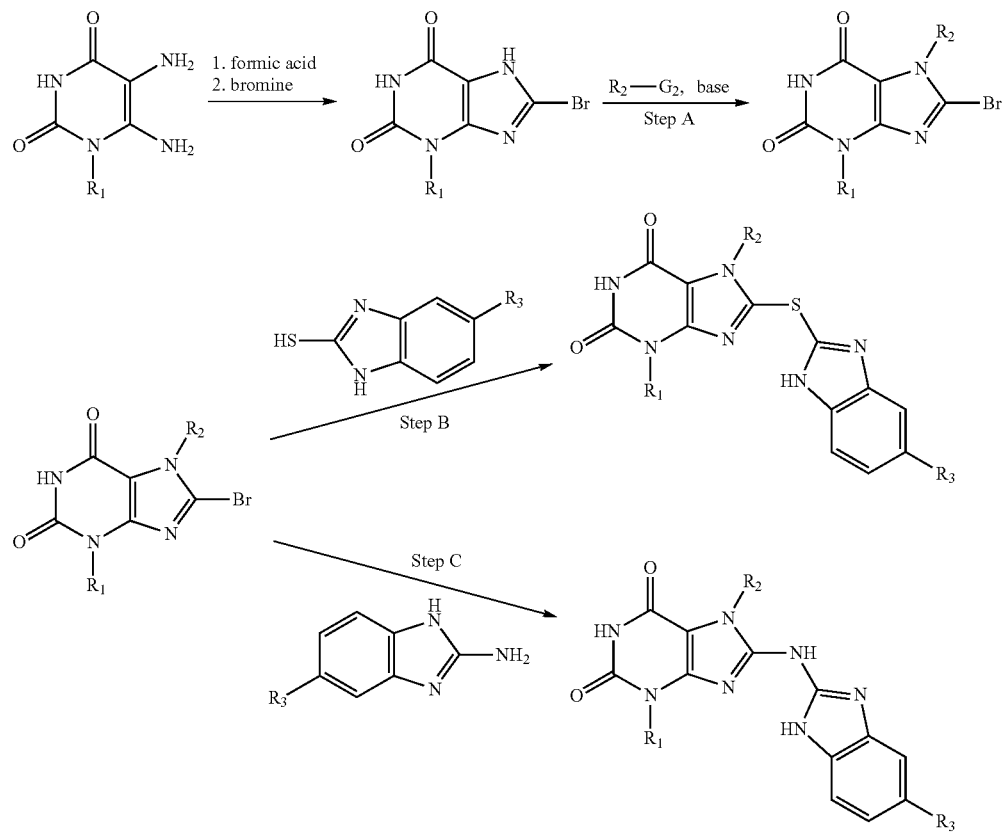

Synthesis of 8-bromo-3-alkyl-1H-purine-2,6(3H,7H)-dione

The title compound was prepared by adding to 5,6-diamino-1-alkyl-1,2,3,4-tetrahydropyrimidine-2,4-dione (19.2 mmol, alkyl=$R_1$) to 50 ml $H_2O$ and 1.02 ml (26.9 mmol) formic acid. The reaction mixture was refluxed for 2 h and 3 ml 1N NaOH was added and the temperature was kept at 100° C. for 16 h. After cooling to 0° C. in an ice bath the reaction mixture was acidified with acetic acid to pH=6. The resulting solid was filtered off and washed with $H_2O$ and dried to give 2.5 g (15 mmol, 78%) of the product. The crude product was dissolved in 50 ml acetic acid and 2.47 g (30.1 mmol) sodium acetate was added. After addition of 0.925 ml (18.06 mmol) bromine the reaction mixture was stirred for 3 h at 66° C. The suspension was cooled to RT, filtered off and washed with acetic acid (1×), $H_2O$ (4×) and Ether (2×). The resulting solid was dried to give a yellowish solid.

Step A:

The starting material (2 mmol) obtained in the previous step was dissolved in 20 ml DMF and to a reaction vessel containing a magnetic stirring bar 1.1 ml DIPEA (6.2 mmol) was added followed by addition of alkylation reagent $R_2$-$G_2$ (2 mmol), and the mixture was heated to 50° C. under stirring. After 2 h the reaction mixture was cooled to RT and DMF was removed under reduced pressure. The solid was homogenized in aqueous solution by means of sonification, filtered off, washed 2× with ethanol and ether and dried under vacuum.

Step B:

The product from step A (0.15 mol) was dissolved in 2.5 ml DMF. 2-Mercapto-benzimidazole (0.16 mmol) and 0.82 mmol KOH were added and the reaction mixture was heated for 2 h to 150° C. by using microwave irradiation. After cooling to RT the solvent was removed under reduced pressure and the resulting solid was suspended with $H_2O$. The mixture was extracted three times with 10 ml EtOAc. The combined organic phases were dried over $Na_2SO_4$ and the solvent was removed under reduced pressure. Ether was added and the product precipitated as a white solid, was filtered off and washed with ether.

Step C:

The product from step A (015 mol) was dissolved in 2.5 ml DMF. 2-Amino-benzimidazole (0.16 mmol) and 0.8 mmol KOH were added and the reaction mixture was heated for 2 h to 150° C. by using microwave irradiation. After cooling to RT the solvent was removed under reduced pressure and the resulting solid was suspended with $H_2O$. The mixture was extracted three times with 50 ml EtOAc. The combined organic phases were dried over $Na_2SO_4$ and the solvent was removed under reduced pressure. Ether was added and the product precipitated as a white solid, was filtered off and washed with ether.

Example 30: 8-(1H-1,3-benzodiazol-2-ylsulfanyl)-7-benzyl-3-methyl-2,3,6,7-tetrahydro-1H-purine-2,6-dione (KM 406)

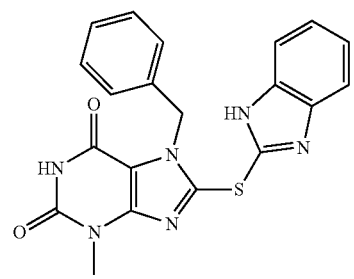

(I-24)

Synthesis of 8-bromo-3-methyl-1H-purine-2,6(3H,7H)-dione

The title compound was prepared by adding to 5,6-diamino-1-methyl-1,2,3,4-tetrahydropyrimidine-2,4-dione (3 g, 19.2 mmol) to 50 ml $H_2O$ and 1.02 ml (26.9 mmol) formic acid. The reaction mixture was refluxed for 2 h and 3 ml 1N NaOH was added and the temperature was kept at 100° C. for 16 h. After cooling to 0° C. in an ice bath the reaction mixture was acidified with acetic acid to pH=6. The resulting solid was filtered off and washed with $H_2O$ and dried to give 2.5 g (15 mmol, 78%) of the product. The crude product was dissolved in 50 ml acetic acid and 2.47 g (30.1 mmol) sodium acetate was added. After addition of 0.925 ml (18.06 mmol) bromine the reaction mixture was stirred for 3 h at 66° C. The suspension was cooled to RT, filtered off and washed with acetic acid (1×), $H_2O$ (4×) and Ether (2×). The resulting solid was dried to give a yellowish solid. Yield: 3.11 g (84%).

LCMS (method 2): $R_t$=0.420 min; MS (ESIpos) m/z=245.0 $[M+H]^+$ $^1$H NMR (300 MHz, DMSO-$d_6$) δ=11.20 (s, 1H), 3.31 (s, 3H).

Synthesis of 7-benzyl-8-bromo-3-methyl-1H-purine-2,6(3H,7H)-dione

According to Step A in procedure B, 8-Bromo-3-methyl-1H-purine-2,6(3H,7H)-dione (500 mg, 2.04 mmol) was dissolved in 20 ml DMF and 1.07 ml DIPEA (6.12 mmol) and benzylbromide (243 µl, 2.041 mmol) was added under stirring at RT. The reaction mixture was heated to 50° C. and stirred for 2 h. The reaction was cooled to RT and the DMF was removed under reduced pressure. The crude product was homogenized in aqueous solution by means of sonification, filtered off, washed 2× with ethanol and ether and dried under vacuum to give 7-benzyl-8-bromo-3-methyl-1H-purine-2,6(3H,7H)-dione as white solid. Yield: 600 mg (87%).

LCMS (method 1): $R_t$=1.194 min; HRMS (ESIpos): m/z $[M+H]^+$ calcd for $C_{13}H_{11}BrN_4O_2$, 335.0138 found, 335.0185. $^1$H NMR (300 MHz, DMSO-$d_6$) δ=11.34 (s, 1H), 7.43-7.20 (m, 5H), 5.48 (s, 2H), 3.33 (s, 3H).

Synthesis of 8-(1H-1,3-benzodiazol-2-ylsulfanyl)-7-benzyl-3-methyl-2,3,6,7-tetrahydro-1H-purine-2,6-dione According to Step B in procedure B, 7-benzyl-8-bromo-3-methyl-1H-purine-2,6(3H,7H)-dione (100 mg, 0.298 mmol) and 49 mg (0.328 mmol) 2-Mercapto-benzimidazole was added together with 92 mg KOH in 2.5 ml DMF. The reaction mixture was heated for 2 h at 150° C. by using microwave irradiation. After cooling to RT DMF was removed under reduced pressure and the resulting solid was suspended with H$_2$O. The mixture was extracted three times with 10 ml EtOAc. The combined organic phases were dried over Na$_2$SO$_4$ and the solvent was removed under reduced pressure. After addition of 10 ml ether the product precipitated as white solid, was filtered off and washed with ether. Yield: 40 mg (33%).

LCMS (method 1): R$_t$=1.202 min; HRMS (ESIpos): m/z [M+H]$^+$ calcd for C$_{20}$H$_{16}$N$_6$O$_2$S, 405.1128 found, 405.1133. $^1$H NMR (300 MHz, DMSO-d$_6$) δ 11.44 (s, 1H), 7.54 (dd, J=3.1, 6.1 Hz, 2H), 7.30-7.23 (m, 6H), 7.22-7.16 (m, 1H), 5.66 (s, 2H), 2.53 (s, 3H).

Example 31: 7-benzyl-8-[(5-methoxy-1H-1,3-benzodiazol-2-yl)sulfanyl]-3-methyl-2,3,6,7-tetrahydro-1H-purine-2,6-dione (KM 422)

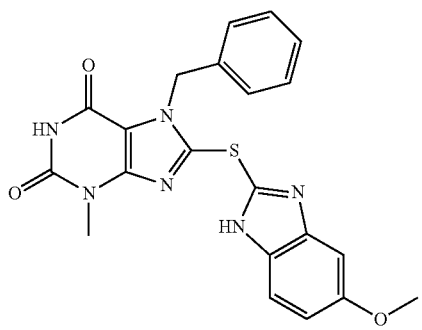

(I-25)

LCMS (method 1): R$_t$=1.199 min; HRMS (ESIpos): m/z [M+H]$^+$ calcd for C$_{21}$H$_{18}$N$_6$O$_3$S, 435.1234 found, 435.1220. $^1$H NMR (300 MHz, DMSO-d$_6$) δ 12.73 (s, 1H), 11.39 (s, 1H), 7.39 (s, 1H), 7.31-7.24 (m, 5H), 6.98 (s, 1H), 6.82 (d, J=8.5 Hz, 1H), 5.63 (s, 2H), 3.76 (s, 3H), 3.31 (s, 3H).

Example 32: 7-benzyl-8-[(1-ethyl-1H-1,3-benzodiazol-2-yl)sulfanyl]-3-methyl-2,3,6,7-tetrahydro-1H-purine-2,6-dione (KM 423)

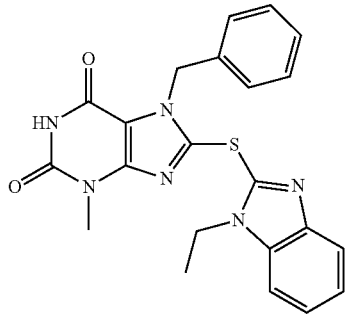

(I-26)

LCMS (method 1): R$_t$=1.292 min; HRMS (ESIpos): m/z [M+H]$^+$ calcd for C$_{22}$H$_{20}$N$_6$O$_2$S, 433.1441 found, 433.1427. $^1$H NMR (300 MHz, DMSO-d$_6$) δ 11.36 (s, 1H), 7.66-7.56 (m, 2H), 7.36-7.20 (m, 7H), 5.68 (s, 2H), 4.33 (q, J=7.5 Hz, 2H), 3.25 (s, 3H), 1.30 (t, J=7.4 Hz, 3H).

Example 33: 7-benzyl-3-methyl-8-[(5-methyl-1H-1,3-benzodiazol-2-yl)sulfanyl]-2,3,6,7-tetrahydro-1H-purine-2,6-dione (KM 424)

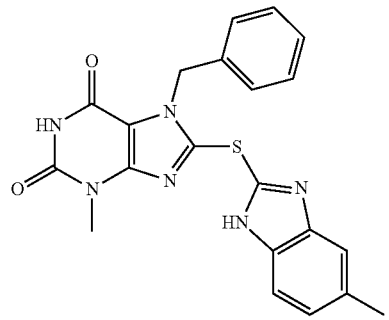

(I-27)

LCMS (method 1): R$_t$=1.239 min; HRMS (ESIpos): m/z [M+H]$^+$ calcd for C$_{21}$H$_{18}$N$_6$O$_2$S, 419.1285 found, 419.1286. $^1$H NMR (300 MHz, DMSO-d$_6$) δ 12.72 (s, 1H), 11.39 (s, 1H), 7.40-7.22 (s, 7H), 7.01 (d, J=7.4 Hz, 1H), 5.63 (s, 2H), 3.30 (s, 3H), 2.39 (s, 3H).

Example 34: 7-benzyl-8-[(5,6-dichloro-1H-1,3-benzodiazol-2-yl)sulfanyl]-3-methyl-2,3,6,7-tetrahydro-1H-purine-2,6-dione (KM 425)

(I-28)

LCMS (method 1): R$_t$=1.338 min; HRMS (ESIpos): m/z [M+H]$^+$ calcd for C$_{20}$H$_{14}$Cl$_2$N$_6$O$_2$S, 473.0349 found, 473.0348. $^1$H NMR (300 MHz, DMSO-d$_6$) δ 11.44 (s, 1H), 7.74 (s, 2H), 7.27-7.17 (m, 5H), 5.61 (s, 2H), 3.30 (s, 3H, overlay H$_2$O peak).

Example 35: 2-[(7-benzyl-3-methyl-2,6-dioxo-2,3,6,7-tetrahydro-1H-purin-8-yl)sulfanyl]-1H-1,3-benzodiazole-5-sulfonic acid (KM 427)

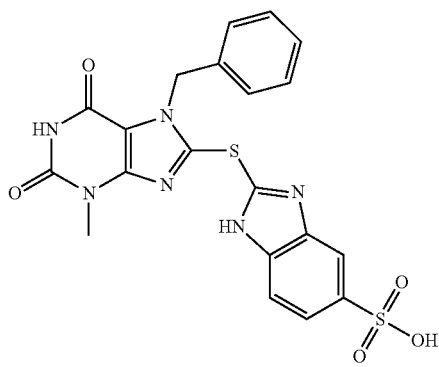
(I-29)

LCMS (method 1): $R_t$=1.023 min; HRMS (ESIpos): m/z [M+H]$^+$ calcd for $C_{20}H_{16}N_6O_5S_2$, 485.0696 found, 485.0699. $^1$H NMR (300 MHz, DMSO-d$_6$) δ 7.75 (s, 1H), 7.50 (d, J=7.7 Hz, 1H), 7.45-7.40 (m, 1H), 7.31-7.24 (s, 5H), 5.63 (s, 2H), 3.31 (s, 3H, overlay H$_2$O peak).

Example 36: 2-[(7-benzyl-3-methyl-2,6-dioxo-2,3,6,7-tetrahydro-1H-purin-8-yl)sulfanyl]-1H-1,3-benzodiazole-6-carboxylic acid (KM 429)

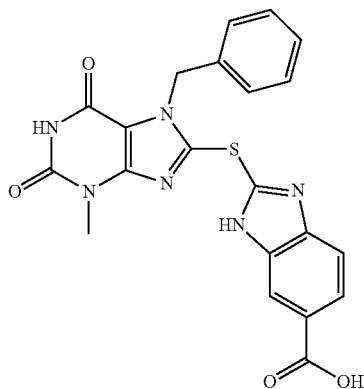
(I-30)

LCMS (method 1): $R_t$=1.135 min; HRMS (ESIpos): m/z [M+H]$^+$ calcd for $C_{21}H_{16}N_6O_4S$, 449.1027 found, 449.1022. $^1$H NMR (300 MHz, DMSO-d$_6$) δ 11.43 (s, 1H), 8.06 (s, 1H), 7.81 (d, J=8.5 Hz, 1H), 7.55 (d, J=8.5 Hz, 1H), 7.23 (d, J=4.1 Hz, 4H), 7.20-7.14 (m, 1H), 5.63 (s, 2H), 3.31 (s, 3H, overlay H$_2$O peak).

Example 37: 8-[(5-amino-1H-1,3-benzodiazol-2-yl)sulfanyl]-7-benzyl-3-methyl-2,3,6,7-tetrahydro-1H-purine-2,6-dione (KM 430)

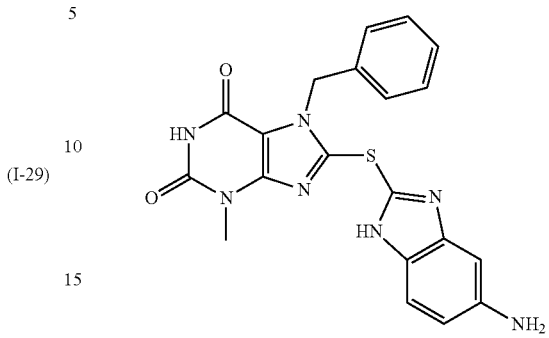
(I-31)

LCMS (method 1): $R_t$=0.982 min; HRMS (ESIpos): m/z [M+H]$^+$ calcd for $C_{20}H_{17}N_7O_2S$, 420.1237 found, 420.1244. $^1$H NMR (300 MHz, DMSO-d$_6$) δ 12.34 (s, 1H), 11.35 (s, 1H), 7.36-7.21 (m, 6H), 6.53 (d, J=10.6 Hz, 2H), 5.63 (s, 2H), 5.05 (s, 2H), 3.29 (s, 3H).

Example 38: 8-(1,3-benzothiazol-2-ylsulfanyl)-7-benzyl-3-methyl-2,3,6,7-tetrahydro-1H-purine-2,6-dione (KM 431)

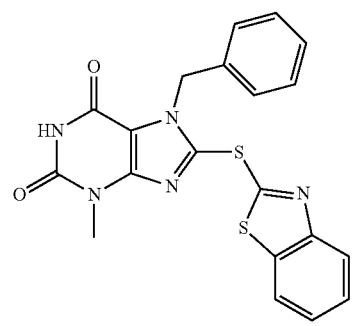
(I-32)

LCMS (method 1): $R_t$=1.351 min; HRMS (ESIpos): m/z [M+H]$^+$ calcd for $C_{20}H_{15}N_5O_2S_2$, 422.0740 found, 422.0753. $^1$H NMR (300 MHz, DMSO-d$_6$) δ 11.51 (s, 1H), 7.98 (d, J=7.8 Hz, 1H), 7.88 (d, J=8.0 Hz, 1H), 7.54-7.44 (m, 1H), 7.43-7.36 (m, 1H), 7.28-7.12 (m, 5H), 5.65 (s, 2H), 3.40 (s, 3H).

Example 39: 7-benzyl-8-{3H-imidazo[4,5-b]pyridin-2-ylsulfanyl}-3-methyl-2,3,6,7-tetrahydro-1H-purine-2,6-dione (KM 432)

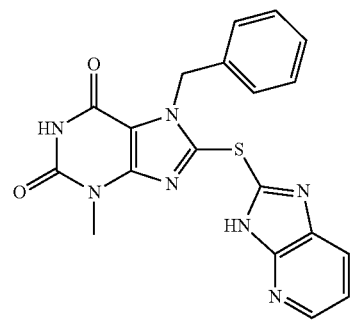
(I-33)

LCMS (method 1): R$_t$=1.066 min; HRMS (ESIpos): m/z [M+H]$^+$ calcd for C$_{19}$H$_{15}$N$_7$O$_2$S, 406.1081 found, 406.1067.

Example 40: 8-(1H-1,3-benzodiazol-2-ylsulfanyl)-3-methyl-7-[(5-methyl-1,3,4-oxadiazol-2-yl)methyl]-2,3,6,7-tetrahydro-1H-purine-2,6-dione (KM 435)

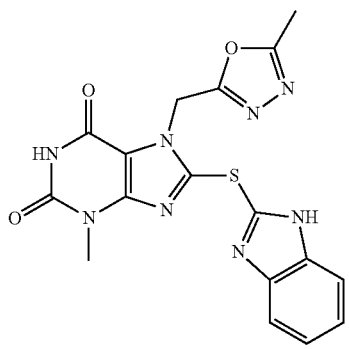

(I-34)

LCMS (method 1): R$_t$=1.041 min; HRMS (ESIpos): m/z [M+H]$^+$ calcd for C$_{17}$H$_{14}$N$_8$O$_3$S, 411.0982 found, 411.0976. $^1$H NMR (600 MHz, DMSO-d$_6$) δ 12.88 (s, 1H), 11.53 (s, 1H), 7.56 (d, J=8.7 Hz, 1H), 7.50 (d, J=7.0 Hz, 1H), 7.27 (d, J=8.5 Hz, 1H), 7.24 (d, J=7.6 Hz, 1H), 6.00 (s, 2H), 3.42 (s, 3H), 2.35 (s, 3H).

Example 41: 3-methyl-8-[(5-methyl-1H-1,3-benzodiazol-2-yl)sulfanyl]-7-(1,3-thiazol-5-ylmethyl)-2,3,6,7-tetrahydro-1H-purine-2,6-dione (KM 446)

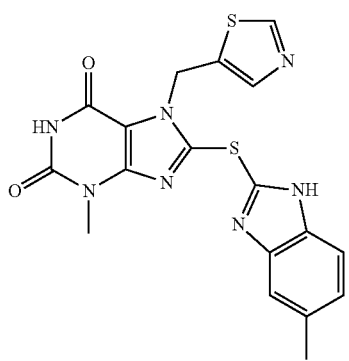

(I-35)

LCMS (method 1): R$_t$=1.128 min; HRMS (ESIpos): m/z [M+H]$^+$ calcd for C$_{18}$H$_{15}$N$_7$O$_2$S$_2$, 426.0801 found, 426.0797. $^1$H NMR (300 MHz, DMSO-d$_6$) δ 12.72 (s, 1H), 11.47 (s, 1H), 9.02 (s, 1H), 7.94 (s, 1H), 7.42 and 7.23 (d, J=8.2 Hz, 1H, tautomers), 7.35 and 7.23 (s, 1H, tautomers) (s, 1H), 7.07-6.96 (m, 1H), 5.87 (s, 2H), 3.28 (s, 3H), 2.39 (s, 3H).

Example 42: 8-(1H-1,3-benzodiazol-2-ylsulfanyl)-3-methyl-7-(1,3-thiazol-2-ylmethyl)-2,3,6,7-tetrahydro-1H-purine-2,6-dione (KM 447)

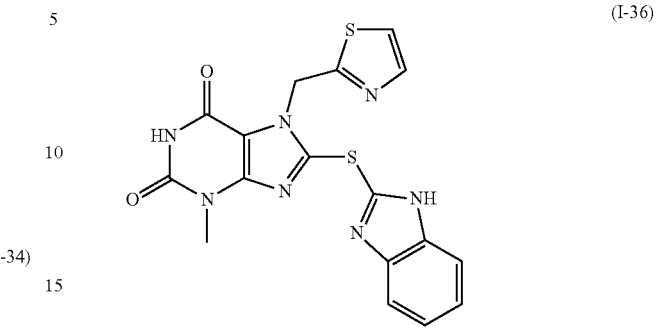

(I-36)

LCMS (method 1): R$_t$=1.108 min; HRMS (ESIpos) m/z [M+H]$^+$. calcd for C$_{17}$H$_{13}$N$_7$O$_2$S$_2$, 412.0645 found, 412.0627.

Example 43: 8-(1H-1,3-benzodiazol-2-ylsulfanyl)-3-methyl-7-(1,3-oxazol-5-ylmethyl)-2,3,6,7-tetrahydro-1H-purine-2,6-dione (KM 448)

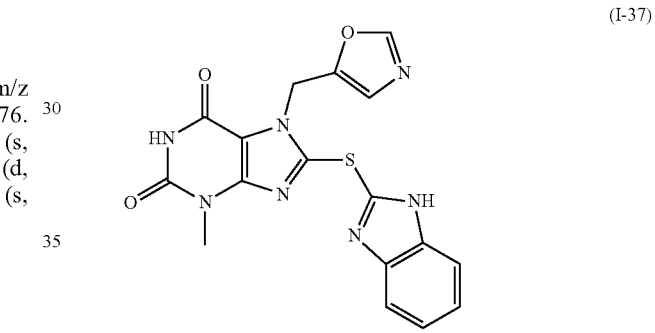

(I-37)

LCMS (method 1): R$_t$=1.078 min; HRMS (ESIpos): m/z [M+H]$^+$ calcd for C$_{17}$H$_{13}$N$_7$O$_3$S, 396.0873 found, 396.0874. $^1$H NMR (300 MHz, DMSO-d$_6$) δ 12.85 (s, 1H), 11.44 (s, 1H), 8.05 (s, 1H), 7.52 (d, J=7.5 Hz, 1H), 7.44 (d, J=7.4 Hz, 1H), 7.26-7.12 (m, 2H), 7.08 (s, 1H), 5.85 (s, 2H), 3.33 (s, 3H).

Example 44: 8-(1H-1,3-benzodiazol-2-ylsulfanyl)-7-(furan-2-ylmethyl)-3-methyl-2,3,6,7-tetrahydro-1H-purine-2,6-dione (KM 449)

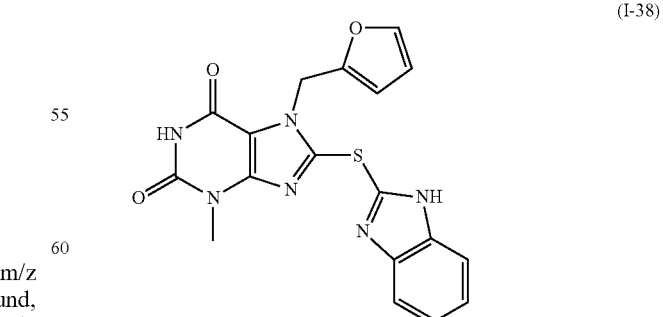

(I-38)

LCMS (method 1): R$_t$=1.164 min; HRMS (ESIpos): m/z [M+H]$^+$ calcd for C$_{18}$H$_{14}$N$_6$O$_3$S, 395.0921 found, 395.0922. $^1$H NMR (300 MHz, DMSO-d$_6$) δ 12.80 (s, 1H), 11.40 (s, 1H), 7.61-7.40 (m, 3H), 7.24-7.14 (m, 2H), 6.48-6.33 (m, 2H), 5.65 (s, 2H), 3.29 (s, 3H).

Example 45: 7-(furan-2-ylmethyl)-3-methyl-8-[(5-methyl-1H-1,3-benzodiazol-2-yl)sulfanyl]-2,3,6,7-tetrahydro-1H-purine-2,6-dione (KM 450)

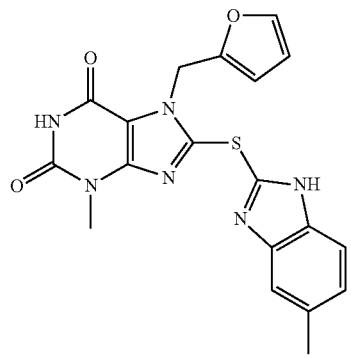

(I-39)

LCMS (method 1): $R_t$=1.203 min; HRMS (ESIpos): m/z [M+H]$^+$ calcd for $C_{19}H_{16}N_6O_3S$, 409.1077 found, 409.1069. $^1$H NMR (300 MHz, DMSO-d$_6$) δ 12.71 (s, 1H), 11.38 (s, 1H), 7.52 (s, 1H), 7.47-7.20 (m, 2H), 7.01 (d, J=7.4 Hz, 1H), 6.45 (d, J=3.2 Hz, 1H), 6.41-6.33 (m, 1H), 5.64 (s, 2H), 3.27 (s, 3H), 2.39 (s, 3H).

Example 46: (2S)-2-amino-3-({2-[(7-benzyl-3-methyl-2,6-dioxo-2,3,6,7-tetrahydro-1H-purin-8-yl)sulfanyl]-1H-1,3-benzodiazol-5-yl}carbamoyl)propanoic acid hydrochloride (KM 477)

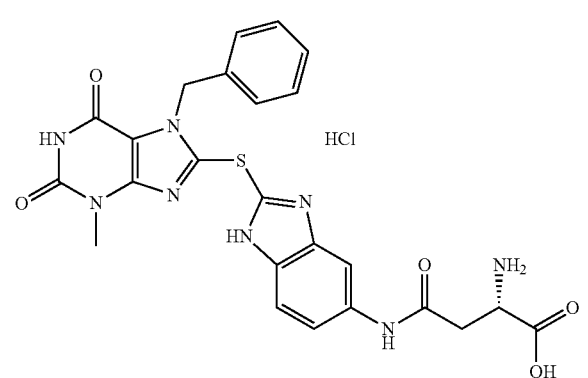

(I-40)

LCMS (method 1): $R_t$=1.024 min; HRMS (ESIpos): m/z [M+H]$^+$ calcd for $C_{24}H_{22}N_8O_5S$, 535.1507 found, 535.1501. $^1$H NMR (300 MHz, DMSO-d$_6$) δ 11.43 (s, 1H), 10.72 (s, 1H), 8.46 (d, J=4.4 Hz, 2H), 8.07 (s, 1H), 7.50 (d, J=8.8 Hz, 1H), 7.40 (dd, J=1.9, 8.8 Hz, 1H), 7.30-7.23 (m, 4H), 7.23-7.17 (m, 1H), 5.67 (s, 2H), 4.26 (dd, J=5.0, 5.1 Hz, 1H), 3.34 (s, 1H, overlay H$_2$O peak), 3.10-3.05 (m, 1H), 2.99 (s, 1H).

Example 47: (2S)-2-amino-4-({2-[(7-benzyl-3-methyl-2,6-dioxo-2,3,6,7-tetrahydro-1H-purin-8-yl)sulfanyl]-1H-1,3-benzodiazol-5-yl}carbamoyl)butanoic acid hydrochloride (KM 480)

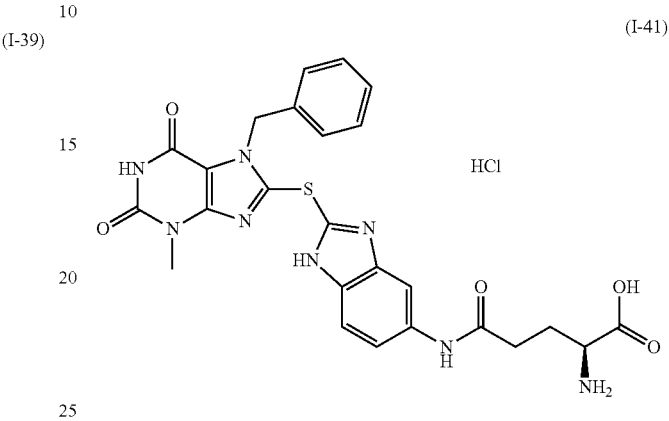

(I-41)

LCMS (method 1): $R_t$=1.028 min; HRMS (ESIpos): m/z [M+H]$^+$ calcd for $C_{25}H_{24}N_8O_5S$, 549.1663 found, 549.1670. $^1$H NMR (600 MHz, DMSO-d$_6$) δ 11.41 (s, 1H), 10.32 (s, 1H), 8.49 (d, J=5.6 Hz, 2H), 8.05 (s, 1H), 7.48 (d, J=8.7 Hz, 1H), 7.36 (dd, J=2.1, 8.9 Hz, 1H), 7.31-7.26 (m, 3H), 7.26-7.22 (m, 1H), 5.67 (s, 2H), 3.98-3.93 (m, 1H), 3.33 (s, 3H), 2.65 (ddd, J=6.6, 8.9, 15.7 Hz, 1H), 2.58-2.53 (m, 1H), 2.18-2.10 (m, 2H).

Example 48: 8-(1H-1,3-benzodiazol-2-ylsulfanyl)-3-methyl-7-{[4-(morpholin-4-yl)phenyl]methyl}-2,3,6,7-tetrahydro-1H-purine-2,6-dione (KM 483)

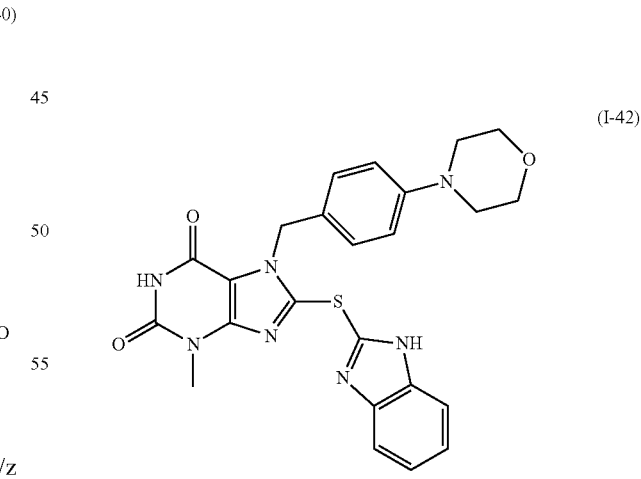

(I-42)

LCMS (method 1): $R_t$=1.151 min; HRMS (ESIpos): m/z [M+H]$^+$ calcd for $C_{24}H_{23}N_7O_3S$, 490.1656 found, 590.1681. $^1$H NMR (300 MHz, DMSO-d$_6$) δ 12.75 (s, 1H), 11.40 (s, 1H), 7.56 (d, J=7.2 Hz, 1H), 7.42 (d, J=7.2 Hz, 1H), 7.19 (d, J=8.4 Hz, 4H), 6.80 (d, J=8.6 Hz, 2H), 5.52 (s, 2H), 3.72-3.65 (m, 4H), 3.30 (s, 3H), 3.03-2.97 (m, 4H).

Example 49: N-(4-{[8-(1H-1,3-benzodiazol-2-ylsulfanyl)-3-methyl-2,6-dioxo-2,3,6,7-tetrahydro-1H-purin-7-yl]methyl}phenyl)acetamide (KM 489)

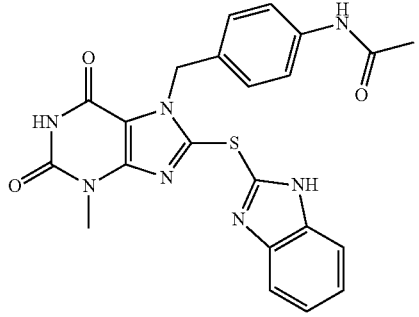
(I-43)

LCMS (method 1): $R_t$=1.070 min; HRMS (ESIpos): m/z [M+H]$^+$ calcd for $C_{22}H_{19}N_7O_3S$, 462.1343 found, 462.1338.

Example 50: 7-[(4-aminophenyl)methyl]-8-(1H-1,3-benzodiazol-2-ylsulfanyl)-3-methyl-2,3,6,7-tetrahydro-1H-purine-2,6-dione (KM 495)

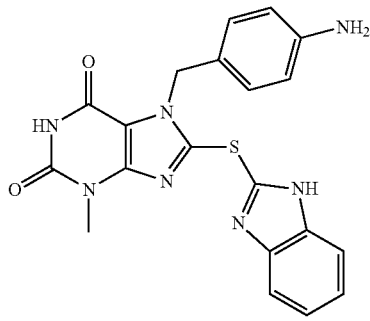
(I-44)

LCMS (method 1): $R_t$=0.976 min; HRMS (ESIpos): m/z [M+H]$^+$ calcd for $C_{20}H_{17}N_7O_2S$, 420.1237 found, 420.1239.

Example 51: 2-({2-[(7-benzyl-3-methyl-2,6-dioxo-2,3,6,7-tetrahydro-1H-purin-8-yl)sulfanyl]-1H-1,3-benzodiazol-5-yl}amino)acetic acid (KM 501)

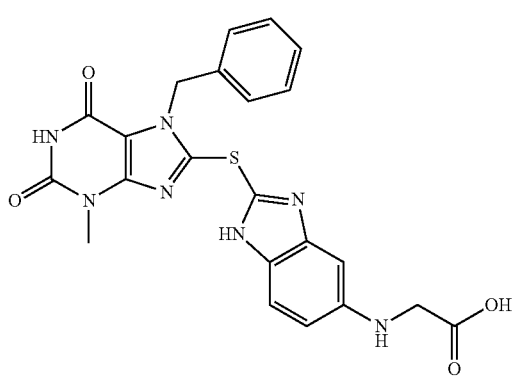
(I-45)

LCMS (method 1): $R_t$=1.082 min; HRMS (ESIpos): m/z [M+H]$^+$ calcd for $C_{22}H_{19}N_7O_4S$, 478.1292 found, 478.1300.

Example 52: 8-(1H-1,3-benzodiazol-2-ylsulfanyl)-7-benzyl-3-ethyl-2,3,6,7-tetrahydro-1H-purine-2,6-dione (MW-01-139)

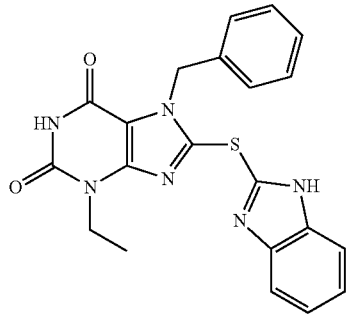
(I-46)

LCMS (method 1): $R_t$=1.234 min; HRMS (ESIpos): m/z [M+H]$^+$ calcd for $C_{21}H_{18}N_6O_2S$, 419.1285 found, 419.1276. $^1$H NMR (300 MHz, DMSO-d$_6$) δ 12.79 (s, 1H), 11.40 (s, 1H), 7.56 (d, J=6.8 Hz, 1H), 7.43 (d, J=6.9 Hz, 1H), 7.31-7.27 (m, 4H), 7.27-7.15 (m, 3H), 5.63 (s, 2H), 3.91 (q, J=7.1 Hz, 2H), 1.17 (t, J=7.1 Hz, 3H).

Example 53: 8-(1H-1,3-benzodiazol-2-ylsulfanyl)-7-benzyl-3-propyl-2,3,6,7-tetrahydro-1H-purine-2,6-dione (MW-01-153)

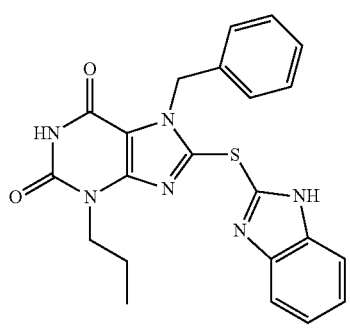
(I-47)

LCMS (method 1): $R_t$=1.273 min; HRMS (ESIpos): m/z [M+H]$^+$ calcd for $C_{22}H_{20}N_6O_2S$, 433.1447 found, 433.1458. $^1$H NMR (300 MHz, DMSO-d$_6$) δ 12.78 (s, 1H), 11.40 (s, 1H), 7.55 (d, J=6.7 Hz, 1H), 7.42 (d, J=7.5 Hz, 1H), 7.33-7.12 (m, 7H), 5.63 (s, 2H), 3.83 (t, J=7.4 Hz, 2H), 1.72-1.52 (m, 2H), 0.82 (t, J=7.4 Hz, 3H).

Example 54: 8-(1H-benzo[d]imidazol-2-ylamino)-7-benzyl-3-methyl-1H-purine-2,6(3H,7H)-dione (KM-05-145)

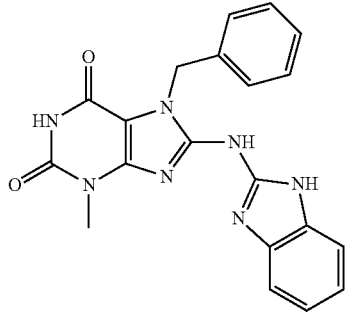

(I-301)

LCMS (method 1): $R_t$=1.255 min; HRMS (ESIpos): m/z [M+H]$^+$ calcd for $C_{20}H_{17}N_7O_2$, 388.1516 found, 388.1504.

Example 55: 8-(1H-benzo[d]imidazol-2-ylamino)-7-benzyl-3-ethyl-1H-purine-2,6(3H,7H)-dione (MW-01-148)

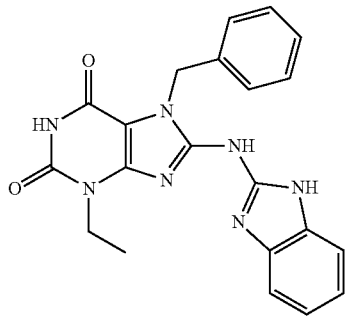

(I-302)

LCMS (method 1): $R_t$=1.312 min; HRMS (ESIpos): m/z [M+H]$^+$ calcd for $C_{21}H_{19}N_7O_2$, 402.1673 found, 402.1658. $^1$H NMR (DMSO-d$_6$, 300 MHz) δ 11.71 (s, 1H), 10.73 (s, 1H), 7.38-7.28 (m, 7H), 7.12 (dd, J=3.2, 5.9 Hz, 2H), 5.76 (s, 1H), 5.33 (s, 2H), 4.19 (q, J=6.8 Hz, 2H), 1.24 (t, J=6.9 Hz, 4H).

Example 56: 8-(1H-benzo[d]imidazol-2-ylamino)-7-benzyl-3-propyl-1H-purine-2,6(3H,7H)-dione (MW-01-162)

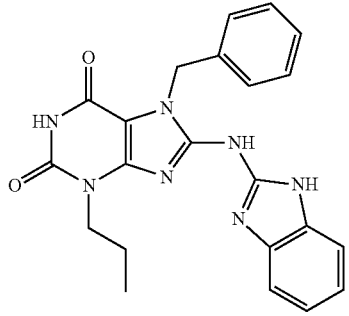

(I-303)

LCMS (method 1): $R_t$=1.338 min; HRMS (ESIpos): m/z [M+H]$^+$ calcd for $C_{22}H_{21}N_7O_2$, 416.1835 found, 416.1833. $^1$H NMR (300 MHz, DMSO-d$_6$) δ 11.73 (s, 1H), 10.73 (s, 1H), 7.38-7.29 (m, 6H), 7.28-7.22 (m, 1H), 7.11 (dd, J=3.2, 5.9 Hz, 2H), 5.33 (s, 2H), 4.11 (t, J=7.8 Hz, 3H), 1.75-1.65 (m, 2H), 0.92 (t, J=7.4 Hz, 3H).

In Vitro Enzyme Activity Assay

These compounds according to the afore-mentioned examples were tested for tryptophan hydroxylase (TPH) inhibitory activity in a fluorescence-based in vitro assay, using recombinant human TPH1 (Swiss-Prot: P17752) and TPH2 (Swiss-Prot: Q8IWU9).

The full-length coding sequences of human TPH1 and TPH2 were PCR amplified, ligated into a MBP fusion vector (pMalc2x, New England Biolabs, MA, USA) and transformed into SCS1 (Stratagene, CA, USA) to amplify plasmid DNA. For the overexpression of TPH proteins, the constructs were transformed into Rosetta (DE3) (Novagen®/EMD Millipore, MA, USA) and cultivated in terrific broth (TB) medium (AppliChem, Darmstadt, Germany) at 37° C. When the bacterial cultures reached an OD600≈2, expression was induced with 0.5 mM IPTG (AppliChem, Darmstadt, Germany) over night at 17° C. The purification of soluble proteins started with sonication-mediated cell disruption in lysis buffer (1×PBS pH 7.4, 0.5 M NaCl, 5% Glycerol+CHAPS, DTT, PMSF, benzonase), followed by affinity purification (MBPTrap, GE Healthcare, UK) and gel filtration (26/60 Superdex 200 prep grade, GE Healthcare, UK), according to the manufacturer's protocol. The quality of protein expression and solubility was controlled by SDS-PAGE and Coomassie blue staining.

The enzymatic reaction was carried out in black 96-well flat bottom plates (Corning GmbH, Wiesbaden). TPH1 and TPH2 activities were measured in a reaction mixture containing 50 mM 4-Morpholineethanesulfonic acid (MES), pH 7.0, 40 µM tryptophan, 200 mM ammonium sulfate, 25 µM ferrous ammonium sulfate, 50 µM tetrahydrobiopterin, 25 µg/ml catalase, and 7 mM DTT. The reactions were initiated by adding TPH1 or TPH2 to a final concentration of 5 µg/ml. Initial velocity of the reactions was determined by following the change of fluorescence at 330 nm (excitation wavelength=300 nm) (Infinite M200, Tecan, Crailsheim).

TPH1 and TPH2 inhibition was determined by measuring a compound dose response, using a serial dilution of a 5 mM DMSO stock solution. The potency of a given compound was calculated in GraphPad PRISM 6 software (San Diego, USA) with a Nonlinear Regression fit (log(inhibitor) vs. response-variable slope) using the relative fluorescence units (RFU) of the sample triplicates.

For comparative reasons, the TPH1 and TPH2 inhibition was tested under the same experimental condition with the inhibitors (LX1606 obtained from AdooQ BioScience, Irvine, Calif., USA), LX1031 (obtained from ApexBio Technology, Houston, Tex., USA) and LP533401 (obtained from Dalton Pharma Services, Toronto, CANADA).

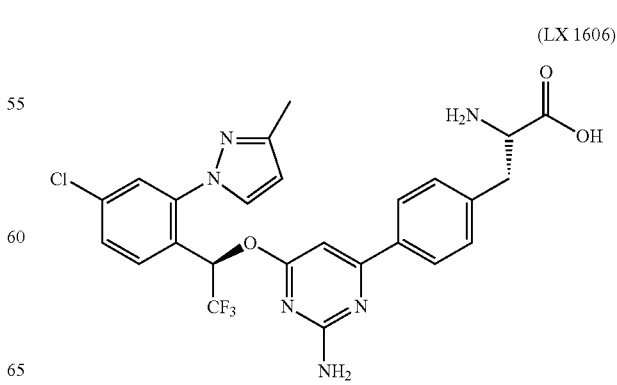

(LX 1606)

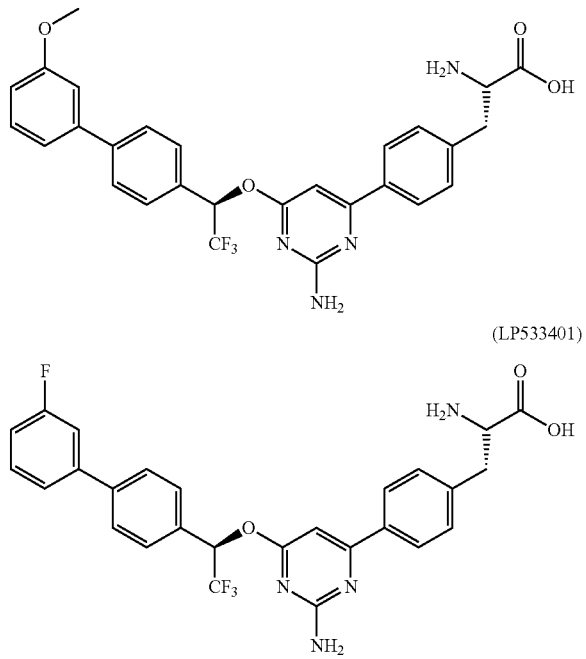

(LX1031)

(LP533401)

TABLE 1

Inhibition of TPH1

| IC$_{50}$ TPH1 (μM) | | compound[1] (Example Nr./Lab-Journal/ |
|---|---|---|
| mean | sd | Internat. Ref.) |
| 0.24 | 0.10 | Ex. 21/KM-05-185/(I-204) |
| 0.30 | 0.06 | Ex. 27/KM-05-193/(I-209) |
| 0.35 | 0.11 | Ex. 25/MW-01-157/(I-207) |
| 0.36 | 0.09 | Ex. 24/KM-05-166/(I-206) |
| 0.41 | 0.10 | Ex. 19/KM-05-130/(I-19) |
| 0.43 | 0.03 | Ex. 18/AG-01-128/(I-202) |
| 0.59 | 0.08 | Ex. 23/KM-05-139/(I-23) |
| 0.76 | 0.22 | Ex. 53/MW-01-153/(I-47) |
| 0.77 | 0.09 | LX1606 (comparative Example) |
| 0.83 | 0.21 | Ex. 52/MW-01-139/(I-46) |
| 0.85 | 0.14 | Ex. 1/KM-05-80/(I-1) |
| 0.85 | 0.24 | Ex.14/KM-05-179/(I-201) |
| 0.96 | 0.21 | Ex. 13/KM-05-125/(I-13) |
| 1.07 | 0.24 | Ex. 29/KM-06-20/(I-211) |
| 1.21 | 0.33 | Ex. 20/KM-05-173/(I-203) |
| 1.33 | 0.12 | Ex. 2/KM-05-89/(I-2) |
| 1.42 | 0.32 | LX1031 (comparative Example) |
| 1.56 | 0.25 | Ex. 28/KM-06-11/(I-210) |
| 1.60 | 0.15 | Ex. 15/KM-05-135/(I-15) |
| 1.62 | 0.18 | Ex. 17/KM-05-128/(I-17) |
| 1.80 | 0.33 | Ex. 12/KM-05-126/(I-12) |
| 1.96 | 0.48 | Ex. 22/KM-05-174/(I-205) |
| 2.01 | 0.56 | LP533401 (comparative Example) |
| 2.22 | 0.44 | Ex. 10/KM-05-60/(I-10) |
| 2.70 | 0.16 | Ex. 9/KM-05-93/(I-9) |
| 2.95 | 1.23 | Ex. 47/KM480/(I-41) |
| 4.11 | 0.52 | Ex. 7/KM-05-55 Fr16-17/(I-7) |
| 4.14 | 0.17 | Ex. 11/KM-05-100/(I-11) |
| 4.20 | 0.79 | Ex. 16/KM-05-127/(I-16) |
| 5.83 | 0.67 | Ex. 4/KM-05-50/(I-4) |
| 6.19 | 2.20 | Ex. 6/KM-05-55 Fr10-12/(I-6) |
| 7.40 | 2.59 | Ex. 37/KM430/(I-31) |
| 8.28 | 1.97 | Ex. 3/KM-05-16/(I-3) |
| 9.05 | 2.95 | Ex. 30/KM406/(I-24) |
| 9.48 | 5.81 | Ex. 31/KM422/(I-25) |
| 9.72 | 5.36 | Ex. 46/KM477/(I-40) |
| 10.71 | 3.31 | Ex. 8/KM-05-68/(I-8) |

TABLE 1-continued

Inhibition of TPH1

| IC$_{50}$ TPH1 (μM) | | compound[1] (Example Nr./Lab-Journal/ |
|---|---|---|
| mean | sd | Internat. Ref.) |
| 14.46 | 3.17 | Ex. 51/KM501/(I-45) |
| 15.03 | 9.29 | Ex. 41/KM446/(I-35) |
| 20.02 | 19.91 | Ex. 33/KM424/(I-27) |
| 20.77 | 13.76 | Ex. 26/KM-05-180/(I-208) |
| 25.15 | 15.19 | Ex. 42/KM447/(I-36) |
| 33.01 | 6.03 | Ex. 49/KM489/(I-43) |
| 42.22 | 25.16 | Ex. 43/KM448/(I-37) |
| 63.59 | 28.88 | Ex. 50/KM495/(I-44) |
| 76.00 | 39.15 | Ex. 48/KM483/(I-42) |
| >200 | | Ex. 5/KM-05-52/(I-5) |
| >200 | | Ex. 32/KM423/(I-26) |
| >200 | | Ex. 34/KM425/(I-28) |
| >200 | | Ex. 35/KM427/(I-29) |
| >200 | | Ex. 36/KM429/(I-30) |
| >200 | | Ex. 38/KM431/(I-32) |
| >200 | | Ex. 39/KM432/(I-33) |
| >200 | | Ex. 40/KM435/(I-34) |
| >200 | | Ex. 44/KM449/(I-38) |
| >200 | | Ex. 45/KM450/(I-39) |
| >200 | | Ex. 54/KM-05-145/(I-301) |
| >200 | | Ex. 55/MW-01-148/(I-302) |
| >200 | | Ex. 56/MW-01-162/(I-303) |

TABLE 2

Inhibition of TPH2

| IC$_{50}$ TPH2 (μM) | | compound[1] (Example Nr./Lab-Journal/ |
|---|---|---|
| mean | sd | Internat. Ref.) |
| 0.014 | 0.004 | Ex. 27/KM-05-193/(I-209) |
| 0.014 | 0.006 | Ex. 24/KM-05-166/(I-206) |
| 0.02 | 0.007 | Ex. 18/AG-01-128/(I-202) |
| 0.02 | 0.01 | Ex. 21/KM-05-185/(I-204) |
| 0.02 | 0.01 | Ex. 25/MW-01-157/(I-207) |
| 0.04 | 0.02 | Ex. 14/KM-05-179/(I-201) |
| 0.04 | 0.01 | Ex. 52/MW-01-139/(146) |
| 0.05 | 0.006 | Ex. 23/KM-05-139/(I-23) |
| 0.05 | 0.02 | Ex. 53/MW-01-153/(I-47) |
| 0.05 | 0.02 | Ex. 20/KM-05-173/(I-203) |
| 0.06 | 0.017 | Ex. 19/KM-05-130/(I-19) |
| 0.06 | 0.02 | Ex. 22/KM-05-174/(I-205) |
| 0.07 | 0.02 | Ex. 13/KM-05-125/(I-13) |
| 0.07 | 0.02 | Ex. 1/ KM-05-80/(I-1) |
| 0.09 | 0.03 | Ex. 28/KM-06-11/(I-210) |
| 0.10 | 0.02 | Ex. 29/KM-06-20/(I-211) |
| 0.10 | 0.02 | Ex. 2/KM-05-89/(I-2) |
| 0.14 | 0.05 | Ex. 15/KM-05-135/(I-15) |
| 0.14 | 0.06 | Ex. 17/KM-05-128/(I-17) |
| 0.17 | 0.03 | Ex. 4/KM-05-50/(I-4) |
| 0.17 | 0.01 | Ex. 10/KM-05-60/(I-10) |
| 0.19 | 0.01 | Ex. 9/KM-05-93/(I-9) |
| 0.23 | 0.07 | Ex. 12/KM-05-126/(I-12) |
| 0.23 | 0.09 | Ex. 47/KM480/(I-41) |
| 0.29 | 0.01 | Ex. 7/KM-05-55 Fr16-17/(I-7) |
| 0.43 | 0.20 | Ex. 31/KM422/(I-25) |
| 0.45 | 0.16 | Ex. 16/KM-05-127/(I-16) |
| 0.49 | 0.21 | Ex. 37/KM430/(I-31) |
| 0.49 | 0.18 | Ex. 41/KM446/(I-35) |
| 0.57 | 0.60 | Ex. 33/KM424/(I-27) |
| 0.69 | 0.09 | Ex. 6/KM-05-55 Fr10-12/(I-6) |
| 0.73 | 0.10 | LX1606 (comparative Example) |
| 0.74 | 0.11 | Ex. 11/KM-05-100/(I-11) |
| 0.76 | 0.13 | Ex. 5/KM-05-52/(I-5) |
| 0.82 | 0.18 | Ex. 3/KM-05-16/(I-3) |
| 0.83 | 0.38 | Ex. 46/KM477/(I-40) |
| 0.85 | 0.28 | Ex. 26/KM-05-180/(I-208) |
| 0.90 | 0.44 | Ex. 42/KM447/(I-36) |
| 0.92 | 0.25 | Ex. 30/KM406/(I-24) |
| 1.09 | 0.11 | Ex. 8/KM-05-68/(I-8) |

TABLE 2-continued

Inhibition of TPH2

| IC$_{50}$ TPH2 (µM) | | compound[1] (Example Nr./Lab-Journal/ |
|---|---|---|
| mean | sd | Internat. Ref.) |
| 1.24 | 0.27 | Ex. 49/KM489/(I-43) |
| 1.33 | 0.62 | Ex. 48/KM483/(I-42) |
| 1.39 | 0.30 | Ex. 51/KM501/(I-45) |
| 1.41 | 0.86 | Ex. 43/KM448/(I-37) |
| 1.63 | 0.31 | LX1031 (comparative Example) |
| 2.06 | 0.75 | Ex. 45/KM450/(I-39) |
| 2.23 | 0.50 | LP533401 (comparative Example) |
| 2.68 | 1.34 | Ex. 39/KM432/(I-33) |
| 3.49 | 1.62 | Ex. 44/KM449/(I-38) |
| 4.00 | 0.46 | Ex. 50/KM495/(I-44) |
| 15.7 | 22.7 | Ex. 34/KM425/(I-28) |
| 29.3 | 12.7 | Ex. 55/MW-01-148/(I-302) |
| >200 | | Ex. 32/KM423/(I-26) |
| >200 | | Ex. 35/KM427/(I-29) |
| >200 | | Ex. 36/KM429/(I-30) |
| >200 | | Ex. 38/KM431/(I-32) |
| >200 | | Ex. 40/KM435/(I-34) |
| >200 | | Ex. 54/KM-05-145/(I-301) |
| >200 | | Ex. 56/MW-01-162/(I-303) |

The data show that the xanthine derivatives according to the invention have an inhibiting effect with respect to the enzymatic activity of TPH1 and TPH2 which is at least comparable to the known compounds LX1606 and LP533401. In case of the inhibition of TPH2, several of the xanthine derivatives according to the invention even have a superior inhibiting effect over the known compounds.

Furthermore, it appears that the inhibition capability of those compounds comprising a methylene link between the xanthine and the benzimidazol moiety, i.e. Q=—CH$_2$— in formula I, tends to be higher than that of the thio- and amino derivatives with Q=S. This applies for both, the inhibition of TPH1 and TPH2.

Interestingly, some of the xanthine derivatives according to the invention show a selective inhibition addressing only one of TPH1 and TPH2. For instance, compounds KM-05-52, KM432 and KM449 of Experiments 5, 39 and 44 which are less active towards TPH1 exhibit a good inhibiting effect of TPH2. This behavior enables to selectively inhibit TPH2 without affecting TPH1.

Crystallographic Analysis

Compound KM480 was co-crystallized with human TPH1 and the crystal structure was analyzed by x-ray diffraction. FIG. 1A shows a superimposition of the crystal structure of human TPH1 in complex with KM480 (overall fold as gray cartoon model and inhibitor as gray stick model) and with the literature known LP533401 (overall fold as black cartoon model and inhibitor as black stick model, pdb code: 3HF8) In FIG. 1B the binding configurations of the inhibitors KM480 and LP533401 with respect to the binding pockets of the enzyme are depicted. FIGS. 1A and B exhibit an unexpected binding mode of KM480 addressing the binding site of TPH1. In comparison to the inhibitor-complex with LP533401, KM480 occupies a partly different space in the binding site. It is deeply buried in the binding pocket of the co-substrate tetrahydrobiopterin (BH$_4$) with its xanthine scaffold whereas the adjacent benzyl-group forms π-π interactions with the tyrosine Y235. Y235 is thereby involved in a conformational shift of nearly 90° compared to the known crystal structure 3HF8. The benzimidazolyl moiety sticks into the binding pocket of the substrate tryptophan and the amino acid head group of KM480 resembles a similar binding mode as in the case of LP533401. The unexpected conformational changes of the enzyme combined with the novel binding mode of KM480 explains the high affinity of the new inhibitor class and gives insights into a crystal structure of TPH1 which was never been described in the literature before.

The invention claimed is:

1. A xanthine derivative defined by chemical Formula I or a salt thereof:

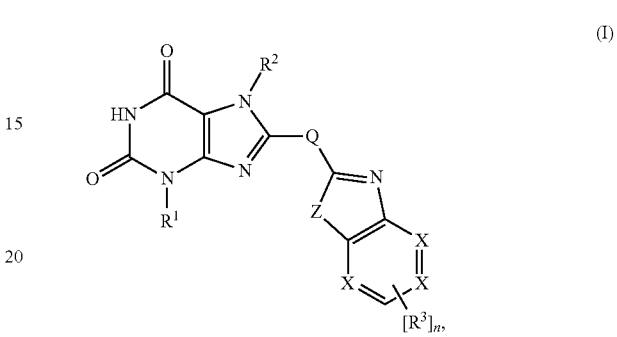

(I)

wherein R$^1$ and R$^2$ are each an optionally substituted group independently selected from hydrogen (—H), (C1-C10)-alkyl, (C2-C10)-alkenyl, (C2-C10)-alkynyl, (C5-C14)-aryl, (C5-C14)-heteroaryl, (C6-C15)-alkyl-aryl, (C6-C15)-alkyl-heteroaryl, (C6-C15)-alkenyl-aryl, (C6-C15)-alkenyl-heteroaryl, (C6-C15)-alkynyl-aryl, (C6-C15)-alkynyl-heteroaryl, (C6-C15)-aryl-alkylene, (C6-C15)-heteroaryl-alkylene, (C6-C15)-aryl-alkenylene, (C6-C15)-heteroaryl-alkenylene, (C6-C15)-aryl-alkylylene and (C6-C15)-heteroaryl-alkylylene, wherein the alkyl, alkenyl, alkynyl, alkylene, alkylene and alkenylene groups optionally comprise one or more bivalent groups substituting a carbon moiety in their hydrocarbon chain and selected from —O—, —S—, —S(O)—, —SO$_2$—, —N=, —N(R)—, —C(O)—, —C(O)O—, —OC(O)—, —C(O)N(R)—, —N(R)C(O)—, —OC(O)N(R)—, —N(R)C(O)O—, —N(R)C(O)N(R)—, (C3-C12)-heterocyclic alkylene and (C3-C12)-heterocyclic alkenylene;

R$^3$ means a number of n groups independently selected from hydrogen (—H), fluoro (—F), bromo (—Br), chloro (—Cl), hydroxyl (—OH), carbonyl (—C(O)R), carboxyl (—C(O)OH), carboxy ester (—CO$_2$R), alkoxy (—OR), aldehyde (—C(O)H), trihalide methyl ester (—OCX$_3$), primary, secondary and tertiary amine (—NR(R')), amide (—N(R)—C(O)—R), imide (—C(O)—N(R)—C(O)—R'), carbamate (—N(R)—C(O)—OR'), carboxamide (—C(O)N(R)R'), carbimide (—N(R)—C(O)—N(R')R''), primary and secondary ketimine (—(R)=NR'), secondary ketimine (—(R)=NH), nitrile (—CN), isonitrile (—NC), nitroxy (—ONO), nitro (—NO$_2$), nitrate (—ONO$_2$), nitroso (—NO), cyanate (—OCN), isocyanate (—NCO), sulfhydryl (—SH), sulfide (—SR), sulfurtrihalide (—SX$_3$), sulfurpentahalide (—SX$_5$), sulfinyl (—S(O)R), sulfonyl (—SO$_2$R), sulfino (—SO$_2$H), and sulfo (—SO$_3$H), and an optionally substituted and optionally linked group selected from (C1-C10)-alkyl, (C2-C10)-alkenyl, (C2-C10)-alkynyl, (C5-C14)-aryl, (C5-C14)-heteroaryl, (C6-C15)-alkyl-aryl, (C6-C15)-alkyl-heteroaryl, (C6-C15)-alkenyl-aryl, (C6-C15)-alkenyl-heteroaryl, (C6-C15)-alkynyl-aryl, (C6-C15)-alkynyl-heteroaryl, (C6-

C15)-aryl-alkylene, (C6-C15)-heteroaryl-alkylene, (C6-C15)-aryl-alkenylene, (C6-C15)-heteroaryl-alkenylene, (C6-C15)-aryl-alkylylene and (C6-C15)-heteroaryl-alkylylene, wherein the alkyl, alkenyl, alkynyl, alkylene, alkylene and alkenylene groups optionally comprise one or more bivalent groups substituting a carbon moiety in their hydrocarbon chain and selected from —O—, —S—, —S(O)—, —SO$_2$—, —N═, —N(R)—, —C(O)—, —C(O)O—, —OC(O)—, —C(O)N(R)—, —N(R)C(O)—, —OC(O)N(R)—, —N(R)C(O)O—, —N(R)C(O)N(R)—, (C3-C12)-heterocyclic alkylene or (C3-C12)-heterocyclic alkenylene;

Q is selected from methylene (—C(R)H—) and amino (—N(R)—);

X is selected from carbon (—C—) and nitrogen (—N—);

Z is selected from amino (—NH—), oxygen (—O—) and sulfur (—S—); and n is a number selected from 1, 2 and 3;

wherein in the aforementioned definitions R, R' and R" independently mean hydrogen, (C1-C3)-alkyl or (C2-C3)-alkenyl.

2. The xanthine derivative according to claim 1, wherein at least one of R$^1$ and R$^2$ is not hydrogen.

3. The xanthine derivative according to claim 1, wherein R$^1$ is selected from an optionally substituted linear, branched or cyclic (C1-05)-alkyl group, from the group consisting of methyl, ethyl, n-propyl, isopropyl, cyclopropyl, cyclobutyl and cyclopentyl.

4. The xanthine derivative according to claim 1, wherein R$^2$ is selected from an optionally substituted (C5-C12)-aryl, (C5-C12)-heteroaryl, (C6-C12)-alkyl-aryl, (C6-C12)-alkyl-heteroaryl, (C6-C12)-alkenyl-aryl, (C6-C12)-alkenyl-heteroaryl, (C6-C12)-alkynyl-aryl, (C6-C12)-alkynyl-heteroaryl, (C6-C12)-aryl-alkylene, (C6-C12)-heteroaryl-alkylene, (C6-C12)-aryl-alkenylene, (C6-C12)-heteroaryl-alkenylene, (C6-C12)-aryl-alkylylene and (C6-C12)-heteroaryl-alkylylene.

5. The xanthine derivative according to claim 1, wherein R$^2$ is a group defined by chemical formula (Ia), —R$^5$—Ar (Ia), wherein R$^5$ is (C0-C3)-alkylene, and Ar is an optionally substituted (C5-C12)-aryl or (C5-C12)-heteroaryl.

6. The xanthine derivative according to claim 1, wherein R$^3$ is hydrogen, fluorine, chlorine, bromine, amine, amide, carbonitrile optionally substituted (C1-C10)-alkyl, optionally substituted saturated or unsaturated (C5-C6)-heterocyclic, optionally substituted (C2-C10)-alkenyl, optionally substituted (C1-05)-alkoxy, wherein the alkyl and alkenyl groups optionally comprise one or more bivalent groups as defined above.

7. The xanthine derivative according to claim 1, wherein X is carbon.

8. The xanthine derivative according to claim 1, wherein Z is an amino group (—NH—).

9. The xanthine derivative according to claim 1, wherein Q is a methylene group (—CH$_2$—).

10. A medicament comprising the Xanthine derivative according to claim 1.

11. A pharmaceutical preparation comprising the xanthine derivative according to claim 1 or a pharmaceutically acceptable salt thereof.

12. The xanthine derivative, selected from the compounds represented by chemical Formulas (I-1) to (I-47), (I-201) to (I-211), and (I-301) to (I-303):

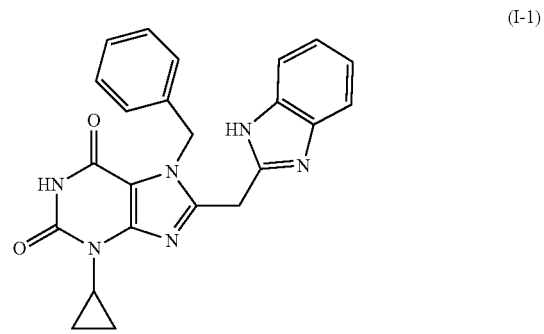

(I-1)

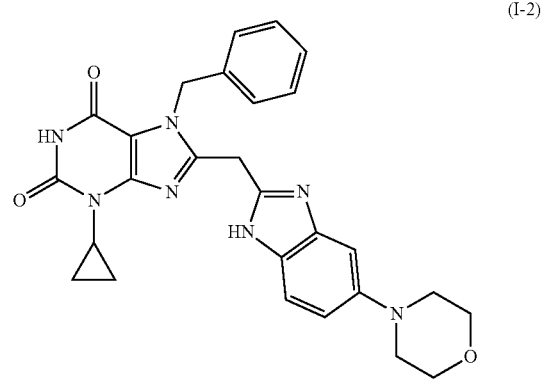

(I-2)

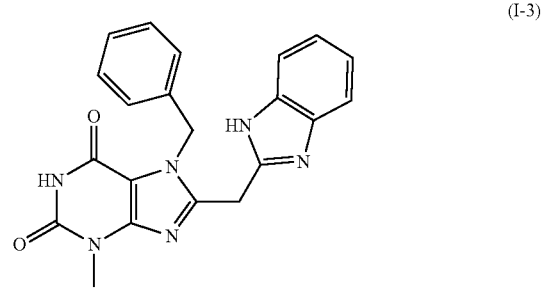

(I-3)

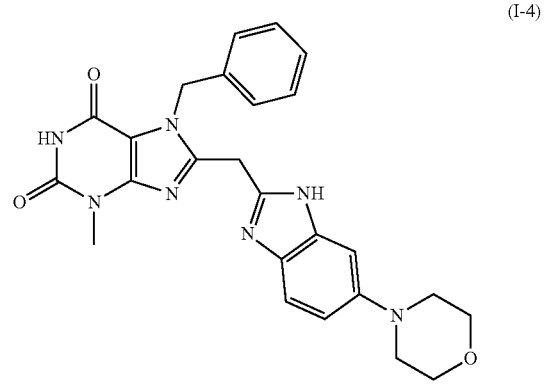

(I-4)

(I-5)
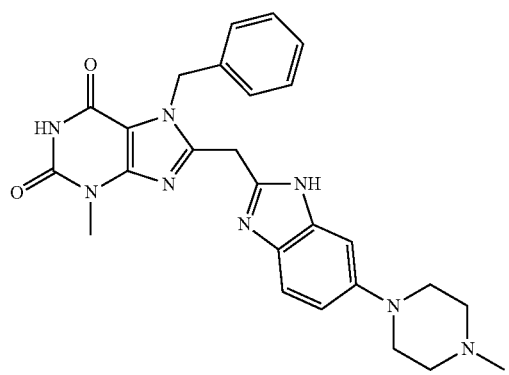
(I-6)
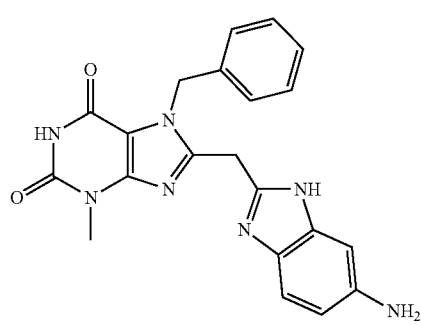
(I-7)
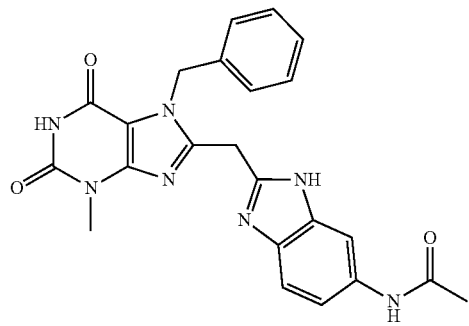
(I-8)
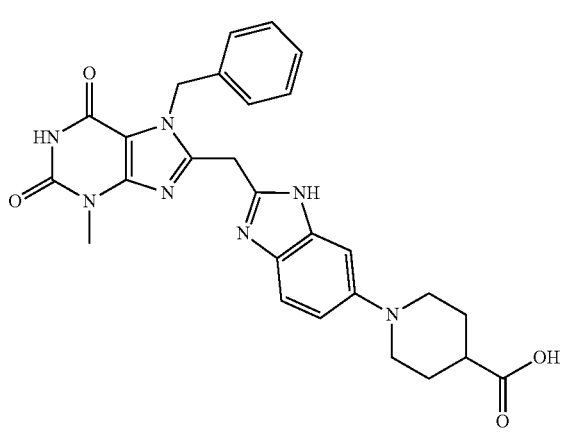
(I-9)
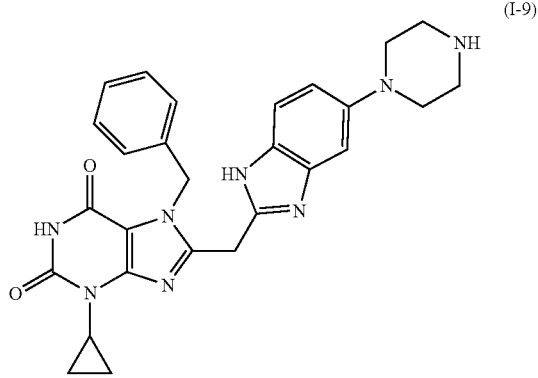
(I-10)
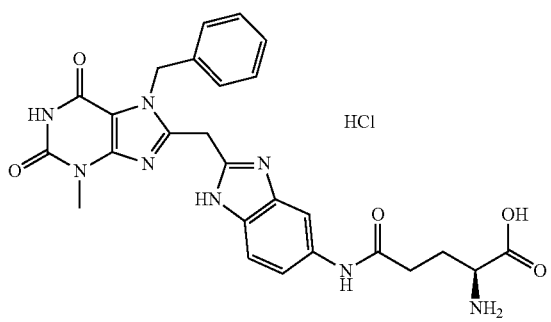
(I-11)
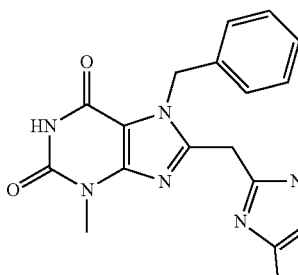
(I-12)
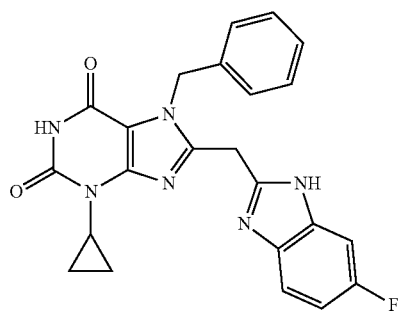

(I-13)
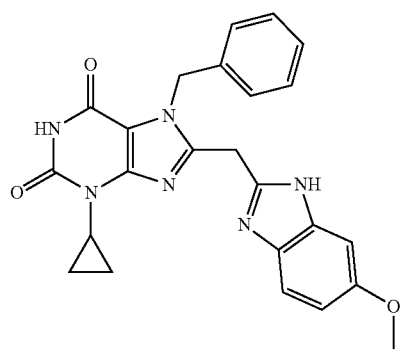
(I-14)
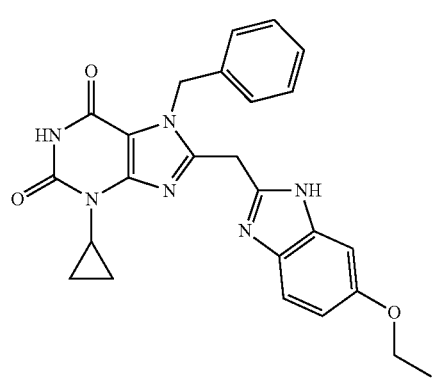
(I-15)
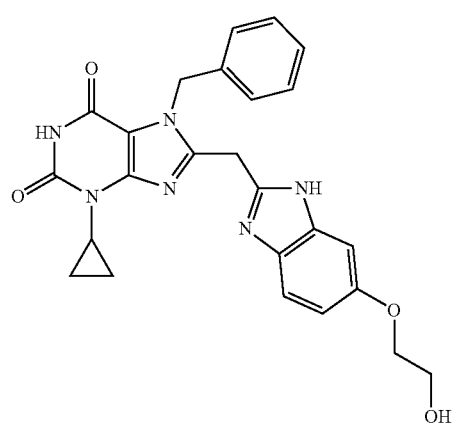
(I-16)
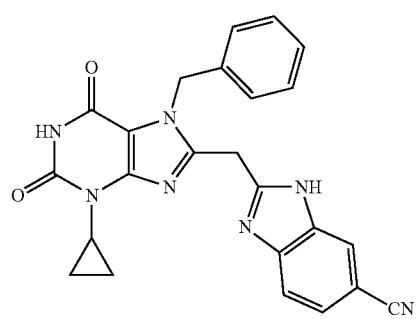
(I-17)
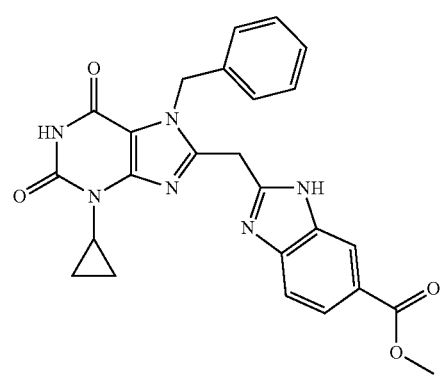
(I-18)
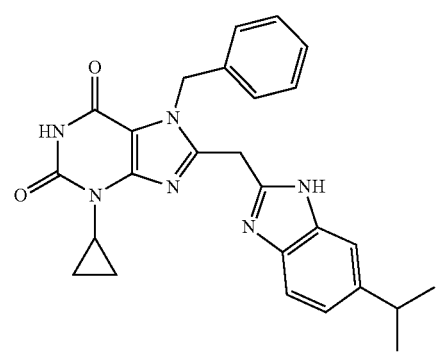
(I-19)
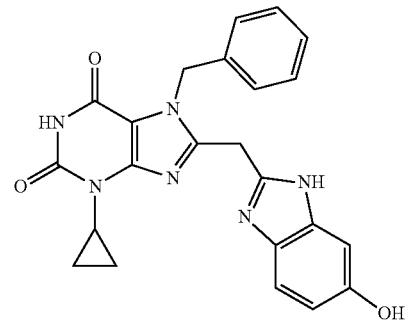
(I-20)
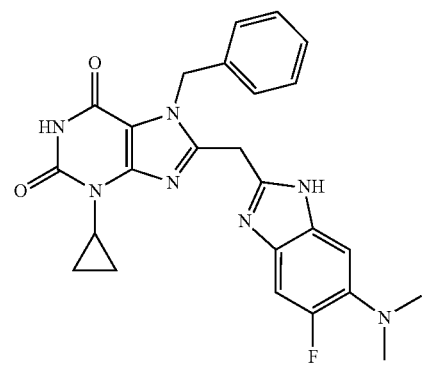

(I-21)
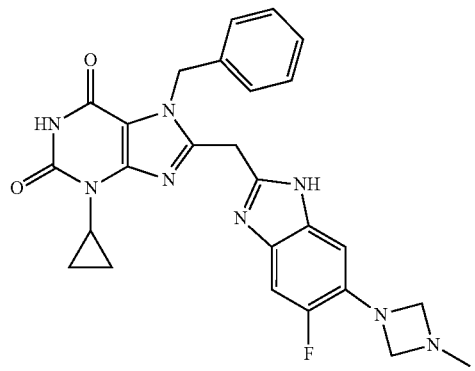
(I-22)
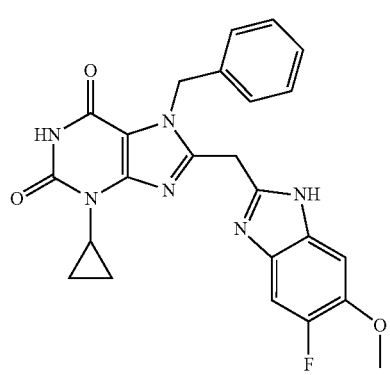
(I-23)
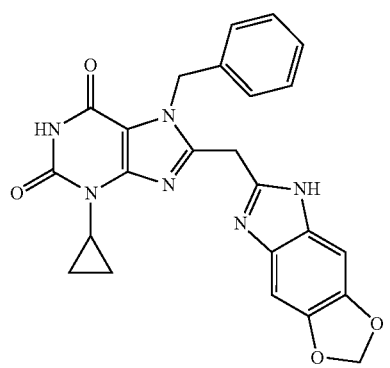
(I-201)
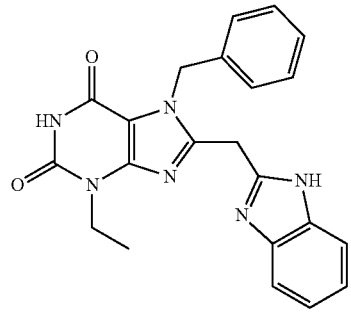
(I-202)
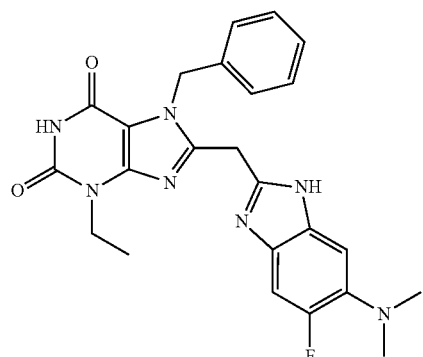
(I-203)
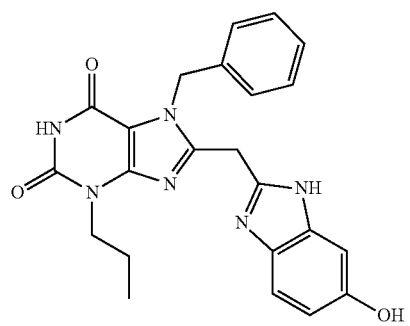
(I-204)
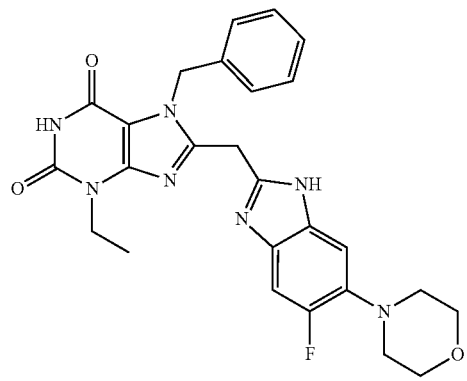
(I-205)

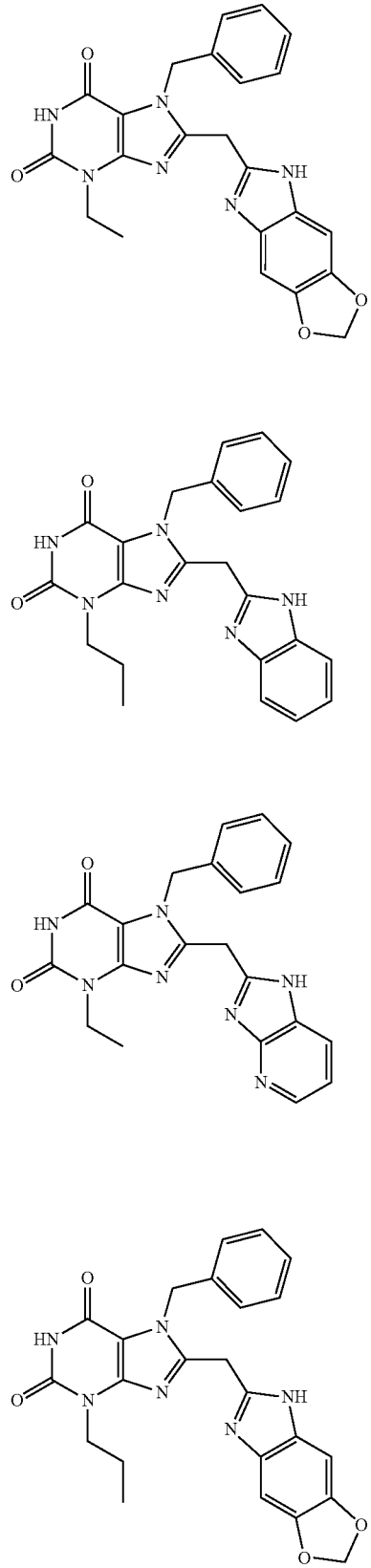
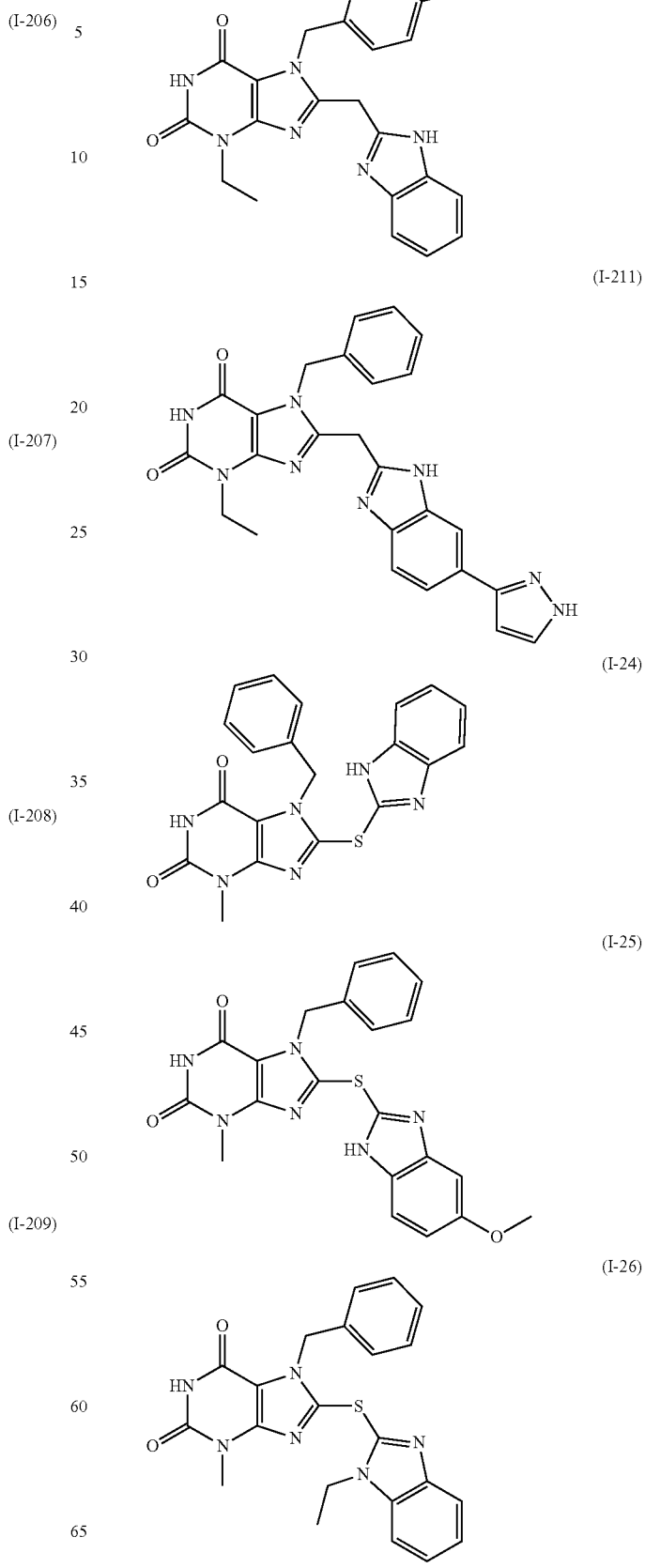

(I-27)
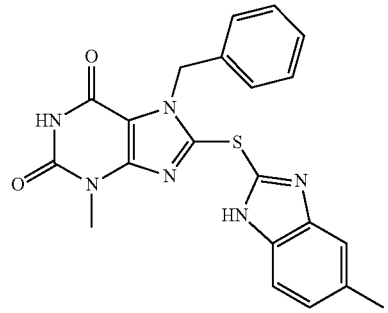
(I-28)
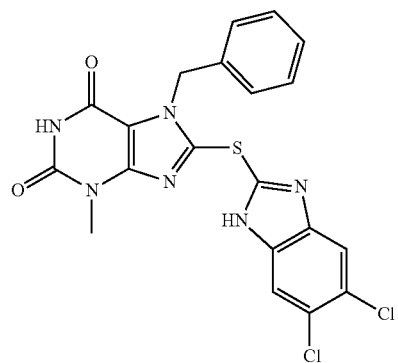
(I-29)
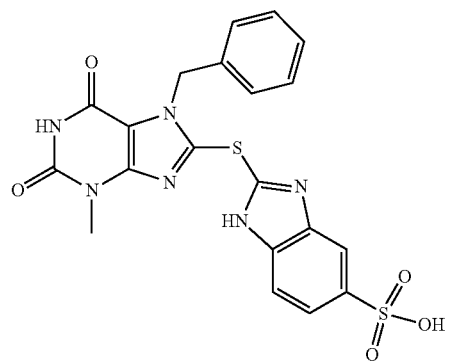
(I-30)
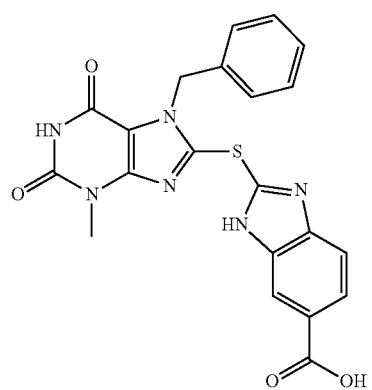
(I-31)
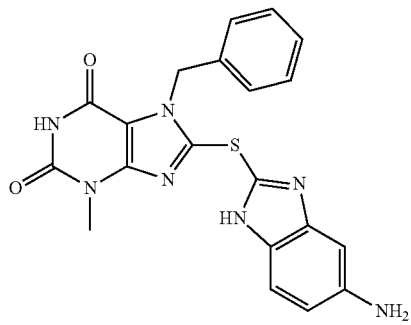
(I-32)
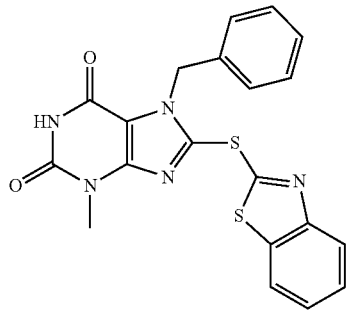
(I-33)
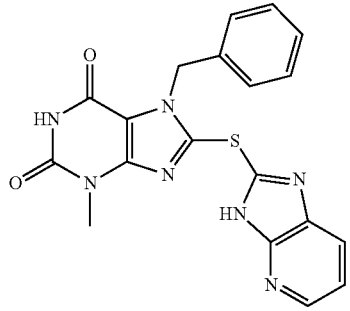
(I-34)
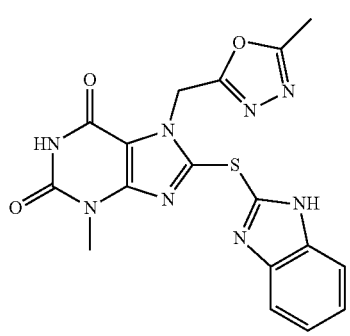
(I-35)
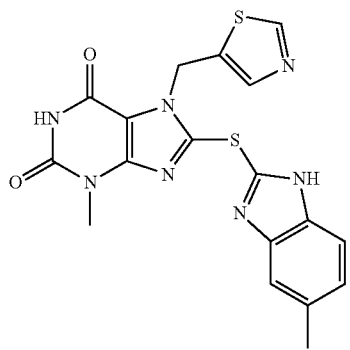

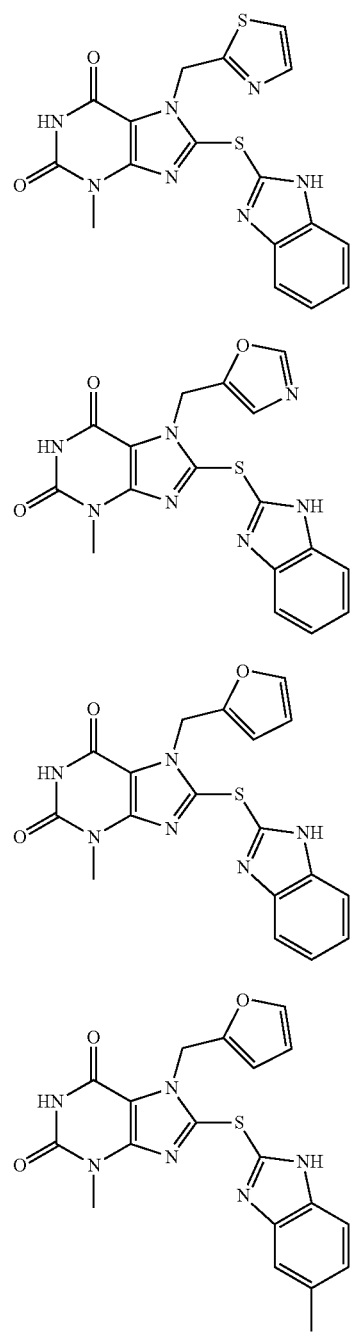
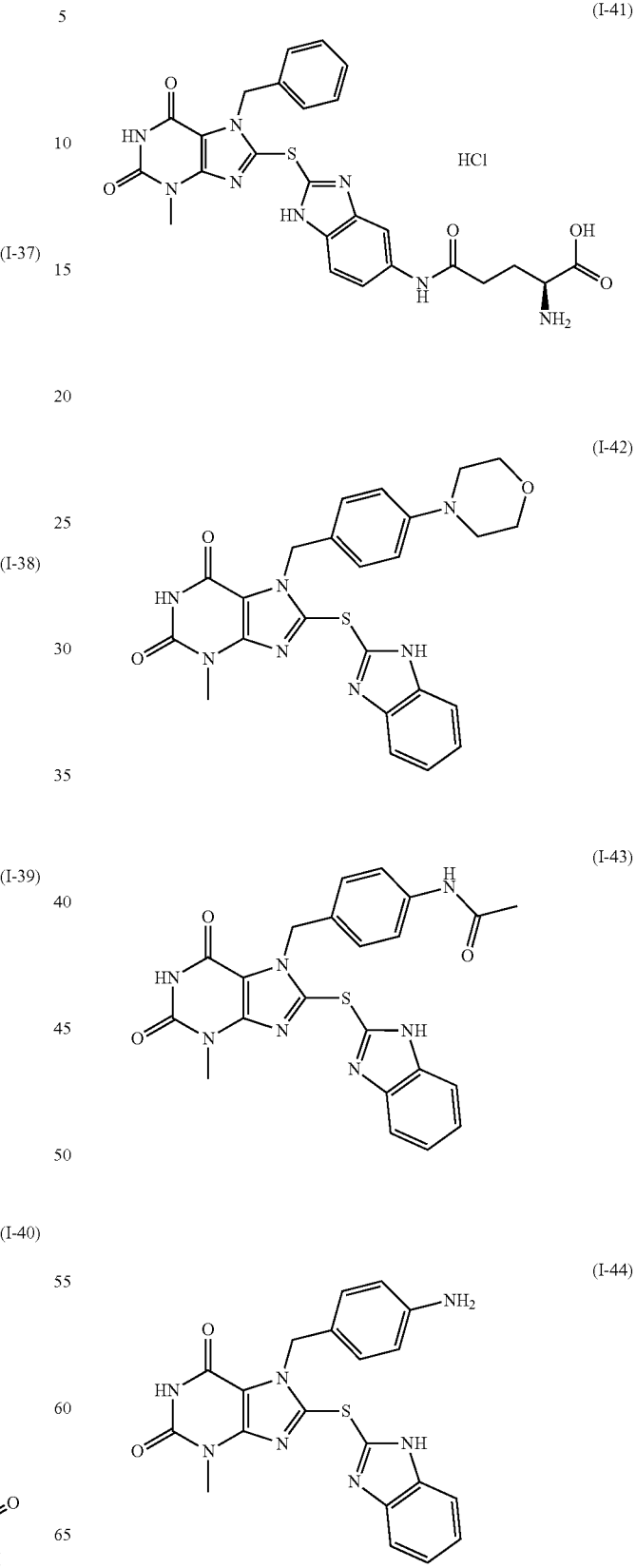

(I-45)

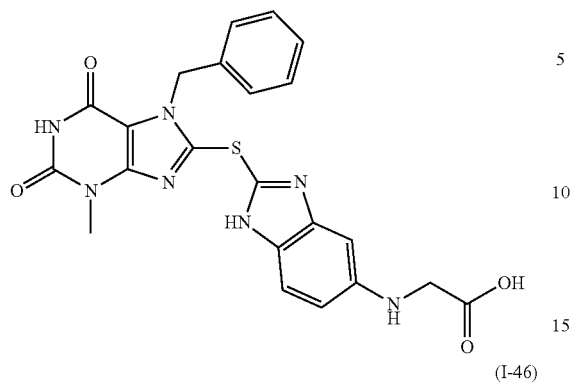

(I-46)

(I-47)

(I-301)

(I-302)

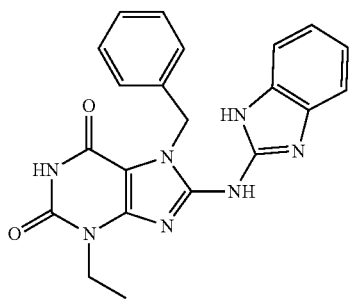

(I-303)

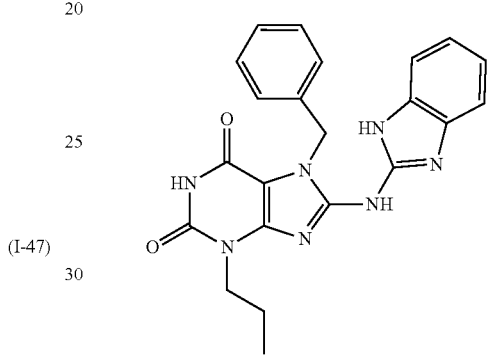

13. A method for alleviating or inhibiting the progress or reducing the severity of a serotonin-related disease or disorder, or conditions or symptoms associated with such a disease or disorder, comprising administering a pharmaceutically effective amount of the xanthine derivative according to claim 1.

14. The method according to claim 13, wherein the serotonin-related disease or disorder is selected from serotonin syndrome; bone diseases; immunological diseases; Pulmonary diseases; gastrointestinal diseases; cancer; vascular diseases; inflammatory diseases; metabolic diseases; and psychiatric diseases.

* * * * *